(12) United States Patent
Hussain et al.

(10) Patent No.: US 12,364,793 B2
(45) Date of Patent: Jul. 22, 2025

(54) INJECTABLE BIOPOLYMER COMPOSITIONS AND ASSOCIATED SYSTEMS AND METHODS

(71) Applicant: Covidien LP, Mansfield, MA (US)

(72) Inventors: Ali M. Hussain, Mission Viejo, CA (US); Tejashri Kumar, Fountain Valley, CA (US); John M. Wainwright, Foothill Ranch, CA (US); Junwei Li, Irvine, CA (US); Drew P. Amery, Jacksonville, FL (US); Jie Wen, Santa Rosa, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/654,950

(22) Filed: Mar. 15, 2022

(65) Prior Publication Data

US 2022/0296788 A1    Sep. 22, 2022

Related U.S. Application Data

(60) Provisional application No. 63/161,582, filed on Mar. 16, 2021, provisional application No. 63/161,597, filed on Mar. 16, 2021.

(51) Int. Cl.
| | | |
|---|---|---|
| A61L 31/14 | (2006.01) | |
| A61L 31/04 | (2006.01) | |
| A61L 31/16 | (2006.01) | |

(52) U.S. Cl.
CPC ........... *A61L 31/145* (2013.01); *A61L 31/042* (2013.01); *A61L 31/143* (2013.01); *A61L 31/16* (2013.01)

(58) Field of Classification Search
CPC ......... A61B 17/12113; A61B 17/12186; A61L 2430/36; C08L 5/08
See application file for complete search history.

(56) References Cited

U.S. PATENT DOCUMENTS

| | | | |
|---|---|---|---|
| 5,354,295 A | 10/1994 | Guglielmi et al. | |
| 5,669,931 A | 9/1997 | Kupiecki et al. | |
| 5,951,599 A | 9/1999 | McCrory | |
| 6,309,367 B1 | 10/2001 | Boock | |
| 6,454,780 B1 | 9/2002 | Wallace | |
| 6,591,472 B1 | 7/2003 | Noone et al. | |
| 6,602,261 B2 | 8/2003 | Greene et al. | |
| 6,605,101 B1 | 8/2003 | Schaefer et al. | |
| 6,878,384 B2 | 4/2005 | Cruise et al. | |
| 7,098,194 B2 | 8/2006 | Chenite et al. | |
| 7,229,461 B2 | 6/2007 | Chin et al. | |
| 7,601,160 B2 | 10/2009 | Richter | |
| 7,799,767 B2 * | 9/2010 | Lamberti | A61F 2/0063 514/80 |
| RE42,625 E | 8/2011 | Guglielmi | |
| 8,043,326 B2 | 10/2011 | Hancock et al. | |
| 8,153,612 B2 | 4/2012 | Ben-Shalom et al. | |
| 8,425,541 B2 | 4/2013 | Masters et al. | |
| 8,470,013 B2 | 6/2013 | Duggal et al. | |
| 8,530,632 B2 | 9/2013 | Tijsma et al. | |
| 8,653,319 B2 | 2/2014 | Amery et al. | |
| 8,715,317 B1 | 5/2014 | Janardhan et al. | |
| 8,809,301 B2 | 8/2014 | Athanasiadis et al. | |
| 8,840,867 B2 | 9/2014 | Sophie et al. | |
| 8,906,057 B2 | 12/2014 | Connor et al. | |
| 9,034,348 B2 | 5/2015 | Ben-Shalom et al. | |
| 9,192,574 B2 | 11/2015 | Medina et al. | |
| 9,192,692 B2 | 11/2015 | Medina et al. | |
| 9,211,202 B2 | 12/2015 | Strother et al. | |
| 9,333,220 B2 | 5/2016 | Tijsma et al. | |
| 9,433,636 B2 | 9/2016 | Tijsma et al. | |
| 9,486,224 B2 | 11/2016 | Riina et al. | |
| 9,555,120 B2 | 1/2017 | Andersson | |
| 9,655,842 B1 | 5/2017 | Girdhar et al. | |
| 9,700,648 B2 | 7/2017 | Hissong et al. | |
| 9,731,043 B2 | 8/2017 | Lerouge et al. | |
| 9,833,309 B2 | 12/2017 | Levi et al. | |
| 9,844,380 B2 | 12/2017 | Furey | |
| 9,901,543 B2 | 2/2018 | Chausson et al. | |

(Continued)

FOREIGN PATENT DOCUMENTS

| | | |
|---|---|---|
| CN | 105105812 A | 12/2015 |
| CN | 105209075 A | 12/2015 |

(Continued)

OTHER PUBLICATIONS

Fawal, Gomaa F. El, International Journal of Biological Macromolecules 111 (2018), pp. 649-659 (Year: 2018).*
Naderi-Meshkin, Hojjat, et al., Cell Biol Int 38 (2014) pp. 72-84 (Year: 2014).*
Ashland, Natrosol 250, (2018) pp. 1-32 (Year: 2018).*
International Search Report and Written Opinion mailed Aug. 9, 2022; International Application No. PCT/US2022/071166; 10 pages.
Medtronic ENT. (2021). Discover Novapak: Beyond Structural Stability [Brochure]. Medtronic.
Coutu, Jean-Michel, et al., "A new radiopaque embolizing agent for the treatment of endoleaks after endovascular repair: Influence of contrast agent on chitosan thermogel properties", Journal of Biomedical Materials Research Part B: Applied Biomaterials, 101B(1), 153-161. https://doi.org/10.1002/jbm.b.32828.

(Continued)

*Primary Examiner* — Andrew S Rosenthal
*Assistant Examiner* — Lyndsey M Beckhardt
(74) *Attorney, Agent, or Firm* — Fortem IP LLP

(57) ABSTRACT

Injectable biopolymer compositions and associated systems and methods are disclosed herein. In some embodiments, a biopolymer composition for treating an aneurysm is provided. The biopolymer composition can include an injectable hydrogel including: a biopolymer; a chemical cross-linker forming covalent bonds with the biopolymer; and a stabilizer configured to inhibit ex vivo precipitation of the biopolymer. The injectable hydrogel can have an ex vivo storage modulus of at least 100 Pa at 37° C. over a linear viscoelastic region of the injectable hydrogel. The ex vivo storage modulus can be greater than an ex vivo loss modulus of the injectable hydrogel over the linear viscoelastic region of the injectable hydrogel.

16 Claims, 28 Drawing Sheets

(56) References Cited

U.S. PATENT DOCUMENTS

| | | | |
|---|---|---|---|
| 9,907,684 | B2 | 3/2018 | Connor et al. |
| 9,925,210 | B2 | 3/2018 | McCarthy et al. |
| 9,962,146 | B2 | 5/2018 | Hebert et al. |
| 10,028,745 | B2 | 7/2018 | Morsi |
| 10,517,986 | B2 | 12/2019 | Sherman et al. |
| 10,576,099 | B2 | 3/2020 | Li et al. |
| 10,632,143 | B2 | 4/2020 | McCarthy et al. |
| 11,813,282 | B2 | 11/2023 | Li et al. |
| 2001/0000797 | A1 | 5/2001 | Mazzocchi |
| 2001/0001835 | A1 | 5/2001 | Greene et al. |
| 2003/0018294 | A1 | 1/2003 | Cox |
| 2003/0028209 | A1 | 2/2003 | Teoh et al. |
| 2003/0040772 | A1 | 2/2003 | Hyodoh et al. |
| 2003/0065303 | A1 | 4/2003 | Wellman et al. |
| 2004/0167597 | A1 | 8/2004 | Costantino et al. |
| 2005/0089554 | A1* | 4/2005 | Cormier ............ A61M 37/0015 424/448 |
| 2005/0267511 | A1 | 12/2005 | Marks et al. |
| 2006/0064151 | A1 | 3/2006 | Guterman et al. |
| 2006/0155323 | A1 | 7/2006 | Porter et al. |
| 2006/0200234 | A1 | 9/2006 | Hines |
| 2006/0206199 | A1 | 9/2006 | Churchwell et al. |
| 2007/0014831 | A1 | 1/2007 | Sung et al. |
| 2007/0100426 | A1 | 5/2007 | Rudakov et al. |
| 2007/0175536 | A1 | 8/2007 | Monetti et al. |
| 2007/0191924 | A1 | 8/2007 | Rudakov |
| 2007/0198075 | A1 | 8/2007 | Levy |
| 2008/0069801 | A1* | 3/2008 | Lee ..................... A61K 38/06 514/1.2 |
| 2008/0281350 | A1 | 11/2008 | Sepetka et al. |
| 2010/0021545 | A1 | 1/2010 | Chaput et al. |
| 2010/0023048 | A1 | 1/2010 | Mach |
| 2010/0144895 | A1 | 6/2010 | Porter |
| 2010/0184720 | A1 | 7/2010 | Gavard et al. |
| 2011/0137405 | A1 | 6/2011 | Wilson et al. |
| 2012/0316632 | A1 | 12/2012 | Gao |
| 2013/0066357 | A1 | 3/2013 | Aboytes et al. |
| 2013/0073026 | A1 | 3/2013 | Russo et al. |
| 2013/0244972 | A1 | 9/2013 | Ben-Shalom et al. |
| 2013/0274866 | A1 | 10/2013 | Cox et al. |
| 2014/0012307 | A1 | 1/2014 | Franano et al. |
| 2014/0017210 | A1 | 1/2014 | Laurencin et al. |
| 2014/0058420 | A1 | 2/2014 | Hannes et al. |
| 2014/0135810 | A1 | 5/2014 | Divino et al. |
| 2014/0135811 | A1 | 5/2014 | Divino et al. |
| 2014/0135812 | A1 | 5/2014 | Divino et al. |
| 2014/0257360 | A1 | 9/2014 | Keillor |
| 2014/0316012 | A1 | 10/2014 | Freyman et al. |
| 2014/0371734 | A1 | 12/2014 | Truckai |
| 2014/0377187 | A1 | 12/2014 | Lerouge et al. |
| 2015/0216684 | A1 | 8/2015 | Enzmann et al. |
| 2015/0250628 | A1 | 9/2015 | Monstadt et al. |
| 2015/0313605 | A1 | 11/2015 | Griffin |
| 2015/0313737 | A1 | 11/2015 | Tippett et al. |
| 2015/0327843 | A1 | 11/2015 | Garrison |
| 2016/0022445 | A1 | 1/2016 | Ruvalcaba et al. |
| 2016/0066921 | A1 | 3/2016 | Seifert et al. |
| 2016/0082037 | A1* | 3/2016 | Kirsch ..................... A61L 2/14 428/402 |
| 2016/0135984 | A1 | 5/2016 | Rudakov et al. |
| 2016/0206320 | A1 | 7/2016 | Connor |
| 2016/0206321 | A1 | 7/2016 | Connor |
| 2016/0256170 | A1 | 9/2016 | Busold et al. |
| 2016/0296714 | A1 | 10/2016 | Mide et al. |
| 2017/0150971 | A1 | 6/2017 | Hines |
| 2017/0156734 | A1 | 6/2017 | Griffin |
| 2017/0156903 | A1 | 6/2017 | Shobayashi |
| 2017/0189035 | A1 | 7/2017 | Porter |
| 2017/0246340 | A1* | 8/2017 | Girdhar ................. A61L 24/108 |
| 2017/0266023 | A1 | 9/2017 | Thomas |
| 2017/0296466 | A1 | 10/2017 | Girdhar et al. |
| 2017/0312364 | A1 | 11/2017 | Bossy et al. |
| 2017/0340333 | A1 | 11/2017 | Badruddin et al. |
| 2017/0354421 | A1 | 12/2017 | Maguire et al. |
| 2017/0367708 | A1 | 12/2017 | Mayer et al. |
| 2018/0049859 | A1 | 2/2018 | Stoppenhagen et al. |
| 2018/0110797 | A1 | 4/2018 | Li et al. |
| 2018/0125686 | A1 | 5/2018 | Lu |
| 2018/0140305 | A1 | 5/2018 | Connor |
| 2018/0161185 | A1 | 6/2018 | Kresslein et al. |
| 2018/0193025 | A1 | 7/2018 | Walzman |
| 2018/0193026 | A1 | 7/2018 | Yang et al. |
| 2018/0206852 | A1 | 7/2018 | Moeller |
| 2019/0053811 | A1 | 2/2019 | Garza et al. |
| 2019/0223876 | A1 | 7/2019 | Badruddin et al. |
| 2019/0223881 | A1 | 7/2019 | Hewitt et al. |
| 2019/0343532 | A1 | 11/2019 | Divino et al. |
| 2020/0060965 | A1 | 2/2020 | Supper |
| 2020/0061099 | A1 | 2/2020 | Li et al. |
| 2020/0360419 | A1 | 11/2020 | McCarthy et al. |
| 2021/0022743 | A1 | 1/2021 | Delaney et al. |
| 2021/0128162 | A1 | 5/2021 | Rhee et al. |
| 2021/0128169 | A1 | 5/2021 | Li et al. |
| 2021/0129275 | A1 | 5/2021 | Nguyen et al. |
| 2021/0153872 | A1 | 5/2021 | Nguyen et al. |
| 2021/0196284 | A1 | 7/2021 | Gorochow et al. |
| 2021/0212698 | A1 | 7/2021 | Connor |
| 2022/0008082 | A1 | 1/2022 | Connor |
| 2024/0033281 | A1 | 2/2024 | Li et al. |

FOREIGN PATENT DOCUMENTS

| | | |
|---|---|---|
| EP | 1448607 B1 | 1/2011 |
| EP | 2566454 B1 | 3/2014 |
| EP | 2121026 B1 | 6/2017 |
| WO | 9905977 A1 | 2/1999 |
| WO | 03011151 A1 | 2/2003 |
| WO | 2011066962 A1 | 6/2011 |
| WO | 2014169708 A1 | 10/2014 |
| WO | 2016098057 A1 | 6/2016 |
| WO | 2017074411 A1 | 5/2017 |
| WO | 2018051187 A1 | 3/2018 |
| WO | 2020162764 A1 | 8/2020 |
| WO | 2020236917 A1 | 11/2020 |
| WO | 2020262817 A1 | 12/2020 |
| WO | 2021046389 A1 | 3/2021 |

OTHER PUBLICATIONS

Shive, Matthew S., et al., "BST-Cargel® treatment maintains cartilage repair superiority over microfracture at 5 years in a multicenter randomized controlled trial.", CARTILAGE, 6(2), 62-72. https://doi.org/10.1177/1947603514562064.

Supper, Stephanie, et al., "Chitosan/glucose 1-phosphate as new stable in situ forming depot system for controlled drug delivery", European Journal of Pharmaceutics and Biopharmaceutics, 88(2), 361-373. https://doi.org/10.1016/j.ejpb.2014.05.015.

Supper, Stephanie, et al., "Rheological Study of Chitosan/Polyol-phosphate Systems: Influence of the Polyol Part on the Thermo-Induced Gelation Mechanism", Langmuir, 29(32), 10229-10237. https://doi.org/10.1021/la401993q.

Barnett, et al., "Assessment of EmboGel—A Selectively Dissolvable Radiopaque Hydrogel for Embolic Applications", J Vasc Interv Radiol 2011; vol. 22, No. 2, Feb. 2011, pp. 203-211.

Berenstein, et al., "Treatment of Experimental Aneurysms With an Embolic-Containing Device and Liquid Embolic Agent: Feasibility and Angiographic and Histological Results", Neurosurgery, vol. 64, No. 2, Feb. 2009, pp. 367-373.

Brennecka, et al., "In vivo embolization of lateral wall aneurysms in canines using the liquid-to-solid gelling PPODA-QT polymer system: 6-month pilot study", Laboratory investigation, J Neurosurg, vol. 119,, Jul. 2013, pp. 228-238.

Jalani, et al., "Tough, In-Situ Thermogelling, Injectable Hydrogels for Biomedical Applications", Macromolecular Bioscience, 2014, 8 Pages.

Murayama, et al., "Endovascular Treatment of Experimental Aneurysms by Use of a Combination of Liquid Embolic Agents and Protective Devices", Experimental Aneurysms, AJNR Am J Neuroradiol, vol. 21, Oct. 2000, pp. 1726-1735.

(56) References Cited

OTHER PUBLICATIONS

Ning, et al., "Experimental study of temperature-sensitive chitosan/β-glycerophosphate embolic material in embolizing the basicranial rete mirabile in swines", Experimental and Therapeutic Medicine, vol. 10, Feb. 19, 2015, pp. 316-322.

Wang, et al., "In Vivo Assessment of Chitosan/β-Glycerophosphate as a New Liquid Embolic Agent", Interventional Neuroradiology, vol. 17, 2011, pp. 87-92.

Zhen, et al., "Embolization of aneurysm by chitosan-glycerophosphate-fibroblast tissue hydrogel, a tissue engineering material: experiment with rabbits", Natl Med J China, vol. 89, No. 11, Mar. 24, 2009, pp. 727-731.

* cited by examiner

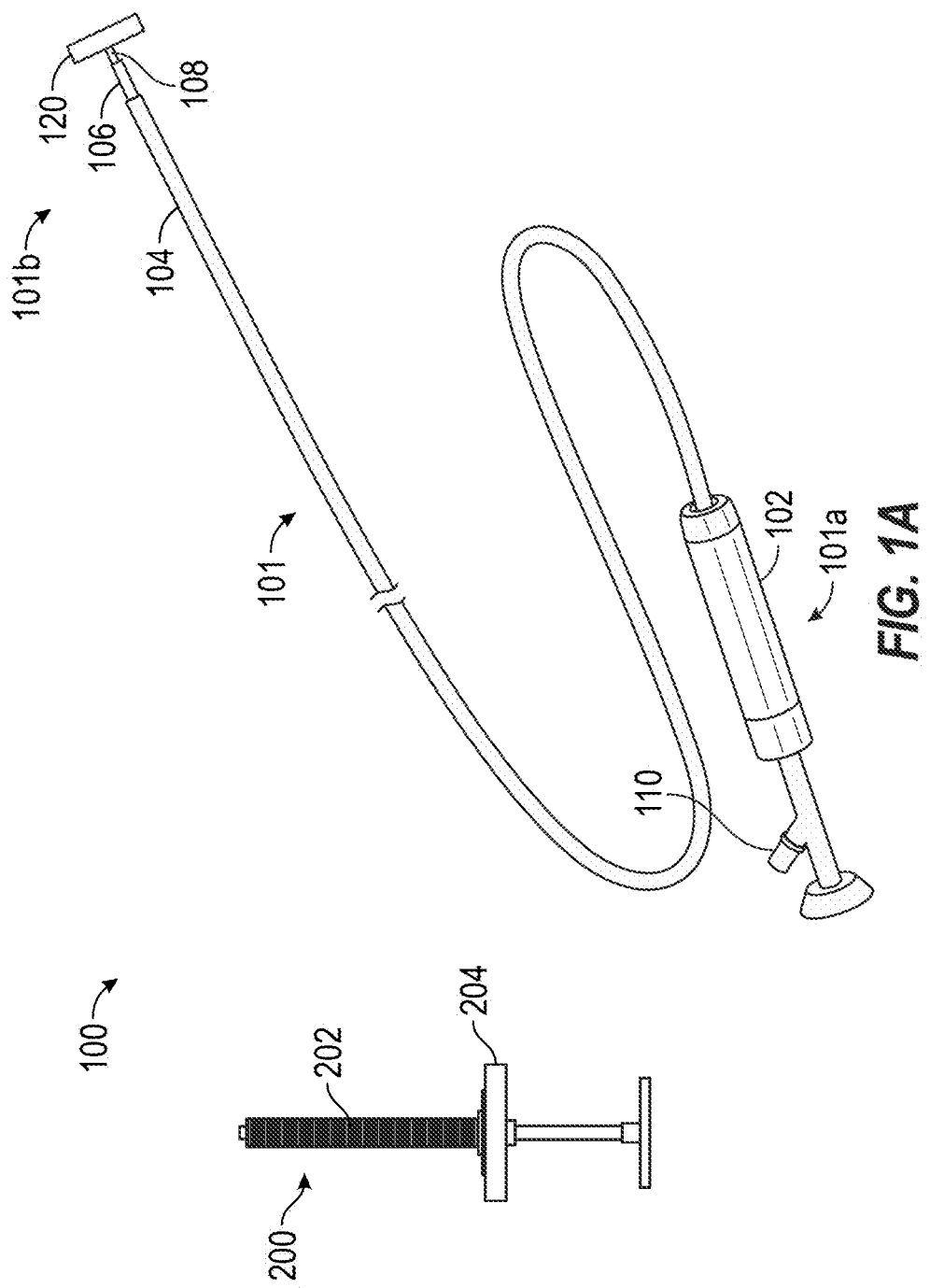

INJECTABLE BIOPOLYMER COMPOSITIONS AND ASSOCIATED SYSTEMS AND METHODS

CROSS-REFERENCE TO RELATED APPLICATION(S)

The present application claims the benefit of priority to U.S. Provisional Application No. 63/161,582, filed Mar. 16, 2021, and U.S. Provisional Application No. 63/161,597, filed Mar. 16, 2021, each of which is incorporated by reference herein in its entirety.

TECHNICAL FIELD

The present technology generally relates to biocompatible materials, and in particular, to biopolymer compositions configured for injection into a vascular defect or other treatment sites.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. These various aspects are provided as examples and do not limit the subject technology.

In one aspect of the present technology, a biopolymer composition for treating an aneurysm is provided. The biopolymer composition can include an injectable hydrogel including a biopolymer, a chemical crosslinker forming covalent bonds with the biopolymer, and a stabilizer configured to inhibit ex vivo precipitation of the biopolymer. The injectable hydrogel can have an ex vivo storage modulus of at least 100 Pa at 37° C. over a linear viscoelastic region of the injectable hydrogel.

In some embodiments, the injectable hydrogel is configured to occlude the aneurysm without undergoing a phase transition upon exposure to in vivo conditions.

In some embodiments, the biopolymer includes one or more of the following: chitosan, gelatin, collagen, fibrin, silk, starch, cellulose, agarose, dextran, alginate, hyaluronic acid, an extracellular matrix-derived polymer, poly(lactide), poly(glycolide), poly(lactide-co-glycolide), poly(caprolactone), poly(vinyl alcohol)), cellulose diacetete, or ethylene-vinyl alcohol copolymer. For example, the biopolymer can include chitosan. The chitosan can have a degree of deacetylation of at least 85%. The chitosan can have a viscosity of at least 50 Pa-s when measured as a 1% (w/v) solution at 20° C. and a shear rate of 1/s. The injectable hydrogel can include no more than 9% (w/v) of the biopolymer. The injectable hydrogel can include 2% (w/v) to 4% (w/v) of the biopolymer.

In some embodiments, the chemical crosslinker is configured to extend an in vivo biodegradation time of the injectable hydrogel. The in vivo biodegradation time can be at least 1 month or at least 3 months. The chemical crosslinker can include one or more of the following: genipin, glutaraldehyde, formaldehyde, diethyl squarate, blocked diisocyanate, ethylene glycol diglycidyl ether, a functionalized polyethylene glycol, a carbodiimide, an epoxide, a photosensitive crosslinker, an enzymatic crosslinker, or a polymer-based crosslinker. The injectable hydrogel can include no more than 1% (w/v) of the chemical crosslinker. The injectable hydrogel can include 0.005% (w/v) to 0.01% (w/v) of the chemical crosslinker.

In some embodiments, the stabilizer is configured to inhibit ex vivo precipitation of the biopolymer over a period of at least 1 month. The stabilizer can be configured to inhibit ex vivo precipitation of the biopolymer over a period of at least 6 months. The stabilizer can be configured to form an interpenetrating network with the biopolymer. The stabilizer can be configured to space apart hydrophobic groups on the biopolymer. The stabilizer can be configured to inhibit ex vivo precipitation of the biopolymer after the injectable hydrogel has undergone heat sterilization. The stabilizer can be nonionic.

In some embodiments, the stabilizer includes a polysaccharide. The polysaccharide can include a cellulose derivative. The cellulose derivative can be hydroxyethyl cellulose. The stabilizer can have a viscosity of at least 2000 Pa-s when measured as a 1% (w/v) solution at 20° C. and a shear rate of 1/s. The injectable hydrogel can include no more than 5% (w/v) of the stabilizer. The injectable hydrogel can include 0.5% (w/v) to 3% (w/v) of the stabilizer.

In some embodiments, the stabilizer includes a contrast agent. The contrast agent can be iohexol. The injectable hydrogel can include at least 30% (w/v) of the stabilizer. The injectable hydrogel can include 50% (w/v) to 70% (w/v) of the stabilizer.

In some embodiments, the injectable hydrogel includes a physical crosslinker forming noncovalent interactions with the biopolymer. The noncovalent interactions can include one or more of ionic bonding, hydrogen bonding, Van der Waals interactions, or hydrophobic interactions. The biopolymer can include a plurality of charged groups, and the physical crosslinkers can be configured to shield at least some of the charged groups. The biopolymer can be cationic and the physical crosslinker can be anionic. The physical crosslinker can include β-glycerophosphate. The injectable hydrogel can include no more than 5% (w/v) of the physical crosslinker. The injectable hydrogel can include 0.5% (w/v) to 2% (w/v) of the physical crosslinker.

In some embodiments, the injectable hydrogel does not include a physical crosslinker.

In some embodiments, the injectable hydrogel includes a contrast agent. The contrast agent can include one or more of the following: iohexol, iodixanol, iopamidol, diatrizoate, iothalamate, iopromide, ioversol, ioxilan, iothalamate/meglumine, ioxaglate/meglumine, diatrizoate/meglumine, iodomide sodium, or metrizamide.

In another aspect of the present technology, a biopolymer composition for treating an aneurysm is provided. The biopolymer composition can include an injectable hydrogel including a biopolymer, a chemical crosslinker forming covalent bonds with the biopolymer, and a stabilizer configured to inhibit ex vivo phase separation of the biopolymer. The injectable hydrogel can include an ex vivo storage modulus that is greater than an ex vivo loss modulus of the injectable hydrogel over a linear viscoelastic region of the injectable hydrogel.

In some embodiments, the ex vivo storage modulus is at least 100 Pa at 37° C. over the linear viscoelastic region of the injectable hydrogel.

In some embodiments, the injectable hydrogel has a preformed, ex vivo state that is configured to be stable at room temperature over a storage period of at least 1 month. The ex vivo storage modulus of the injectable hydrogel can vary by no more than 25% over the storage period. In the preformed, ex vivo state, the injectable hydrogel can form a cohesive viscoelastic solid. The storage period can be at least 1 year.

In some embodiments, the injectable hydrogel is configured to occlude the aneurysm without undergoing a phase transition upon exposure to in vivo conditions.

In some embodiments, the biopolymer includes a polysaccharide. The polysaccharide can include chitosan. The chitosan can have a degree of deacetylation of at least 85%. The chitosan can have a viscosity of at least 50 Pa-s when measured as a 1% (w/v) solution at 20° C. and a shear rate of 1/s. The injectable hydrogel can include 2% (w/v) to 4% (w/v) of the biopolymer.

In some embodiments, the chemical crosslinker is configured to extend an in vivo biodegradation time of the injectable hydrogel. The in vivo biodegradation time can be at least 1 month. The chemical crosslinker can include one or more of the following: genipin, glutaraldehyde, formaldehyde, diethyl squarate, blocked diisocyanate, ethylene glycol diglycidyl ether, a functionalized polyethylene glycol, a carbodiimide, an epoxide, a photosensitive crosslinker, an enzymatic crosslinker, or a polymer-based crosslinker. The injectable hydrogel can include 0.005% (w/v) to 0.01% (w/v) of the chemical crosslinker.

In some embodiments, the stabilizer is configured to form an interpenetrating network with the biopolymer. The stabilizer can be configured to space apart hydrophobic groups on the biopolymer. The stabilizer can be configured to inhibit ex vivo phase separation of the biopolymer after the injectable hydrogel has undergone heat sterilization. The stabilizer can be nonionic.

In some embodiments, the stabilizer includes a polysaccharide. The polysaccharide can be hydroxyethyl cellulose. The stabilizer can have a viscosity of at least 2000 Pa-s when measured as a 1% (w/v) solution at 20° C. and a shear rate of 1/s. The injectable hydrogel can include 0.5% (w/v) to 3% (w/v) of the stabilizer.

In some embodiments, the stabilizer includes a contrast agent. The contrast agent can be iohexol. The injectable hydrogel can include 50% (w/v) to 70% (w/v) of the stabilizer.

In some embodiments, the injectable hydrogel includes a physical crosslinker forming noncovalent interactions with the biopolymer. The noncovalent interactions can include one or more of ionic bonding, hydrogen bonding, Van der Waals interactions, or hydrophobic interactions. The physical crosslinker can include 3-glycerophosphate. The injectable hydrogel can include 0.5% (w/v) to 2% (w/v) of the physical crosslinker.

In some embodiments, the injectable hydrogel includes a contrast agent. The contrast agent can include one or more of the following: iohexol, iodixanol, iopamidol, diatrizoate, iothalamate, iopromide, ioversol, ioxilan, iothalamate/meglumine, ioxaglate/meglumine, diatrizoate/meglumine, iodomide sodium, or metrizamide.

In a further aspect of the present technology, a system for treating an aneurysm is provided. The system can include a sterilized container including the biopolymer composition of any of the embodiments described herein. The system can further include a neck cover configured to be positioned within the aneurysm. The neck cover can be configured to inhibit leakage of the biopolymer composition out of the aneurysm. The system can further include an elongated shaft configured to deliver the biopolymer composition into the aneurysm. The system can further include an injector configured to fluidly couple to the elongated shaft.

In yet another aspect of the present technology, a method for treating an aneurysm of a patient is provided. The method can include providing a preformed hydrogel comprising a biopolymer, a chemical crosslinker, and a stabilizer. The preformed hydrogel can include an ex vivo storage modulus of at least 100 Pa at 37° C. over a linear viscoelastic region of the preformed hydrogel. The method can include injecting the preformed hydrogel into the aneurysm via an elongated shaft positioned within the patient's vasculature.

In some embodiments, the preformed hydrogel does not undergo a phase transition after being injected into the aneurysm. The preformed hydrogel can be configured to be stable at room temperature over a storage period of at least 1 month. The preformed hydrogel can be provided in a sterilized container. The preformed hydrogel can be provided without mixing of precursor components within 30 minutes before the preformed hydrogel is injected into the aneurysm.

In some embodiments, the method further includes positioning a neck cover within the aneurysm before injecting the preformed hydrogel, and inhibiting leaking of the preformed hydrogel into a parent vessel of the aneurysm via the neck cover. The neck cover can at least partially occlude a neck of the aneurysm. The preformed hydrogel can be injected into a space between the neck cover and a dome of the aneurysm. The neck cover can be coupled to the elongated shaft. The method can further include detaching the neck cover from the elongated shaft, after the preformed hydrogel has been injected into the aneurysm.

In some embodiments, the biopolymer includes a polysaccharide. The polysaccharide can include chitosan. The chitosan can have a viscosity of at least 50 Pa-s when measured as a 1% (w/v) solution at 20° C. and a shear rate of 1/s. The preformed hydrogel can include 2% (w/v) to 4% (w/v) of the biopolymer.

In some embodiments, the chemical crosslinker is configured to extend an in vivo biodegradation time of the preformed hydrogel. The chemical crosslinker can include genipin. The preformed hydrogel can include 0.005% (w/v) to 0.01% (w/v) of the chemical crosslinker.

In some embodiments, the stabilizer is configured to inhibit ex vivo precipitation of the biopolymer over a storage period of at least 1 month. The stabilizer can be configured to form an interpenetrating network with the biopolymer. The stabilizer can be configured to space apart hydrophobic groups on the biopolymer. The stabilizer can be configured to inhibit ex vivo precipitation of the biopolymer after the preformed hydrogel has undergone heat sterilization.

In some embodiments, the stabilizer includes a polysaccharide. The polysaccharide can include hydroxyethyl cellulose. The hydroxyethyl cellulose can have a viscosity of at least 2000 Pa-s when measured as a 1% (w/v) solution at 20° C. and a shear rate of 1/s. The preformed hydrogel can include 0.5% (w/v) to 3% (w/v) of the polysaccharide.

In some embodiments, the stabilizer includes a contrast agent. The contrast agent can be iohexol. The preformed hydrogel can include 50% (w/v) to 70% (w/v) of the contrast agent.

In some embodiments, the preformed hydrogel includes a physical crosslinker forming noncovalent interactions with the biopolymer. The physical crosslinker can include β-glycerophosphate. The preformed hydrogel can include 0.5% (w/v) to 2% (w/v) of the physical crosslinker.

In some embodiments, the injectable hydrogel includes a contrast agent.

In some embodiments, the ex vivo storage modulus is greater than an ex vivo loss modulus of the injectable hydrogel over the linear viscoelastic region.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 1A is a partially schematic view of a treatment system configured in accordance with embodiments of the present technology.

DETAILED DESCRIPTION

Figure 1B:
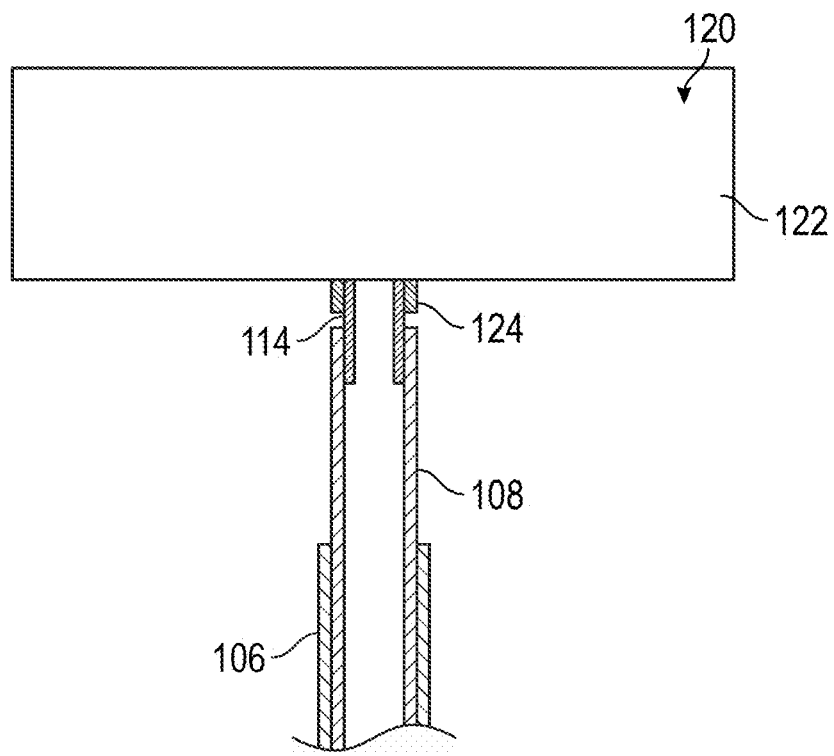
FIG. 1B is an enlarged cross-sectional view of a distal portion of the treatment system of FIG. 1A.

The present technology relates to biopolymer compositions and associated systems and methods. In some embodiments, for example, a biopolymer composition for treating an aneurysm is provided. The biopolymer composition can include an injectable hydrogel formed from some or all of the following components: a biopolymer, a chemical crosslinker forming covalent bonds with the biopolymer, a physical crosslinker forming noncovalent interactions with the biopolymer, a stabilizer configured to inhibit ex vivo precipitation of the biopolymer, a contrast agent, and/or a solvent. The injectable hydrogel can be a cohesive, viscoelastic solid that is provided in a preformed, ex vivo state that is ready for use in occluding the aneurysm, e.g., without undergoing a phase transition (e.g., a temperature- or pH-triggered phase transition), undergoing additional crosslinking, and/or requiring any mixing of precursor components before use. For example, the injectable hydrogel can exhibit an ex vivo storage modulus of at least 100 Pa at 37° C. over a linear viscoelastic region of the injectable hydrogel. The ex vivo storage modulus can be a greater than an ex vivo loss modulus of the injectable hydrogel over the linear viscoelastic region.

In some embodiments, the methods described herein include delivering the biopolymer composition into the aneurysm sac. The biopolymer composition can provide a complete or nearly complete volumetric filling of the internal volume of an aneurysm, and/or a complete or nearly complete coverage of the neck of the aneurysm with new endothelial tissue. These features, among others, can lead to a lower recanalization rate than that of platinum coil treatments and faster aneurysm occlusion than that of flow diverters. Additionally, the biopolymer compositions can be configured to biodegrade over time and thereby have little or no long-term mass effect. Furthermore, the biopolymer composition can be configured to have diminishing radiopacity to reduce interference with future CT and MRI imaging and procedures.

The present technology can provide many advantages over conventional approaches for aneurysm treatment. For example, conventional treatment methods typically use either a low viscosity embolic agent that gels or solidifies in situ when exposed to physiological conditions at the treatment site, or separate precursor components that are mixed immediately before delivery to form the final embolic agent. However, these approaches may present challenges with long-term storage stability, require additional process steps, and/or introduce timing complications. For example, if the agent gels too quickly, it may clog the delivery device. If the agent gels too slowly, it may leak out of the treatment site, which can have catastrophic results in certain applications such as the treatment of cerebral aneurysms.

In contrast, the biopolymer compositions of the present technology can form an injectable hydrogel that can be pre-mixed, heat-sterilized, and stored for extended periods. Embodiments of the disclosed biopolymer compositions can thus be supplied in a ready-to-use form. The biopolymer compositions can be removed under sterile conditions from its packaging and immediately introduced into a catheter at any desired time during an aneurysm treatment procedure, and without the need to carry out any preliminary mixing or standing steps prior to such introduction. This approach can improve the reliability, convenience, and efficacy of the treatment procedure.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

I. OVERVIEW OF TREATMENT SYSTEMS AND METHODS

FIG. 1A shows a treatment system 100 ("system 100") configured in accordance with embodiments of the present technology. Although the system 100 is described herein in the context of treating aneurysms such as cerebral aneurysms, this is not intended to be limiting, and the system 100 can also be used in the treatment of other types of vascular defects, and/or in any other application involving delivery of a biopolymer composition into a space within a patient's body.

As shown in FIG. 1A, the system 100 comprises a delivery system 101, a neck cover 120 (also referred to herein as an "occlusive member," "occlusive device," or a "neck protection device"), and an embolic kit 200. The neck cover 120 (shown schematically) is configured to be detachably coupled to the delivery system 101, and the delivery system 101 is configured to intravascularly position the neck cover 120 within an aneurysm. Representative examples of neck covers suitable for use with the system 100 are described in U.S. Pat. Nos. 8,142,456, 9,855,051, 10,327,781, U.S. Patent Application Publication No. 2020/0187953, U.S. Patent Application Publication No. 2021/0128169, and U.S. Patent Application Publication No. 2021/0153872, the disclosures of which are incorporated by reference herein in their entirety.

The embolic kit 200 comprises a biopolymer composition 202 (e.g., an embolic composition) and an injector 204 configured to be fluidly coupled to a proximal portion of the delivery system 101 for injection of the biopolymer composition 202 into the aneurysm cavity. The biopolymer composition 202 can be delivered to a space between the neck cover 120 and the dome of the aneurysm to fill and occlude the aneurysm cavity. The neck cover 120 prevents migration of the biopolymer composition 202 into the parent vessel, and together the neck cover 120 and biopolymer composition 202 prevent blood from flowing into the aneurysm. As described in greater detail below, bioabsorption of the biopolymer composition 202 and endothelialization of the neck cover 120 cause the aneurysm wall to fully degrade, leaving behind a successfully remodeled (aneurysm free) region of the blood vessel.

As shown in FIG. 1A, the delivery system 101 has a proximal portion 101a configured to be extracorporeally positioned during treatment and a distal portion 101b configured to be intravascularly positioned at or within an aneurysm. The delivery system 101 may include a handle 102 at the proximal portion 101a and a plurality of elongated shafts extending between the handle 102 and the distal portion 101b. In some embodiments, for example as shown in FIG. 1A, the delivery system 101 may include a first elongated shaft 104 (such as a guide catheter or balloon guide catheter), a second elongated shaft 106 (such as a microcatheter) configured to be slidably disposed within a lumen of the first elongated shaft 104, and a third elongated shaft 108 configured to be slidably disposed within a lumen of the second elongated shaft 106. The delivery system 101 and/or the third elongated shaft 108 is configured to be detachably coupled at its distal end portion to the neck cover 120 via a connector 124 (see FIG. 1B) of the neck cover 120. In some embodiments, the delivery system 101 does not include the first elongated shaft 104.

The second elongated shaft 106 is generally constructed to track over a conventional guidewire in the cervical anatomy and into the cerebral vessels associated with the brain. The second elongated shaft 106 may also be chosen according to several standard designs that are generally available. For example, the second elongated shaft 106 can have a length that is at least 125 cm long, and more particularly may be between about 125 cm and about 175 cm long. The lumen of the second elongated shaft 106 is configured to slidably receive the neck cover 120 in a radially constrained state. The second elongated shaft 106 can have an inner diameter less than or equal to 0.006 inches (0.015 cm), 0.011 inches (0.028 cm), 0.015 inches (0.038 cm), 0.017 inches (0.043 cm), 0.021 inches (0.053 cm), or 0.027 inches (0.069 cm).

The third elongated shaft 108 can be movable within the first and/or second elongated shafts 104, 106 to position the neck cover 120 at a desired location. The third elongated shaft 108 can be sufficiently flexible to enable manipulation, e.g., advancement and/or retraction, of the neck cover 120 through tortuous passages. Tortuous passages can include, for example, catheter lumens, microcatheter lumens, blood vessels, urinary tracts, biliary tracts, and airways. The third elongated shaft 108 can be formed of any material and in any dimensions suitable for the task(s) for which the system 100 is to be employed. In some embodiments, at least the distal portion of the third elongated shaft 108 can comprise a flexible metal hypotube. The hypotube, for example, can be laser cut along all or a portion of its length to impart increased flexibility. In some embodiments, the third elongated shaft 108 can be surrounded over some or all of its length by a lubricious coating, such as polytetrafluoroethylene (PTFE). The third elongated shaft 108 can have an inner diameter less than or equal to 0.006 inches (0.015 cm), 0.011 inches (0.028 cm), 0.015 inches (0.038 cm), 0.017 inches (0.043 cm), 0.021 inches (0.053 cm), or 0.027 inches (0.069 cm)

Referring still to FIGS. 1A and 1B, the biopolymer composition 202 may be preloaded into the injector 204 (as shown), or at least some of the biopolymer composition 202 may be provided separately. The biopolymer composition 202 can be any material suitable for forming a solid or semi-solid, viscoelastic structure (e.g., a hydrogel) that partially or completely occludes the interior cavity of the aneurysm. In some embodiments, the biopolymer composition 202 is a preformed composition that is ready for use without any mixing of precursor materials. The biopolymer composition 202 can be a highly viscous material that is sufficiently solid to fill and occlude the aneurysm in its preformed state, and without requiring further steps (e.g., chemical reactions, physical interactions) and/or changes in material properties (e.g., viscosity, degree of crosslinking) to effectively occlude the aneurysm. Additional details of the biopolymer composition 202 are provided in Section II below.

The injector 204 can be configured to pressurize the biopolymer composition 202 to a pressure that is sufficiently high to push the highly viscous biopolymer composition 202 through the components of the delivery system 101 (e.g., through the lumen of the third elongated shaft 108). For example, the injector 204 can be configured to generate and withstand a pressure of at least 4,000 psi, 5,000 psi, 6,000 psi, 7,000 psi, 8000, psi, 9,000 psi, 10,000 psi, 11,000 psi, 12,000 psi, 13,000 psi, 14,000 psi, 15,000 psi, or higher. Representative examples of injectors suitable for use with the present technology are described in U.S. Provisional Application No. 63/266,351, filed Jan. 3, 2022, the disclosure of which is incorporated by reference herein in its entirety.

Figure 2A:
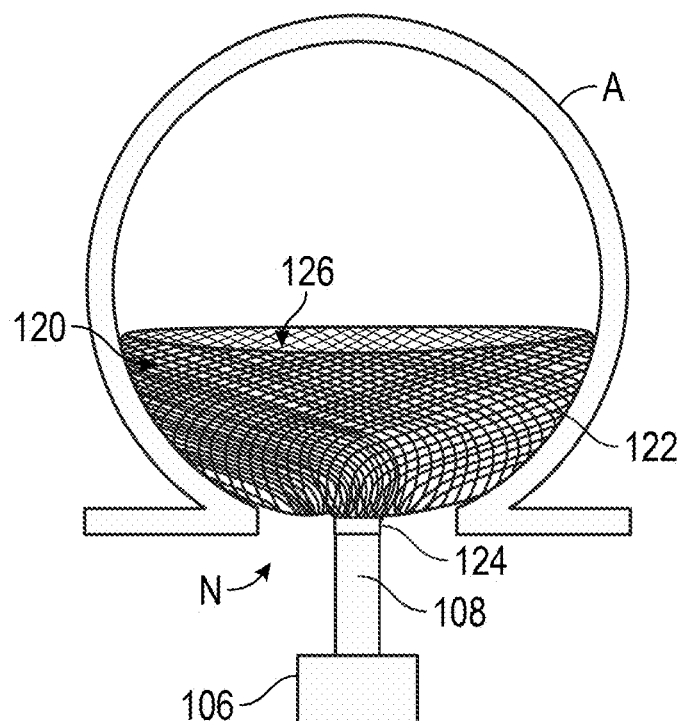
FIGS. 2A-2E show an example method of treating an aneurysm using the treatment system of FIGS. 1A and 1B, in accordance with embodiments of the present technology.

The system 100 can further include a conduit configured to guide the biopolymer composition 202 delivered from the injector 204 to a space between at least a portion of the neck cover 120 and the aneurysm dome. In some embodiments, the conduit is incorporated into the delivery system 101. For example, as depicted in the enlarged cross-sectional view of the distal portion 101b shown in FIG. 1B, the conduit can comprise a combination of the third elongated shaft 108 and an extension 114 fixed to a distal end portion of the third elongated shaft 108. The extension 114 can be a tubular member that extends distally from the third elongated shaft 108, through the connector 124, and through the neck cover 120, at least when the neck cover 120 is in an expanded state. When the neck cover 120 is collapsed within the lumen of the third elongated shaft 108 during delivery, a portion of the neck cover 120 may extend distally of the extension 114. The length of the extension 114 can be such that, when the distal portion 101b of the delivery system 101 is positioned at the aneurysm with the neck cover 120 in an expanded state (for example, as shown in FIG. 2A), a distal terminus of the extension 114 is even with the distal end of the connector 124, distal of the connector 124 but proximal of a distal end of the neck cover 120, or even with or distal of the distal end of the neck cover 120. It may be beneficial for the extension 114 to be as short as possible to ensure the extension 114 remains sufficiently spaced apart from the fragile aneurysm wall.

In some embodiments, the extension 114 comprises an atraumatic member, such as a soft, flexible coil. In other embodiments, the extension 114 comprises a flexible tube having a continuous sidewall (i.e., not formed of a coiled member). In any case, a distal end portion of the injector 204 can be fluidly coupled to a proximal end portion of the third elongated shaft 108 via a port 110. The port 110 can be located at the proximal portion 101a of the delivery system 101, such as on or proximal to the handle 102. The pressure generated at the injector 204 can cause the biopolymer composition 202 to flow through the lumen of the third elongated shaft 108, through the lumen of the extension 114, and into the aneurysm cavity. Once the biopolymer composition 202 has sufficiently filled the aneurysm cavity, the neck cover 120 and extension 114 can be detached via electrolytic detachment that severs a region of the extension 114 exposed between the third elongated shaft 108 and the neck cover 120.

According to several embodiments, the conduit may comprise an additional elongated shaft (not shown). The additional elongated shaft can be delivered to the aneurysm through one or more of the first, second, and/or third elongated shafts 104, 106, 108, or may be delivered separately (i.e., outside of) the delivery system 101. In such embodiments, a proximal end portion of the elongated shaft is configured to be fluidly coupled to the injector 204 via the port 110. Methods for delivering the biopolymer composition 202 through a separate elongated shaft are discussed below.

The neck cover 120 may comprise an expandable element having a low-profile or constrained state while positioned within a catheter (such as the second elongated shaft 106) for delivery to the aneurysm and an expanded, deployed state for positioning within the aneurysm. In some embodiments the neck cover 120 comprises a mesh 122 (shown schematically in FIG. 1B) and a connector 124 coupled to the mesh 122. The connector 124 is configured to be coupled to one or more components of the delivery system 101, such as the third elongated shaft 108 and/or extension 114. The mesh 122 can be formed of a resilient material and shape set such that upon exiting the second elongated shaft 106, the mesh 122 self-expands to a predetermined shape. The mesh 122 can have any shape or size in the expanded state that enables the mesh 122 to cover the aneurysm neck. In some embodiments, for example as shown in FIG. 2A, the mesh 122 can be configured to assume a bowl shape. Other shapes are possible. The mesh 122 has a porosity sufficient to prevent leakage of the biopolymer composition 202 into the parent vessel.

In some embodiments, the mesh 122 is formed of a plurality of braided filaments that have been heat-set to assume a predetermined shape when released from the constraints of the delivery catheter. The mesh 122 may be formed of metal wires, polymer wires, or both, and the wires may have shape memory and/or superelastic properties. The mesh 122 may be formed of 24, 32, 36, 48, 64, 72, 96, 128, or 144 filaments. The mesh 122 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 122 may have the same diameter. For example, in some embodiments, all of the filaments have a diameter of no more than 0.001 inches. In some embodiments, some of the filaments may have different cross-sectional diameters. For example, some of the filaments may have a slightly thicker diameter to impart additional strength to the braid. In some embodiments, some of the filaments can have a diameter of no more than 0.001 inches, and some of the filaments can have a diameter of greater than 0.001 inches. The thicker filaments may impart greater strength to the braid without significantly increasing the device delivery profile, with the thinner wires offering some strength while filling out the braid matrix density.

In some embodiments, the mesh 122 can be a non-braided structure, such as a laser-cut stent. Moreover, while the mesh 122 shown in FIGS. 2A-2D is a dual-layer mesh, in some embodiments the mesh 122 may comprise more or fewer layers (e.g., a single layer, three layers, four layers, etc.).

A physician may begin by intravascularly advancing the second elongated shaft 106 towards an intracranial aneurysm A with the neck cover 120 in a low-profile, collapsed state and coupled to a distal end portion of the third elongated shaft 108. A distal portion of the second elongated shaft 106 may be advanced through a neck N of the aneurysm A to locate a distal opening of the second elongated shaft 106 within an interior cavity of the aneurysm A. The third elongated shaft 108 may be advanced distally relative to the second elongated shaft 106 to push the neck cover 120 through the opening at the distal end of the second elongated shaft 106, thereby releasing the neck cover 120 from the shaft 108 and enabling the neck cover 120 to self-expand into an expanded, deployed state.

FIG. 2A shows the neck cover 120 in an expanded, deployed state, positioned in an aneurysm cavity and still coupled to the third elongated shaft 108. In the expanded, deployed state, the neck cover 120 may generally conform to the curved inner surface of the aneurysm A. In some embodiments the neck cover 120 assumes a predetermined shape that is concave towards the aneurysm dome and encloses an interior region 126.

Figure 2B:
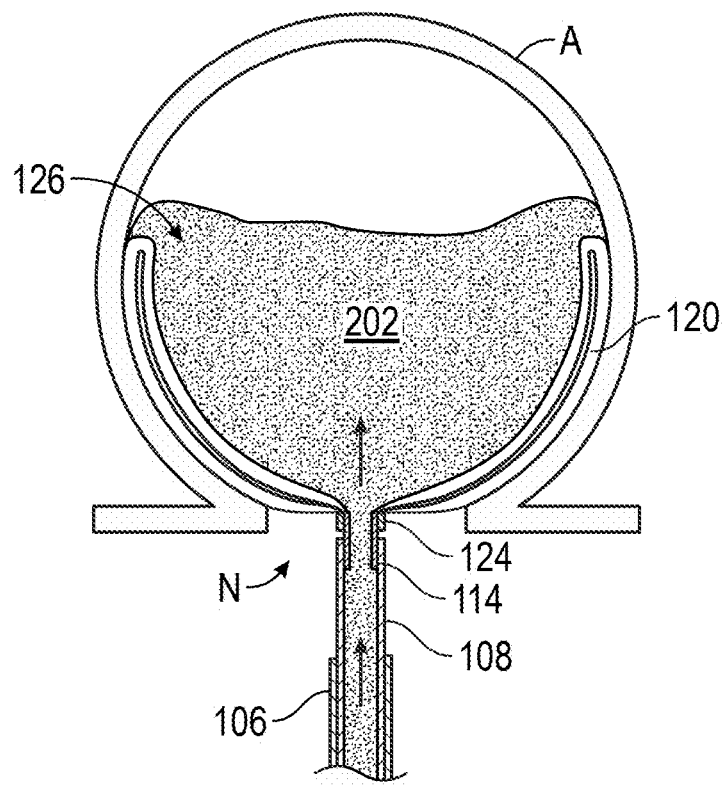

As illustrated in FIG. 2B, the biopolymer composition 202 can be injected through the third elongated shaft 108 and extension 114 to a space between the neck cover 120 and an inner surface of the aneurysm wall. In other embodiments, the biopolymer composition 202 can be delivered through another elongated shaft (not shown) separate from the third elongated shaft 108 and extension 114. As additional biopolymer composition 202 is delivered, it fills the interior region 126 and all or a portion of the volume of the aneurysm cavity. It is beneficial to fill as much space in the aneurysm as possible, as leaving voids within the aneurysm sac may cause delayed healing and increased risk of aneurysm recanalization and/or rupture. While the scaffolding provided by the neck cover 120 across the neck helps thrombosis of blood form in any gaps and healing at the neck N, the substantial filling of the cavity prevents rupture acutely and does not rely on the neck cover 120. In some embodiments, the biopolymer composition 202 may fill greater than 40%, 50%, 60%, 65%, 70%, 75%, 80%, 85%, or 90% of the aneurysm sac volume.

Figure 2C:
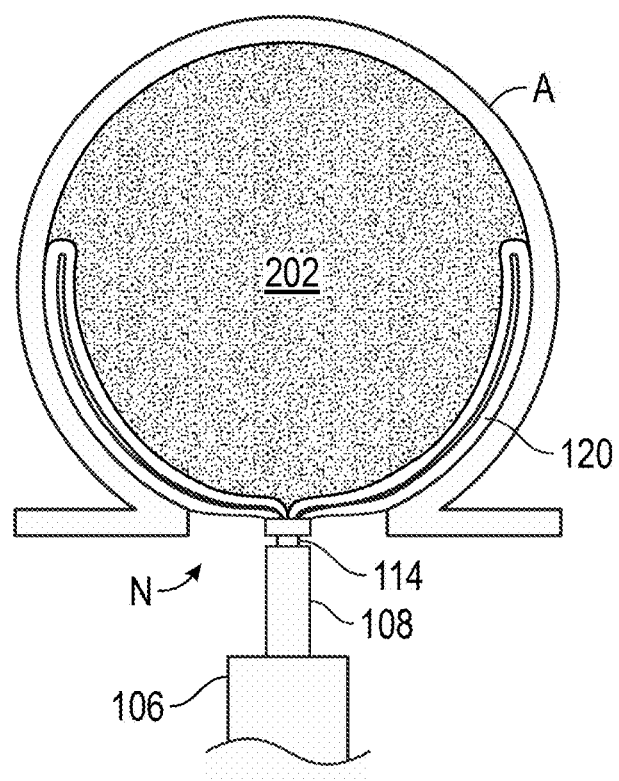

FIG. 2C is a cross-sectional view of the neck cover 120 still attached to the delivery system just after completion of delivery of the biopolymer composition 202. During and after delivery, the biopolymer composition 202 exerts a substantially uniform downward pressure (i.e., towards the parent vessel) on the neck cover 120 that further seals and stabilizes the neck cover 120 around the neck N of the aneurysm A. Moreover, the biopolymer composition 202 along the distal wall 132 provides additional occlusion. In some embodiments, the biopolymer composition 202 completely or substantially completely occludes the pores of the adjacent layer or wall of the neck cover 120 such that blood cannot flow past the biopolymer composition 202 into the aneurysm cavity. It is desirable to occlude as much of the aneurysm as possible, as leaving voids of gaps can enable blood to flow in and/or pool, which may continue to stretch out the walls of aneurysm A. Dilation of the aneurysm A can lead to recanalization and/or herniation of the neck cover 120 and/or biopolymer composition 202 into the parent vessel and/or may cause the aneurysm A to rupture. Both conditions can be fatal to the patient.

Figure 2D:
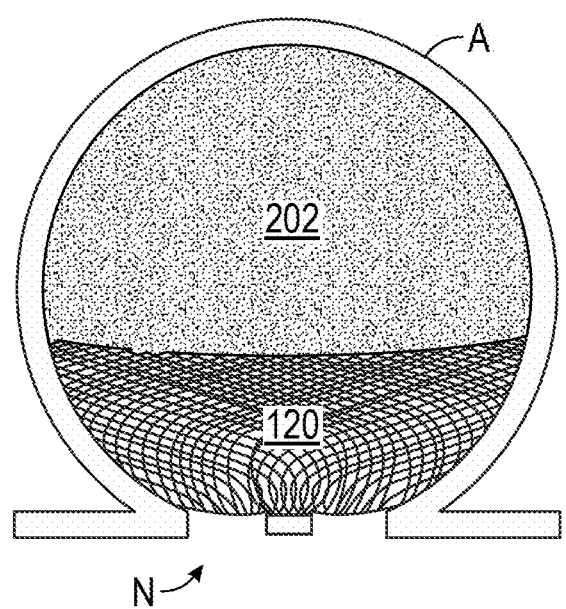

As shown in FIG. 2D, once delivery of the biopolymer composition 202 is complete, the delivery system 101 and/or third elongated shaft 108 can be detached from the neck cover 120 (electrolytically or mechanically) and withdrawn from the patient's body. In those embodiments comprising a separate elongated shaft for delivering the biopolymer composition 202, the elongated shaft can be withdrawn before, during, or after detachment of the third elongated shaft 108 from the neck cover 120.

Over time natural vascular remodeling mechanisms and/or bioabsorption of the biopolymer composition 202 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments of the neck cover 120. Eventually, the thrombus and the cells at the wall of the aneurysm may fully degrade, leaving behind a successfully remodeled region of the blood vessel.

In some embodiments, contrast agent can be delivered during advancement of the neck cover 120 and/or biopolymer composition 202 in the vasculature, deployment of the neck cover 120 and/or biopolymer composition 202 at the aneurysm A, and/or after deployment of the neck cover 120 and/or biopolymer composition 202 prior to initiation of withdrawal of the delivery system. The contrast agent can be delivered through the second elongated shaft 106, the conduit, or through another catheter or device commonly used to deliver contrast agent. The aneurysm (and devices therein) may be imaged before, during, and/or after injection of the contrast agent, and the images may be compared to confirm a degree of occlusion of the aneurysm.

Figure 2E:
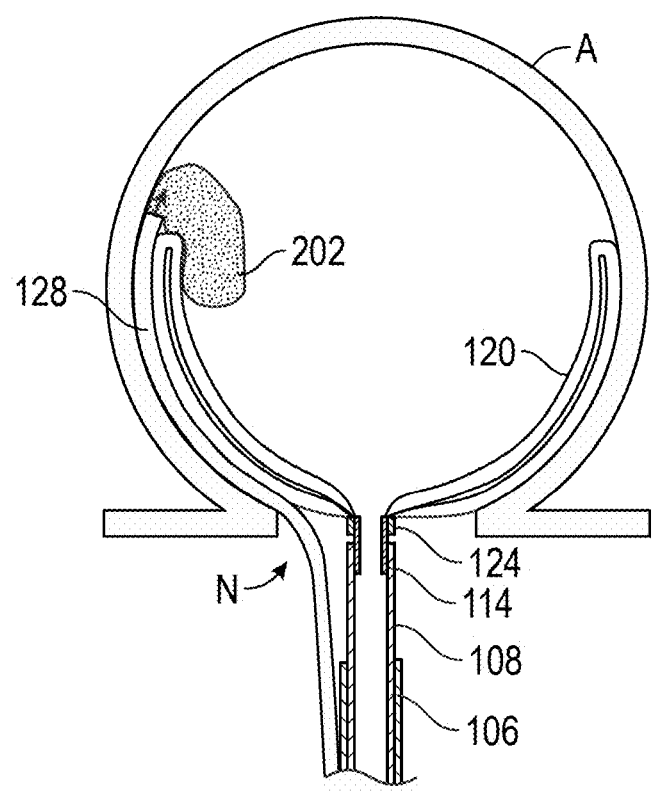

As shown in FIG. 2E, in some embodiments, the system 100 may comprise two separate elongated shafts (e.g., microcatheters), with one elongated shaft dedicated to delivery of the biopolymer composition 202 (e.g., a fourth elongated shaft 128), and the other elongated shaft dedicated to the delivery of the neck cover 120 (e.g., the third elongated shaft 108). In such embodiments, the fourth elongated shaft 128 can be fluidly coupled to the injector 204 to form at least part of the conduit for conveying the biopolymer composition 202 into the aneurysm A. The fourth elongated shaft 128 may be intravascularly advanced to the aneurysm A and through the neck N such that that a distal tip of the fourth elongated shaft 128 is positioned within the aneurysm cavity. In some embodiments, the fourth elongated shaft 128 may be positioned within the aneurysm cavity such that the distal tip of the shaft 128 is near the dome of the aneurysm A.

The third elongated shaft 108 containing the neck cover 120 may be intravascularly advanced to the aneurysm A and positioned within the aneurysm cavity adjacent the fourth elongated shaft 128. The neck cover 120 may then be deployed within the aneurysm sac. As the neck cover 120 is deployed, it pushes the fourth elongated shaft 128 outwardly towards the side of the aneurysm A, and when fully deployed the neck cover 120 holds or "jails" the fourth elongated shaft 128 between an outer surface of the neck cover 120 and the inner surface of the aneurysm wall.

The biopolymer composition 202 may then be delivered through the fourth elongated shaft 128 to a position between the inner surface of the aneurysm wall and the outer surface of the neck cover 120. For this reason, it may be beneficial to initially position the distal tip of the fourth elongated shaft 128 near the dome (or more distal surface) of the aneurysm wall. This way, the "jailed" fourth elongated shaft 128 will be secured by the neck cover 120 such that the biopolymer composition 202 gradually fills the open space in the aneurysm sac between the dome and the neck cover 120.

II. BIOPOLYMER COMPOSITIONS AND ASSOCIATED DEVICES AND METHODS

The present technology provides biopolymer compositions that form a viscoelastic, injectable material (e.g., a hydrogel) suitable for partially or fully occluding an aneurysm or other space within the body. In some embodiments, the biopolymer compositions described herein include at least one biopolymer (e.g., a polysaccharide) combined with one or more additional components, such as crosslinkers, stabilizers, contrast agents, therapeutic pharmaceutical agents, antimicrobial agents, cellular cargo, etc. The additional component(s) can provide various functions, such as (1) facilitating gelation of the biopolymer (e.g., via chemical and/or physical crosslinking), (2) modulating the material properties (e.g., viscosity, storage modulus, loss modulus) of the biopolymer composition, (3) enhancing the stability of the biopolymer composition (e.g., after sterilization and/or storage), (4) enabling visualization of the biopolymer composition during the treatment procedure (e.g., via radiographic imaging), and/or (5) providing additional therapeutic effects (e.g., healing, antimicrobial activity, etc.). Additional details of the various components of the biopolymer compositions disclosed herein are provided in Sections II.A-II.E below.

The properties of the biopolymer compositions described herein can facilitate sterilization, storage, and/or use, including prior to, during, and/or after introduction into the treatment site. For example, the biopolymer compositions described herein can be used without carrying out any preliminary mixing and/or crosslinking of precursor materials. In some embodiments, the biopolymer composition can be delivered into the patient's body without any prior mixing and/or crosslinking steps that occur within 1 minute, 2 minutes, 5 minutes, 10 minutes, 30 minutes, 1 hour, 2 hours, 4 hours, 8 hours, 12 hours, 24 hours, 36 hours, 48 hours, 3 days, 4 days, 5 days, 6 days, 1 week, 2 weeks, 3 weeks, 4 weeks, 2 months, 3 months, 6 months, or 1 year before delivery. Instead, the biopolymer composition can be provided as an injectable, preformed hydrogel in a sterilized package (e.g., a vial, preloaded syringe) that is immediately ready for use. Accordingly, in contrast to conventional approaches, the biopolymer composition can be used without relying on an in situ polymerization reaction, crosslinking reaction, or other chemical reaction that may occur while the biopolymer composition is being injected, which may cause the biopolymer composition to become too viscous to be injected through a microcatheter. Excessive viscosity may cause plugging or rupture of the microcatheter, and may delay or even prevent a surgical aneurysm repair procedure.

Additionally, the biopolymer compositions disclosed herein can be provided in a preformed, ex vivo state that does not need to undergo any significant changes in material properties before, during, and/or after delivery into the body to effectively occlude the treatment site. As previously discussed, conventional injectable compositions typically exhibit significantly different ex vivo and in vivo properties, and thus must undergo a phase transition within the patient's body to reach a final, therapeutically effective state. For example, conventional compositions are typically in a liquid state ex vivo (e.g., a state having a low viscosity, a low (or zero) degree of crosslinking, and/or a loss modulus greater than the storage modulus), and transition to a solid or semi-solid state (e.g., a state having a high viscosity, a high degree of crosslinking, and/or a storage modulus greater than the loss modulus) when exposed to in vivo conditions (e.g., physiological temperature, pH, salt concentrations, etc.) and/or other conditions intended to induce a phase transition (e.g., physically induced, electromagnetically induced, etc.).

In contrast, the biopolymer compositions described herein can form a solid or semi-solid material (e.g., a viscoelastic, injectable hydrogel) that is highly viscous and/or highly crosslinked before being introduced into the body, and thus exhibits sufficient mechanical strength and cohesiveness for occluding an aneurysm or other treatment site without requiring further crosslinking, phase transitions, and/or other significant changes in material properties. For example, in the ex vivo state, the biopolymer composition can form a unitary, solid mass that sticks to itself and does not disperse or dissolve when placed in a physiological solution (e.g., phosphate-buffered saline). Similarly, when delivered into the body, the biopolymer composition can remain sufficiently solid to fill and seal the treatment site without dispersing or dissolving when exposed to in vivo conditions (at least until biodegradation and/or bioresorption of the biopolymer composition occurs, if applicable). As discussed above, this approach can reduce the likelihood of the biopolymer composition leaking out of the treatment site during and/or after delivery, thus lowering the risk of patient complications such as stroke. However, when subjected to pressure, the biopolymer composition can exhibit viscous deformation suitable for injection into the treatment site via a delivery catheter, such as a microcatheter having an inner diameter less than or equal to 0.02 inches, 0.015 inches, 0.014 inches, 0.013 inches, 0.012 inches, 0.011 inches, or 0.01 inches.

For example, the ex vivo viscosity (e.g., as measured at 20° C. at a shear rate of 1/s) of the biopolymer composition can be at least 20 Pa-s, 25 Pa-s, 30 Pa-s, 35 Pa-s, 40 Pa-s, 45 Pa-s, 50 Pa-s, 75 Pa-s, 100 Pa-s, 150 Pa-s, 200 Pa-s, 250 Pa-s, 300 Pa-s, 350 Pas, 400 Pa-s, 450 Pa-s, 500 Pa-s, or 1000 Pa-s. The ex vivo viscosity can be less than or equal to 500 Pa-s, 450 Pa-s, 400 Pa-s, 350 Pa-s, 300 Pa-s, 250 Pa-s, 200 Pa-s, 150 Pa-s, 100 Pa-s, 75 Pa-s, or 50 Pa-s. In some embodiments, the biopolymer composition is thixotropic, so that it can more readily flow through a delivery catheter and elastically regain its structure at the treatment site. The thixotropic index value of the biopolymer composition can be, for example, at least about 10 Pals, 100 Pals, 500 Pals, 1000 Pa/s, or 5000 Pa/s.

Storage modulus may be used as a proxy for viscosity in situations where the viscosity of the biopolymer composition is too high to be measured by conventional techniques without destroying its material structure. In some embodiments, the ex vivo storage modulus of the biopolymer composition within the linear viscoelastic region is at least 50 Pa, 80 Pa, 100 Pa, 150 Pa, 200 Pa, 250 Pa, 300 Pa, 400 Pa, 500 Pa, or 600 Pa; and/or is no more than 500 Pa, 400 Pa, 300 Pa, 250 Pa, 200 Pa, 150 Pa, or 100 Pa. The ex vivo loss modulus of the biopolymer composition within the linear viscoelastic region can be at least 50 Pa, 80 Pa, 100 Pa, 150 Pa, 200 Pa, 250 Pa, 300 Pa, 400 Pa, 500 Pa, or 600 Pa; and/or can be no more than 500 Pa, 400 Pa, 300 Pa, 250 Pa, 200 Pa, 150 Pa, or 100 Pa. The ex vivo loss modulus of the biopolymer composition can be less than the ex vivo storage modulus of the biopolymer composition, such that the biopolymer composition already acts as a solid or semi-solid material ex vivo. For example, the ratio of the ex vivo storage modulus to the ex vivo loss modulus can be at least 1, 1.1, 1.2, 1.3, 1.4, 1.5, 1.6, 1.7, 1.8, 1.9, 2, 2.5, 3. 3.5, 4, 5, or more. The linear viscoelastic region can correspond to no more than 20%, 15%, or 10% displacement of the biopolymer composition. The storage and loss moduli of the biopolymer composition can be measured using techniques known to those of skill in the art, such as at a temperature of 37° C. using a 40 mm 2° cone and plate rheometer (e.g., a TA Instruments DHR-20 rheometer) oscillating at a suitable frequency (e.g., at or near 1 Hz).

Any reference herein to the ex vivo properties of the biopolymer composition may refer to the properties as measured at least 1 minute, 2 minutes, 5 minutes, 10 minutes, 30 minutes, 1 hour, 2 hours, 4 hours, 8 hours, 12 hours, 24 hours, 36 hours, 48 hours, 3 days, 4 days, 5 days, 6 days, 1 week, 2 weeks, 3 weeks, 4 weeks, 2 months, 3 months, 6 months, or 1 year before delivery into the body or into an in vitro simulation of the treatment site, or as measured in vitro under non-physiological conditions (e.g., 20° C., acidic pH). The ex vivo properties may be measured after sterilization of the biopolymer composition, as described below.

The biopolymer compositions described herein can include one or more other useful characteristics. Those characteristics can include some or all of the following: antimicrobial properties; biocompatibility; biodegradability; hemostatic properties; non-cytotoxic properties; non-immunogenic properties; a substantially collagen-free formulation; linear viscoelastic behavior up to at least 5%, 6%, or 7% strain; and/or elastic behavior up to at least 8%, 9%, or 10% strain.

A. Biopolymers

The biopolymer compositions described herein include at least one biocompatible polymer, also referred to herein as a "biopolymer." The biopolymer can be a naturally occurring polymer, such as a polysaccharide, polypeptide, or polynucleotide. Alternatively or in combination, the biopolymer can be a synthetic polymer that is biocompatible, biodegradable, and/or bioresorbable. Representative examples of biopolymers suitable for use with the present technology include, but are not limited to, chitosan, gelatin, collagen, fibrin, silk, starch, cellulose, agarose, dextran, alginate, hyaluronic acid, extracellular matrix-derived polymers, poly(lactide), poyl(glycolide), poly(lactide-co-glycolide), poly(caprolactone), poly(vinyl alcohol)), cellulose diacetete, ethylene-vinyl alcohol copolymers, or derivatives or combinations thereof. The biopolymer composition can include a single type of biopolymer, or can include a plurality of different biopolymer types (e.g., two, three, four, five, or more biopolymers). In embodiments where the biopolymer composition includes different biopolymer types, the biopolymers can be combined via mixing, crosslinking, copolymerization, etc. In some embodiments, some or all of the biopolymers are water soluble. Any of the biopolymers described herein can be crosslinked or uncrosslinked, and may or may not undergo reaction and covalent bond formation with any other material after being injected.

In some embodiments, the biopolymer has an average molecular weight (e.g., weight average or number average as determined via gel permeation chromatography) of at least 50 kDa, 100 kDa, 150 kDa, 200 kDa, 250 kDa, 300 kDa, 350 kDa, 400 kDa, 450 kDa, 500 kDa or more. Alternatively or in combination, the average molecular weight can be less than or equal to 2000 kDa, 1000 kDa, 750 kDa, 500 kDa, 400 kDa, 300 kDa, 250 kDa, or 200 kDa. The average molecular weight can be within a range from 100 kDa to 200 kDa, from 200 kDa to 250 kDa, from 200 kDa to 300 kDa, from 225 kDa to 275 kDa, from 200 kDa to 500 kDa, or from 250 kDa to 500 kDa. In some embodiments, the viscosity of the biopolymer (e.g., as measured using a 1% solution of the biopolymer in water at 20° C. at a shear rate of 1/s) is at least 25 mPa-s, 50 mPa-s, 75 mPa-s, 100 mPa-s, 150 mPa-s, or 200 mPa-s. Alternatively or in combination, the viscosity of the biopolymer can be less than or equal to 500 mPa-s, 400 mPa-s, 300 mPa-s, 200 mPa-s, 100 mPa-s, or 50 mPa-s. The viscosity of the biopolymer can be within a range from 10 mPa-s to 200 mPa-s, from 25 mPa-s to 100 mPa-s, or from 50 mPa-s to 150 mPa-s.

The concentration of the biopolymer in the biopolymer composition can be varied as desired. For example, the concentration of the biopolymer as expressed in % (w/v) (g per 100 mL solution) can be within a range from 1% to 20%, 1% to 15%, 1% to 10%, 1% to 5%, 2% to 9%, 2% to 5%, 3% to 5%, 4% to 6%, 5% to 10%, or 6% to 9%. The concentration of the biopolymer can be less than or equal to 40%, 30%, 20%, 15%, 12%, 10%, 9%, 8%, 7%, 6%, or 5%. Alternatively or in combination, the concentration of the biopolymer can be greater than or equal to 1%, 2%, 3%, 4%, 5%, 6%, 7%, 8%, 9%, 10%, 12%, 15%, or 20%. In some embodiments, the concentration of the biopolymer is sufficiently high to provide mechanical strength and cohesiveness to the biopolymer composition, e.g., for purposes of forming a tight seal within an aneurysm or other body cavity. However, the concentration can still be sufficiently low so that the biopolymer composition is injectable through a relatively small diameter catheter. The concentration can also be low enough to reduce the likelihood the biopolymer precipitating, e.g., during storage and/or after sterilization. The upper concentration limit for any given biopolymer can depend in part on the biopolymer type, molecular weight, and/or whether any other components (e.g., cosolvents, crosslinkers, spacers) are present. In some embodiments, for example, the upper concentration limit is just below the concentration at which the biopolymer precipitates from the biopolymer composition.

Optionally, the concentration of the biopolymer in the biopolymer composition can be determined based on the entanglement concentration of the biopolymer, which in turn may depend on the type and molecular weight of the biopolymer. The entanglement concentration a biopolymer can be determined by plotting viscosity versus concentration at a set temperature for the biopolymer, then identifying the inflection point above which the viscosity increases more steeply (e.g., exponentially) with increases in biopolymer concentration, and below which the viscosity increases less steeply with increases in biopolymer concentration. Lower molecular weight biopolymers typically will have a greater entanglement concentration than higher molecular weight biopolymers. For example, in some instances, when using a 240 kDa chitosan hydrochloride solution, the entanglement concentration prior to heat sterilization is at least 5%. In some embodiments, the biopolymer composition includes at least an entanglement concentration of the biopolymer. In such embodiments, the biopolymer composition can include a stabilizer to inhibit precipitation of the biopolymer during storage and/or injection, as described further below. Alternatively, the concentration of the biopolymer can be less than the entanglement concentration.

In some embodiments, the biopolymer is a chitosan or a chitosan derivative. Chitosan is a linear polysaccharide that contains randomly distributed D-glucosamine and N-acetyl-D-glucosamine units with a large number of amine groups and hydrogen bonding sites, and may be characterized as a cationic polymer composed from glucosamine monomers. Chitosan may provide desirable biocompatibility and inherent antimicrobial properties. Chitosan is typically made by deacetylation of chitin (poly-N-acetyl-D-glucosamine) to eliminate acetyl groups on the nitrogen atom by hydrolysis. The degree of deacetylation of the chitosan can be at least 50%, 60%, 70%, 75%, 80%, 85%, 90%, or 95%. A variety of chitosans may be used in the disclosed composition. As used herein, "chitosan" encompasses chitosan salts (e.g., chitosan acetate, chitosan citrate, chitosan glutamate, chitosan hydrochloride, chitosan lactate, chitosan nitrate and chitosan phosphate), chitosan oligomers (e.g., chitosan oligosaccharides), and water-soluble chitosan derivatives (e.g., thiolated chitosans, and non-thiolated chitosan derivatives such as acetylated, alkylated or sulfonated chitosans including O-alkyl ethers such as carboxymethyl chitosan, O-acyl esters, cationized (e.g., quaternized) trimethyl chitosans and chitosans modified with polyethylene glycol).

In some embodiments, the chitosan has a plurality of repeating units, such as from 30 to 3000 repeating units, or from 60 to 600 repeating units. As described above, many or most of the repeating units can contain deacetylated amino groups (e.g., at least 60%, 70%, 75%, 80%, or 85% of the total repeating units; and/or up to 90% or 95% of the total repeating units), with the remaining repeating units containing acetylated amino groups. In some embodiments, the chitosan has an average molecular weight (e.g., weight average or number average) of at least 50 kDa, 100 kDa, 150 kDa, 200 kDa, 250 kDa, 300 kDa, 350 kDa, 400 kDa, 450 kDa, 500 kDa; and/or no more than 2000 kDa, 1000 kDa, 750 kDa, 500 kDa, 400 kDa, 300 kDa, 250 kDa, or 200 kDa. The average molecular weight can be within a range from 100 kDa to 200 kDa, from 200 kDa to 250 kDa, from 200 kDa to 300 kDa, from 225 kDa to 275 kDa, from 200 kDa to 500 kDa, or from 250 kDa to 500 kDa. The viscosity of the chitosan (e.g., as measured using a 1% solution of the chitosan in water at 20° C. at a shear rate of 1/s) can be at least 25 mPa-s, 50 mPa-s, 75 mPa-s, 100 mPa-s, 150 mPa-s, or 200 mPa-s. Alternatively or in combination, the viscosity of the chitosan can be less than or equal to 500 mPa-s, 400 mPa-s, 300 mPa-s, 200 mPa-s, 100 mPa-s, or 50 mPa-s. The viscosity of the chitosan can be within a range from 10 mPa-s to 200 mPa-s, from 25 mPa-s to 100 mPa-s, or from 50 mPa-s to 150 mPa-s.

B. Crosslinkers

In some embodiments, the biopolymer compositions disclosed herein include at least one chemical crosslinker configured to cause and/or enhance gelation of the biopolymer composition. The chemical crosslinker can react with functional groups on the biopolymer(s) to form covalent bonds between the biopolymer chains, thus producing a crosslinked biopolymer network (e.g., a hydrogel). In some embodiments, the native biopolymer already includes functional groups capable of reacting with the chemical crosslinker. Alternatively or in combination, the biopolymer can be modified to include non-native functional groups capable of reacting with the chemical crosslinker, in accordance with techniques known to those of skill in the art. Representative examples of chemical crosslinkers include, but are not limited to, small molecular crosslinkers (e.g., genipin, glutaraldehyde, formaldehyde, diethyl squarate, blocked diisocyanate, ethylene glycol diglycidyl ether (EDGE), functionalized polyethylene glycol, carbodiimides, epoxides), photosensitive crosslinkers (e.g., functional azides and acrylates), enzymatic crosslinkers (e.g., phloretic acid, activated quinones), and polymer-based crosslinkers (e.g., crosslinkers acting via disulfide bonding, Michael addition, Schiff base formation, etc.). The biopolymer composition can include a single type of chemical crosslinker, or can include a plurality of different types of chemical crosslinkers (e.g., two, three, four, five, or more different types of chemical crosslinkers).

The chemical crosslinks between the biopolymer chains can increase the viscosity, mechanical strength, and cohesiveness of the biopolymer composition, as well as enhance the resistance of the biopolymer composition to bioresorption and/or prolong the time required for biodegradation. For example, after implantation in vivo, the biopolymer composition can be configured to biodegrade over a period of at least 1 day, 2 days, 3 days, 4 days, 5 days, 6 days, 1 week, 2 weeks, 3 weeks, 4 weeks, 1 month, 2 months, 3 months, 4 months, 5 months, or 6 months; and/or up to 1 year, 6 months, 5 months, 4 months, 3 months, 2 months, 1 month, 4 weeks, 3 weeks, 2 weeks, or 1 week.

The amount of the chemical crosslinker(s) in the biopolymer composition can depend in part upon the type of chemical crosslinker used, the type of biopolymer used, the characteristics of the biopolymer (e.g., molecular weight, degree of deacetylation), and/or additional components in the biopolymer composition (e.g., physical crosslinkers). In some embodiments, the amount of the chemical crosslinker is sufficiently high to confer mechanical strength, cohesiveness, and/or biodegradation resistance, while still sufficiently low to avoid excessive viscosity and/or inadequate thixotropy in the biopolymer composition, which may lead to an undesirably brittle aneurysm seal and/or compromise the injectability of the biopolymer composition. For example, the concentration (% (w/v)) of the chemical crosslinker in the biopolymer composition can be within a range from 0.001% to 10%, from 0.001% to 5%, from 0.001% to 2%, from 0.001% to 1%, from 0.005% to 1%, from 0.005% to 0.1%, from 0.005% to 0.01%, from 0.01% to 5%, from 0.01% to 2%, from 0.02% to 1%, from 0.02% to 0.5%, from 0.02% to 0.1%, from 0.1% to 5%, or from 0.1% to 2%. In some embodiments, the concentration of the chemical crosslinker is no more than 5%, 2%, 1%, 0.5%, 0.2%, 0.1%, 0.05%, 0.02%, 0.01%, 0.009%, 0.008%, 0.007%, 0.06%, 0.005%, 0.004%, 0.003%, 0.002%, or 0.001%. Alternatively or in combination, the concentration of the chemical crosslinker can be at least 0.001%, 0.002%, 0.003%, 0.004%, 0.005%, 0.006%, 0.007%, 0.008%, 0009%, 0.01%, 0.02%, 0.05%, 0.1%, 0.2%, 0.5% or 1%. In other embodiments, however, the chemical crosslinker is optional and may be omitted from the biopolymer composition.

In some embodiments, the biopolymer compositions disclosed herein include at least one physical crosslinker configured to cause and/or enhance gelation of the biopolymer composition, as an alternative or in addition to the chemical crosslinker. The physical crosslinker can interact with the biopolymer chains via noncovalent interactions, such as ionic bonding, hydrogen bonding, Van der Waals interactions, hydrophobic interactions, etc. Physical crosslinks are generally reversible and may be less stable than chemical crosslinks depending on the environmental conditions (e.g., temperature, pH, etc.). Accordingly, the physical crosslinker can be advantageous for conferring mechanical strength and cohesiveness to the biopolymer composition, while also allowing the biopolymer to remain sufficiently flowable for delivery via injection. Optionally, the physical crosslinker can serve to shield charged groups on the biopolymer (e.g., positively charged amine groups on chitosan) that would otherwise repel each other and inhibit gelation.

In some embodiments, the native biopolymer already includes functional groups capable of interacting with the physical crosslinker. Alternatively or in combination, the biopolymer can be modified to include non-native functional groups capable of interacting with the physical crosslinker, in accordance with techniques known to those of skill in the art. Representative examples of physical crosslinkers include, but are not limited to, phosphate, sulfate, and carboxylic salts of polyols (e.g., β-glycerophosphate (BGP) disodium salt or calcium salt); oxidized polysaccharides (e.g., oxidized starch); sugars (e.g., mannitol, glucose); sodium citrate; sodium tripolyphosphate; sulfosuccinic acid; oxalic acid; cations (e.g., metal cations, cationic polymers); anions (e.g., anionic polymers); polymers forming interpenetrating networks; and derivatives and analogs thereof. The biopolymer composition can include a single type of physical crosslinker, or can include a plurality of different types of physical crosslinkers (e.g., two, three, four, five, or more different types of physical crosslinkers).

The amount of the physical crosslinker(s) in the biopolymer composition can depend in part upon the type of physical crosslinker used, the type of biopolymer used, the characteristics of the biopolymer (e.g., molecular weight, degree of deacetylation), and/or additional components in the biopolymer composition (e.g., chemical crosslinkers, stabilizers). In some embodiments, higher amounts of the physical crosslinker provide increased viscosity both before and after sterilization, increased thixotropic index, and a stronger, more cohesive hydrogel once the aneurysm seal has formed. However, the concentration of the physical crosslinker can be sufficiently low to avoid brittleness and maintain viscoelastic behavior for injectability. For example, the concentration (% (w/v)) of the physical crosslinker in the biopolymer composition can be within a range from 0.01% to 20%, 0.1% to 10%, 0.1% to 5%, 0.1%, to 3%, 0.1% to 1%, 0.5% to 10%, 0.5% to 5%, 0.5% to 3%, 0.5% to 2%, 0.5% to 1%, 1% to 10%, 1% to 5%, 1% to 3%, 3% to 10%, 3% to 5%, or 5% to 10%. In some embodiments, the concentration of the physical crosslinker is no more than 20%, 12%, 10%, 9%, 8%, 7%, 6%, 5%, 4%, 3%, 2%, or 1%. Alternatively or in combination, the concentration of the physical crosslinker can be at least 0.1%, 0.5%, 1%, 2%, 3%, 4%, 5%, 6%, 7%, 8%, 9%, or 10%. In other embodiments, however, the physical crosslinker is optional and may be omitted from the biopolymer composition.

C. Stabilizers

In some embodiments, the biopolymer compositions include at least one stabilizer that is configured to inhibit precipitation of the biopolymer composition. In the absence of stabilizers, the biopolymer composition may be prone to precipitation under certain circumstances, such as during and/or after sterilization and/or long-term storage. For example, in embodiments where the biopolymer composition includes chitosan physically crosslinked with BGP, the BGP may become more mobile after thermal sterilization and/or long-term storage, thus allowing hydrophobic groups within the chitosan chains to aggregate with each other, which may cause the chitosan to phase separate and fall out of solution. Precipitation may also occur with biopolymer compositions utilizing other types of physical crosslinkers that are sensitive to changes in temperature, pH, and/or other environmental conditions. As another example, biopolymer compositions that include a relatively high concentration of the biopolymer (e.g., near or above the entanglement concentration) may also be prone to precipitation. For example, biopolymer compositions containing high chitosan concentrations may exhibit high viscosity, excessive changes in viscosity following sterilization, and/or premature precipitation, thus rendering them less suitable for microcatheter injection and more likely to cause microcatheter plugging or rupture if so injected.

To mitigate this issue, the biopolymer composition can include a stabilizer that acts a spacer to maintain separation between the biopolymer chains, even over extended time periods and/or when exposed to different temperatures, pH conditions, etc. The stabilizer can be a relatively large, bulky molecule that provides a spacing effect between moieties on the biopolymer chain (e.g., hydrophobic moieties) that would otherwise be prone to aggregation. For example, the stabilizer can be a polymer that forms an interpenetrating network with the biopolymer. The polymer can optionally include large pendant groups extending from the polymer backbone to provide the spacing effect. In some embodiments, the stabilizer also acts as a thickener to increase the viscosity of the biopolymer composition. This approach can enhance the strength and cohesiveness of the biopolymer composition, without increasing the biopolymer concentration to levels that may lead to precipitation. In such embodiments, the stabilizer can include functional groups that interact with corresponding functional groups on the biopolymer to form inter- and/or intra-molecular linkages to produce a thickening effect. For example, the stabilizer can interact with the biopolymer via noncovalent interactions such as hydrophobic interactions, Van der Waals interactions, hydrogen bonding, physical entanglement, or combinations thereof. However, the interactions between the stabilizer and the biopolymer can be sufficiently weak so the biopolymer remains flowable for injection.

The molecular weight and/or viscosity of the stabilizer can be sufficiently large to confer mechanical strength and/or cohesiveness to the biopolymer composition, but sufficiently small so the biopolymer composition remains injectable In some embodiments, the stabilizer has a molecular weight (e.g., number average or weight average molecular weight, for polymers) of at least 500 Da, 1 kDa, 5 kDa, 10 kDa, 50 kDa, 100 kDa, 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, or 1000 kDa. Alternatively or in combination, the viscosity of the stabilizer (e.g., as measured using a 1% solution of the stabilizer in water at 20° C. at a shear rate of 1/s) can be at least 500 Pa-s, 1000 Pa-s, 1500 Pa-s, 2000 Pa-s, 2500 Pa-s, 3000 Pa-s, 3500 Pa-s, 4000 Pa-s, 4500 Pa-s, or 5000 Pa-s.

The properties of the stabilizer can be configured to avoid undesirable interactions with the biopolymer and/or other components of the biopolymer composition. In some embodiments, for example, the stabilizer is a nonionic compound, which may be beneficial for avoiding complexation with charged biopolymers (e.g., chitosan). The stabilizer may also lack functional groups that would otherwise interact with the chemical and/or physical crosslinkers in the biopolymer composition (if present), to avoid unwanted crosslinking. For example, in embodiments where genipin is used as the chemical crosslinker, the stabilizer can be a compound that does not include any amine groups. Optionally, the properties of the stabilizer can be pH- and/or temperature-independent (or at least be substantially constant over the relevant pH and/or temperature ranges), such that the stabilizer remains effective in inhibiting precipitation under most or all environmental conditions that the biopolymer composition will be exposed to during sterilization, storage, and/or use.

Representative examples of stabilizers suitable for use in the biopolymer composition include, but are not limited to, polysaccharides such as cellulose and cellulose derivatives (e.g., hydroxyethyl cellulose (HEC) cellulose, hydroxymethyl cellulose, hydroxypropyl methylcellulose, carboxymethyl cellulose), guar gum, locust gum, xanthan gum, algin, alginate, agar, carrageenan, pectin, and starch; polypeptides such as gelatin, and collagen; salts (e.g., glucose-1-phosphate); and combinations thereof. Optionally, certain contrast agents may also serve as stabilizers, as described in further detail in Section ILD below. The biopolymer composition can include a single type of stabilizer, or can include a plurality of different types of stabilizers (e.g., two, three, four, five, or more different types of stabilizers).

The amount of the stabilizer(s) in the biopolymer composition can depend in part upon the type of stabilizer used, the characteristics of the stabilizer (e.g., molecular weight), the type of biopolymer used, the characteristics of the biopolymer (e.g., molecular weight, degree of deacetylation), and/or additional components in the biopolymer composition (e.g., crosslinkers). For example, for higher molecular weight and/or highly viscous stabilizers (e.g., polymeric stabilizers), the concentration (% (w/v)) of the stabilizer in the biopolymer composition can be within a range from 0.1% to 20%, 1% to 10%, 1% to 5%, 1% to 3%, 1% to 2%, 2% to 10%, 2% to 5%, 2% to 3%, or 5% to 10%. In some embodiments, the concentration of the stabilizer is no more than 20%, 10%, 9%, 8%, 7%, 6%, 5%, 4%, 3%, 2%, or 1%. Alternatively or in combination, the concentration of the stabilizer can be at least 0.1%, 0.5%, 1%, 2%, 3%, 4%, 5%, 6%, 7%, 8%, 9%, or 10%.

As another example, for lower molecular weight and/or less viscous stabilizers (e.g., non-polymeric stabilizers), the concentration (% (w/v)) of the stabilizer in the biopolymer composition can be within a range from 30% to 80%, 40% to 75%, 40% to 60%, 50% to 70%, or 55% to 65%. In some embodiments, the concentration of the stabilizer is no more than 85%, 80%, 75%, 70%, 65%, 60%, 55%, 50%, 45%, or 40%. Alternatively or in combination, the concentration of the stabilizer can be at least 20%, 25%, 30%, 35%, 40%, 45%, 50%, 55% or 60%. In other embodiments, however, the stabilizer is optional and may be omitted from the biopolymer composition.

In some embodiments, once the biopolymer composition is delivered into the treatment site, the stabilizer is configured to diffuse away from the biopolymer and into the surrounding tissue, leaving behind a more viscous material at the treatment site. This approach can be beneficial for ensuring that biopolymer composition is sufficiently fluid for injection, while also providing the rapid formation of a bioresorbable, cohesive, viscoelastic solid hydrogel tissue seal in vivo. Optionally, the change in viscosity can be sufficiently small such that diffusion of the stabilizer out of the biopolymer composition is not considered to be a phase transition, e.g., the biopolymer composition is in a solid or semi-solid state having a storage modulus to loss modulus ratio greater than 1, both before and after diffusion of the stabilizer. In other embodiments, however, the stabilizer can be configured to remain interpenetrated with the biopolymer even after in vivo delivery. Low molecular weight stabilizers may tend to diffuse away from the biopolymer composition in vivo, while high molecular weight stabilizers may tend to remain with the biopolymer composition in vivo.

D. Contrast Agents

In some embodiments, the biopolymer compositions include at least one contrast agent that enables visualization during and/or after injection into the treatment site. For example, the contrast agent can be configured for radiographic imaging, such as a water-soluble iodine-containing nonionic radiology contrast agent. Representative examples of contrast agents include, but are not limited to, iohexol (e.g., OMNIPAQUE™ from GE Healthcare), iodixanol (e.g., VISIPAQUE™ from GE Healthcare), iopamidol (e.g., ISOVUE™ from Bracco Diagnostics, Inc.), diatrizoate (e.g., HYPAQUE™ from GE Healthcare), iothalamate (e.g., CONRAY™ from Covidien), iopromide, ioversol, ioxilan, iothalamate/meglumine, ioxaglate/meglumine, diatrizoate/meglumine, iodomide sodium, metrizamide, or combinations thereof. The biopolymer composition can include a single type of contrast agent, or can include a plurality of different types of contrast agents (e.g., two, three, four, five, or more different types of contrast agents). The concentration (% (w/v)) of the contrast agent in the biopolymer composition can be within a range from 10% to 80%, 10% to 60%, 10% to 50%, 10% to 40%, 10% to 30%, 20% to 60%, 20% to 50%, 20% to 40%, 20% to 30%, or 25% to 35%. In some embodiments, the concentration of the contrast agent is no more than 90%, 80%, 70%, 60%, 50%, 40%, 30%, or 20%. Alternatively or in combination, the concentration of the contrast agent can be at least 10%, 20%, 30%, 40%, 50%, 60%, 70%, 80%, or 85%. In other embodiments, however, the contrast agent is optional and may be omitted from the biopolymer composition.

As previously described, in some embodiments, the contrast agent also serves as a stabilizer for inhibiting precipitation of the biopolymer. In such embodiments, the contrast agent can be sufficiently bulky to provide a spacing effect to physically separate moieties on the biopolymer chain (e.g., hydrophobic groups) that would otherwise be prone to aggregation. This approach can be advantageous for maintaining stability of the biopolymer composition during sterilization, storage, and/or use, while also enabling the biopolymer concentration to be increased to levels that give improved cohesion and mechanical strength.

In some embodiments, following introduction of the biopolymer composition into a treatment site in vivo, the contrast agent diffuses rapidly into nearby blood, other fluids, or surrounding tissues, for example, within a few (e.g., 10, 5, or 1) minutes. Diffusion of the contrast agent away from the biopolymer may cause the remaining biopolymer composition to increase in viscosity, thus forming a tighter tissue seal. In such embodiments, the contrast agent may not include functional groups, ionic species, or other features that would cause the contrast agent to have an affinity for the biopolymer and/or other components in the biopolymer (e.g., the chemical crosslinker and/or physical crosslinker). Although the time involved in contrast agent diffusion can be evaluated radiographically, another technique is to use a microcatheter (e.g., having an inside diameter of 3.3 mm) to inject a stream of the biopolymer composition into a beaker containing water at 37° C. and to note how long it takes for the stream to change from a transparent appearance to an opaque (e.g., white) cohesive strand. In some embodiments, such a strand forms in less than 10 minutes, 5 minutes, or 3 minutes. In other embodiments, however, the contrast agent can remain with the biopolymer composition even after delivery in vivo.

E. Additional Components

The biopolymer compositions disclosed herein can also include at least one solvent, such as distilled water, deionized water, saline solution, or other biocompatible aqueous solutions. The solvent can optionally be supplied as a part of other components, such as the biopolymer or contrast agent. Cosolvents (e.g., alcohols, ketones or other suitable compounds) may also be employed to assist in dissolving the biopolymer.

Optionally, the biopolymer composition can include one or more adjuvants configured to enhance therapeutic efficacy. Representative examples of adjuvants include the above-mentioned cosolvents, as well as acids, bases, buffering agents, antimicrobial agents, therapeutic agents, and/or other materials. For example, the biopolymer composition can include one more buffering agents configured to maintain the composition at a desired pH value or range. Representative examples of buffering agents include, but are not limited to, potassium chloride, potassium phosphate, potassium hydrogen phthalate, sodium acetate, sodium citrate, sodium phosphate, and their conjugate acids. Optionally, buffering agents that would cause the biopolymer composition to be alkaline may be avoided, as acidic conditions may be desired to promote solubilization and avoid premature precipitation for certain biopolymers, such as chitosan. For example, the biopolymer composition can have a pH from 5 to 5.6, from 5 to 6, from 5 to 7, from 6.5 to 7.0, or from 6.7 to 7.0. In some embodiments, the biopolymer composition has a pH less than or equal to 7, 6.7, 6.5, 6.3, 6, 5.5, or 5. Alternatively, the biopolymer composition can have a physiological pH or an alkaline pH.

In some embodiments, the biopolymer compositions disclosed herein are inherently antimicrobial without requiring addition of a separate antimicrobial agent. For example, the biopolymer can be a material having antimicrobial properties, such as chitosan. Antimicrobial activity may be influenced by the proportion of chitosan in the injectable material (with higher chitosan proportions tending to provide greater antimicrobial activity) and/or by the number of available chitosan amine hydrogen atoms. Accordingly, use of chitosan derivatives containing low numbers of available amino hydrogen atoms may be contraindicated in some embodiments. Alternatively or in combination, the biopolymer composition can include a separate antimicrobial agent. A list of such antimicrobial agents may be found, for example, in U.S. Pat. No. 7,959,943, the disclosure of which is incorporated by reference herein in its entirety.

In some embodiments, the biopolymer compositions disclosed herein include at least one therapeutic agent. Representative examples of therapeutic agents which may be employed in the disclosed injectable materials include, but are not limited to, analgesics, anti-cholinergics, anti-fungal agents, antimicrobial agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, pharmaceutical agents, cellular cargo, mixtures thereof, and other therapeutic materials that will be known to those skilled in the art. A list of such therapeutic agents may be found, for example, in the above-mentioned U.S. Pat. No. 7,959,943. In those instances where it is desirable to remove water from tissue, e.g., to remove fluid from polyps or edematous tissue, the biopolymer composition can include a hyperosmolar agent, such as furosemide, sodium chloride gel, and/or other salt preparations that draw water from tissue or substances which directly or indirectly change the osmolar content of the mucous layer. A release agent modifier may also be include if sustained release or delayed release of a therapeutic agent is desirable.

Other adjuvants that may be included in the disclosed injectable materials include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika, and/or other materials that known to those skilled in the art); indicators; antioxidants; antifoam agents; and/or rheology modifiers including thickeners and thixotropes.

In some embodiments, the biopolymer compositions herein comprise, consist of, or consist essentially of: a biopolymer, a solvent, and a contrast agent; a biopolymer, a solvent, a contrast agent, and a physical crosslinker; a biopolymer, a solvent, a contrast agent, and a chemical crosslinker; a biopolymer, a solvent, a chemical crosslinker, a physical crosslinker, and a contrast agent; a biopolymer, a solvent, a chemical crosslinker, a stabilizer, and a contrast agent; a biopolymer, a solvent, a chemical crosslinker, a physical crosslinker, a stabilizer, and a contrast agent; combinations thereof; or combinations thereof with optional adjuvants.

F. Associated Devices and Methods

The biopolymer compositions of the present technology can be provided in a suitable container, such as vials, syringes, ampoules, sachets, or other packaging made of glass, metal, or suitable plastics. The container can hold at least 5 mL, 10 mL, 15 mL, or 20 mL of the biopolymer composition; and/or up to 100 mL, 75 mL, or 50 mL of the biopolymer composition. The container can be transparent, can include an outer sealed enclosure (e.g., a plastic bag), and/or may include suitable labels, warnings, and/or instructions. As previously discussed, the biopolymer composition can be ready for immediate use without any mixing of precursor materials. Accordingly, all of the components of the biopolymer composition (e.g., the biopolymer, crosslinkers, stabilizers, contrast agent, solvent) can be provided in a single sealed container.

In some embodiments, sterilization is performed after the biopolymer composition has been placed inside a suitable sealed container. For example, heat sterilization can be performed using sufficiently high temperatures for a sufficiently long time to remove, kill, or deactivate bacteria. Suitable heat sterilization procedures can include, for example, the use of heated or boiling liquids, steam, dry heat, etc., at temperatures of at least 100° C., 105° C., 110° C., 115° C., 120° C., or 125° C.; and/or for at least 5 minutes, 10 minutes, 15 minutes, 20 minutes, 25 minutes, or 30 minutes.

Following sterilization, the biopolymer composition can optionally be subjected to a heat annealing step. Annealing can be performed at a variety of temperatures between room temperature and the glass transition temperature of the biopolymer, with longer annealing times being used with lower temperatures, and vice-versa. Annealing can enable the biopolymer chains to rearrange to a configuration having improved storage stability as manifested by reduced change in viscosity. One technique for determining appropriate annealing times and temperature is to evaluate the storage modulus within the linear viscoelastic range for partially annealed samples at intervals throughout a proposed annealing cycle, using an amplitude sweep viscosity measurement, and to anneal the samples long enough to observe plateauing in the measured storage modulus value. Annealing can be performed immediately after heat sterilization, while the heat-sterilized samples are cooling down, and can involve holding the samples at an appropriate annealing temperature, for example, a temperature from 40° C. to 45° C., and for a time period from 2 hours to 6 hours, or more. In other embodiments, the annealing step is optional and can be omitted.

In some embodiments, the biopolymer composition remains stable after sterilization for an extended period of time, such as a storage time period of at least 1 month, 2 months, 3 months, 4 months, 5 months, 6 months, 7 months, 8 months, 9 months, 10 months, 11 months, 1 year, 2 years, 3 years, or more. The stability of the biopolymer composition can be determined in various ways. For example, the biopolymer composition can be considered stable if there is no precipitation of the biopolymer during the storage time period. The onset of such precipitation can be instrumentally detected, but may also be detected with reasonable accuracy via visual examination of a clear test tube containing the biopolymer composition to determine if is transparent. Solutions in which precipitation has not taken place may be transparent, whereas solutions in which precipitation has taken place may be cloudy or opaque. As another example, the biopolymer composition can be considered stable if the material properties of the biopolymer composition exhibit little or no change during the storage time period. In some embodiments, the storage modulus and/or loss modulus of the biopolymer composition at the end of the storage time period can be within 25%, 20%, 15%, 10%, 5%, or 1% of the storage modulus and/or loss modulus at the beginning of the storage time period, respectively. Storage stability may be assessed by aging the biopolymer composition in a sterilized container at room temperature (e.g., 20° C.) for the storage time period. Optionally, storage stability over longer time periods can be simulated by aging the biopolymer composition in a sterilized container at an elevated temperature. For example, aging of the biopolymer composition at 55° C. for 50 days may be equivalent to a storage period of 1 year at room temperature.

In some embodiments, the disclosed biopolymer composition is ready-to-use as supplied, and thus can be removed under sterile conditions from the container and immediately introduced into a delivery catheter at any desired time during an aneurysm treatment procedure, and without the need to carry out any preliminary mixing or standing steps prior to such introduction. However, if desired, the biopolymer composition can be formulated in other than a ready-to-use configuration, for example, by lyophilizing the composition so that it can be packaged in a freeze-dried configuration, stored for an indefinite period, and later reconstituted at the time of surgery.

In some embodiments, the present technology provides a method for occluding a treatment site, such as an aneurysm, within a patient's body. The method can include providing a biopolymer composition in a preformed state (e.g., as an injectable, cohesive hydrogel) that is ready for use without mixing and/or crosslinking of precursor components. For example, the biopolymer composition can be provided in a sterilized container holding all of the components of the biopolymer composition (e.g., biopolymer, chemical crosslinker, physical crosslinker, stabilizer, contrast agent, etc.).

The method can further include delivering the biopolymer composition to the treatment site using a suitable treatment system. For example, the biopolymer compositions of the present technology can be delivered using any of the treatment systems described herein (e.g., the system 100 of FIGS. 1A-2D), as well as with the treatment systems disclosed in U.S. Pat. No. 10,576,099, U.S. Patent Application Publication No. 2021/0128168, U.S. Patent Application Publication No. 2021/0153872, the disclosures of each of which are incorporated herein by reference in their entirety. As described elsewhere herein, the treatment system can include an elongated shaft (e.g., a microcatheter or other delivery catheter) that is configured to be advanced through the patient's vasculature to the treatment site. The biopolymer composition can be loaded into an injector that is fluidly coupled to the elongated shaft to push the biopolymer composition through the lumen of the elongated shaft and into the treatment site. Optionally, in embodiments where the biopolymer composition is used to treat an aneurysm, the biopolymer composition can be used in combination with a neck cover (or other implantable device) configured to retain the biopolymer composition at the desired treatment site.

Once introduced into the treatment site, the biopolymer composition can agglomerate into a unitary, cohesive mass that partially or fully occludes the treatment site. As previously discussed, the biopolymer composition can be provided and injected in a preformed state that is sufficiently solid to occlude the treatment site without requiring any phase transitions and/or other significant changes in material properties that are triggered by exposure to physiological temperature, pH, and/or other in vivo conditions.

III. ADDITIONAL EMBODIMENTS OF TREATMENT SYSTEMS AND DEVICES

FIGS. 3-7C illustrate additional embodiments of treatment systems and devices suitable for use with the biopolymer compositions of the present technology. Although some of the embodiments of FIGS. 3-7C are described herein in the context of treating aneurysms such as cerebral aneurysms, this is not intended to be limiting, and the embodiments herein can also be used in the treatment of other types of vascular defects, and/or in any other application involving delivery of a biopolymer composition into a space within a patient's body. The features of embodiments of FIGS. 3-7C can be combined with each other and/or with any of the other embodiments described herein, such as the system 100 of FIGS. 1A-2E.

Figure 3:
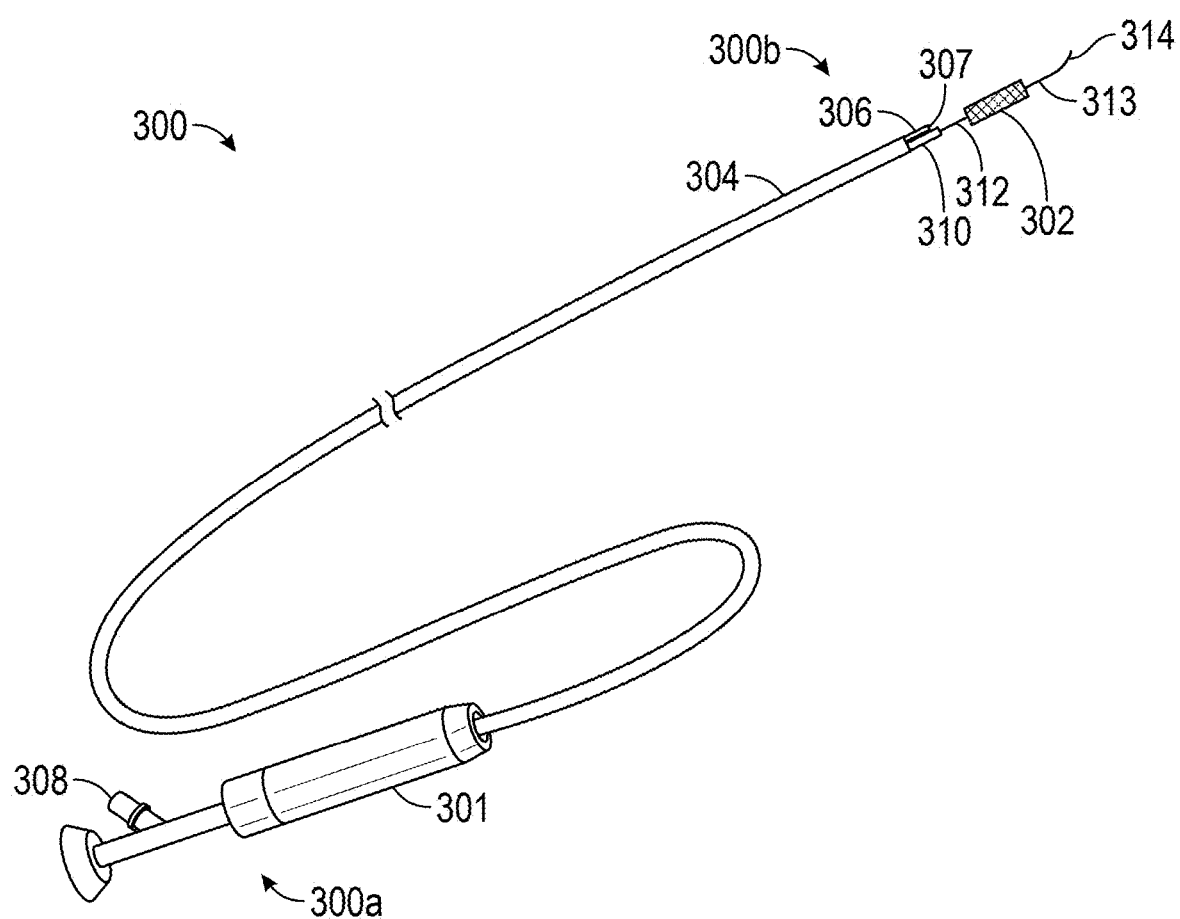
FIG. 3 is a perspective view of another treatment system configured in accordance with embodiments of the present technology.

FIG. 3 is a perspective view of another treatment system 300 ("system 300") configured in accordance with embodiments of the present technology. The system 300 has a proximal portion 300a configured to be extracorporeally positioned during treatment and a distal portion 300b configured to be intravascularly positioned within a blood vessel (such as an intracranial blood vessel) at a treatment site at or proximate an aneurysm. The system 300 can include a handle 301 at the proximal portion 300a, a support structure 302 at the distal portion 300b, and a plurality of elongated shafts or members extending between the proximal and distal portions 300a and 300b. For example, in some embodiments, such as that shown in FIG. 3, the system 300 can include an elongated first member 304 (such as a guide catheter, balloon guide catheter, distal access catheter, etc.) and elongated second and third members 306, 310 configured to be slidably disposed within a lumen of the first member 304. The second member 306 can be configured to receive a biopolymer composition therethrough (e.g., from the embolic kit 200 of FIG. 1A), and the third member 310 can be configured to house the support structure 302 in a collapsed configuration. The second member 306, for example, can have an exit port 307 in fluid communication with an injection port 308 at the proximal portion 300a of the system 300 and through which the biopolymer composition is configured to be delivered. The system 300 may further include an elongated fourth member 312 (such as a guidewire) configured to be slidably disposed within a lumen of the third member 310. In some embodiments, such as that shown in FIG. 3, the distal end portion 314 of the elongated fourth member 312 may be curved to form an atraumatic leading surface.

As discussed herein, the support structure 302 can be any device configured to be positioned within the blood vessel lumen across or adjacent the aneurysm neck and stabilize one or more components of the system 300 at the treatment site or reinforce the aneurysm neck before, during, and/or after delivery of the biopolymer composition. The support structure 302 can have an expanded state (as shown in FIG. 3) and a low-profile state (e.g., a collapsed state) in which the support structure 302 is sufficiently compact to move longitudinally within the third member 310. In some embodiments, the support structure 302 is a flow diverter in the form of a generally tubular mesh having a porosity sufficient to divert blood flow away from the aneurysm. The flow-diverting mesh can be a laser cut stent, a braid, a weave, etc. In some embodiments, the flow diverter comprises a braid formed of a plurality of interwoven filaments that shift relative to one another as the flow diverter moves between its expanded and low-profile states. Example flow diverters for use with the present disclosure include Pipeline™ Flex (Medtronic Neurovascular, Irvine, CA). In some embodiments, the support structure 302 is not a flow diverter. For example, the support structure 302 can be a stent having a higher porosity than that of a conventional flow diverter. A proximal end portion of the support structure 302 can be detachably or non-detachably coupled to an elongate manipulation member 313, such as a rod or tube that is configured to be slidably disposed within a lumen of the third member 310. The system 300 can be steerable or non-steerable and can be configured for deployment by guide wire, by guide sheath, or in another suitable manner.

FIGS. 4A-4F show an example method of treating an aneurysm using the system 300 of FIG. 3, in accordance with embodiments of the present technology. The method can include intravascularly advancing the second member 306 toward an intracranial aneurysm 402 (or other treatment location such as any of those described herein) along the blood vessel 400. The method can further include extending the second member 306 though a neck 404 of the aneurysm 402 to locate the exit port 307 of the second member 306 within an internal volume of the aneurysm 404. Although the internal volume of the aneurysm 402 is empty of non-anatomical material or structures in the illustrated embodiment, in other embodiments, the internal volume of the aneurysm 402 may contain such material or structures. For example, the internal volume of the aneurysm 402 can contain a previously introduced intrasaccular structure or occlusive material, such as one or more embolization coils or one or more intrasaccular mesh structures. Therefore, the disclosed method can further include introducing of a permanent intrasaccular device such as an embolization coil or a mesh embolization device. Such embodiments of the method can include introducing one or more such permanent intrasaccular devices into the aneurysm before delivering the injectable material into the aneurysm.

The method can continue with intravascularly advancing the support structure 302 toward the aneurysm 402 while the support structure 302 is in its low-profile state, and then reinforcing the neck 404 by moving the support structure 302 from its low-profile state toward its expanded state within a main lumen 406 of the blood vessel 400. In addition to reinforcing the neck 404, the support structure 302 can also stabilize the position of the exit port 307 within the aneurysm 402 by pressing a portion of the second member 306 against a wall 408 of the blood vessel 400.

In some embodiments, the support structure 302 is a balloon configured to be intravascularly advanced in a low-profile state (e.g., a deflated state) and deployed in an expanded state (e.g., an at least partially inflated state). Use of a balloon as the support structure 302 may be advantageous, for example, when the intravascular anatomy around an aneurysm is not suitable for deploying a flow diverter. In some cases, the balloon is a tubular balloon having an annular form or another suitable form with a longitudinal flow passage therethrough for avoiding complete or near complete occlusion of a blood vessel in which the balloon is deployed. Alternatively, a balloon that lacks such a flow passage may be used when such complete or near complete occlusion of a blood vessel is acceptable.

Figure 4A:
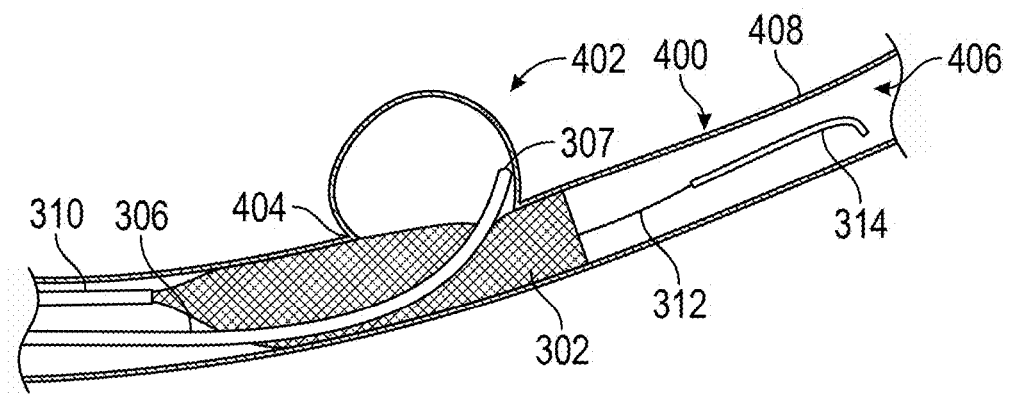
FIGS. 4A-4F show an example method of treating an aneurysm using the treatment system of FIG. 3, in accordance with embodiments of the present technology.
Figure 4B:
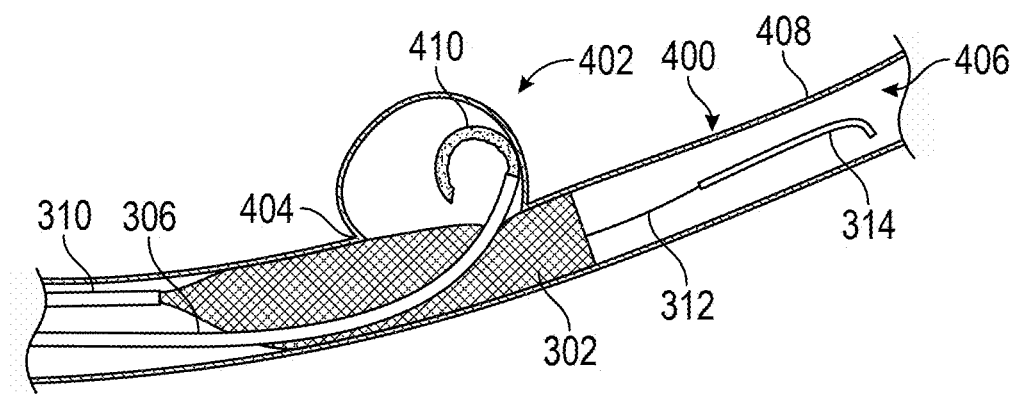
Figure 4C:
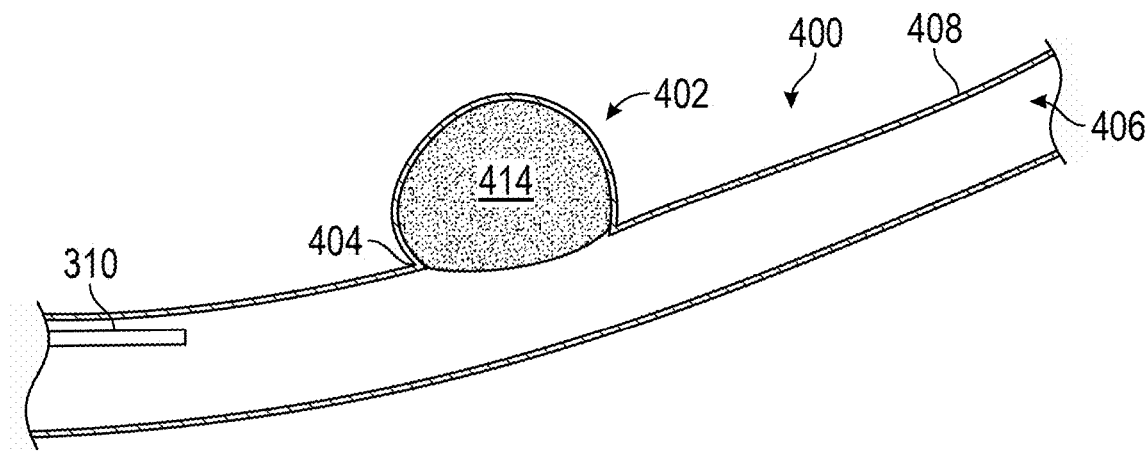
Figure 4D:
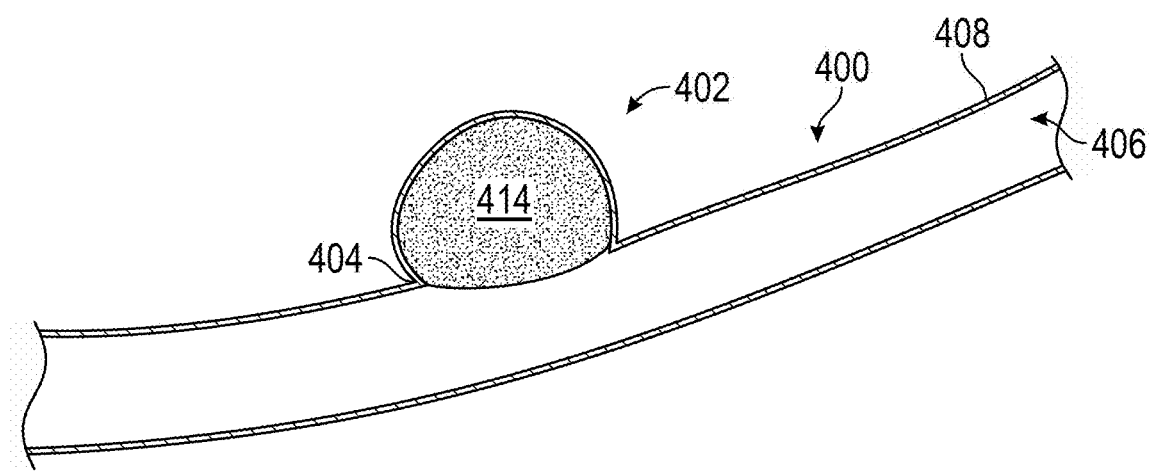

With reference to FIGS. 3-4D, the disclosed method includes injecting the biopolymer composition of the present disclosure into the injection port 308 and through the second member 306. The biopolymer composition 410 exits the second member 306 through exit port 307 into the aneurysm cavity as a thin cohesive strand. The biopolymer composition 410 can form a bioresorbable, cohesive, viscoelastic solid hydrogel mass 414 and seal inside the aneurysm 404. After the mass 414 has sufficiently solidified, the support structure 302 can be withdrawn into the third member 310, and the third member 310 and the remainder of the first member 304 can be withdrawn from the vessel 400. In the illustrated embodiment, the mass 414 occupies all of the internal volume of the aneurysm 402 and the area of the aneurysm neck 404. In other embodiments, the mass 414 can occupy less than all (e.g., from 20% to 100%, from 50% to 100%, or from 75% to 100%) of the total internal volume of the aneurysm 404, e.g., when used in combination with additional aneurysm treatments such as embolic coils or implants. In should be noted that, although the support structure 302 has been removed in the illustrated embodiment, in other embodiments, the support structure 302 can be left in place. In such embodiments, new endothelial cells can grow between and over filaments or struts of the support structure 302.

Figure 4E:
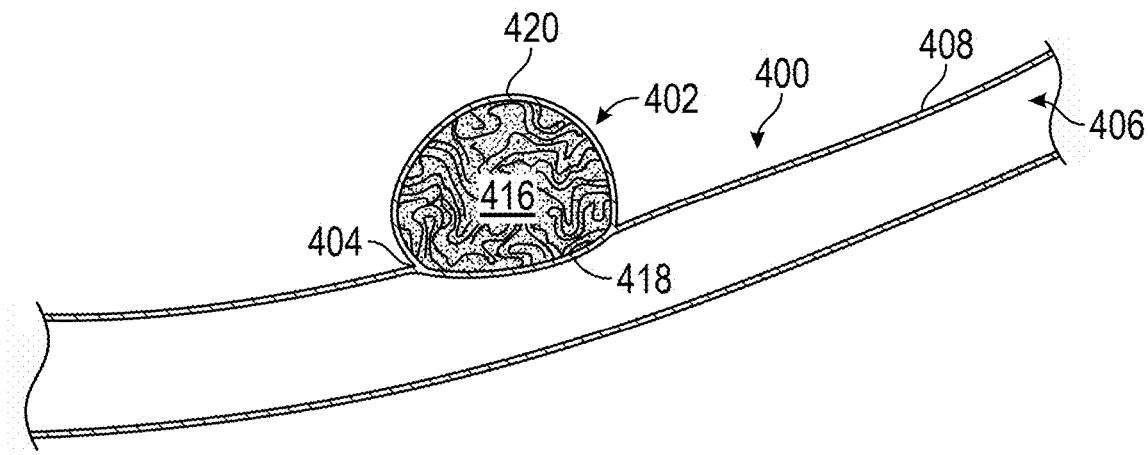
Figure 4F:
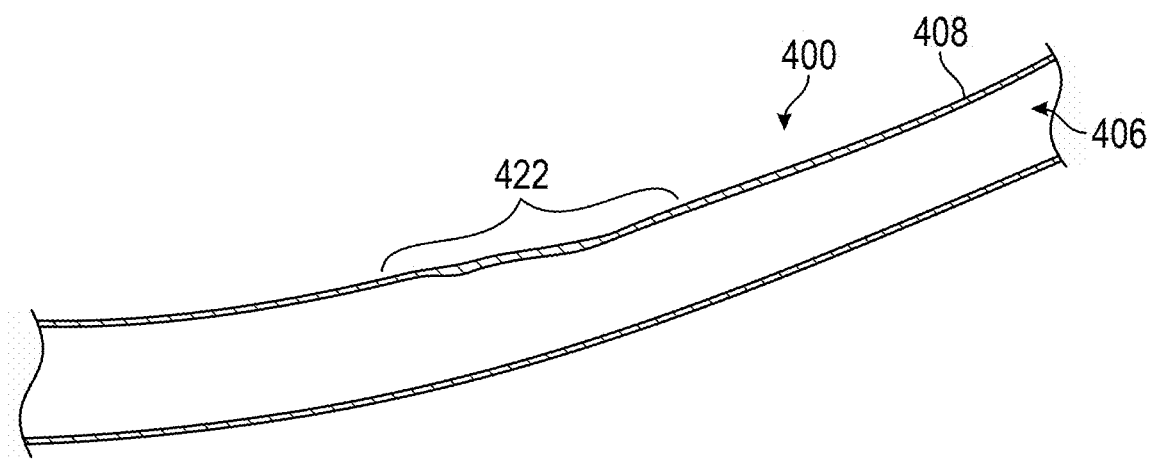

As shown in FIGS. 4E and 4F, natural vascular remodeling mechanisms or bioabsorption of the mass 414 may lead to formation of a mass 416 containing a thrombus or fibrous tissue within the internal volume of the aneurysm 402. These mechanisms may also lead to cell death near the neck 404 and growth of new endothelial cells 418 along a surface of the mass 416 bordering the main lumen 406 of the vessel 400. Eventually, the mass 416 and the cells at the wall 420 of the aneurysm 402 may fully degrade, leaving behind a successfully remodeled region 422 of the blood vessel 400.

Figure 5A:
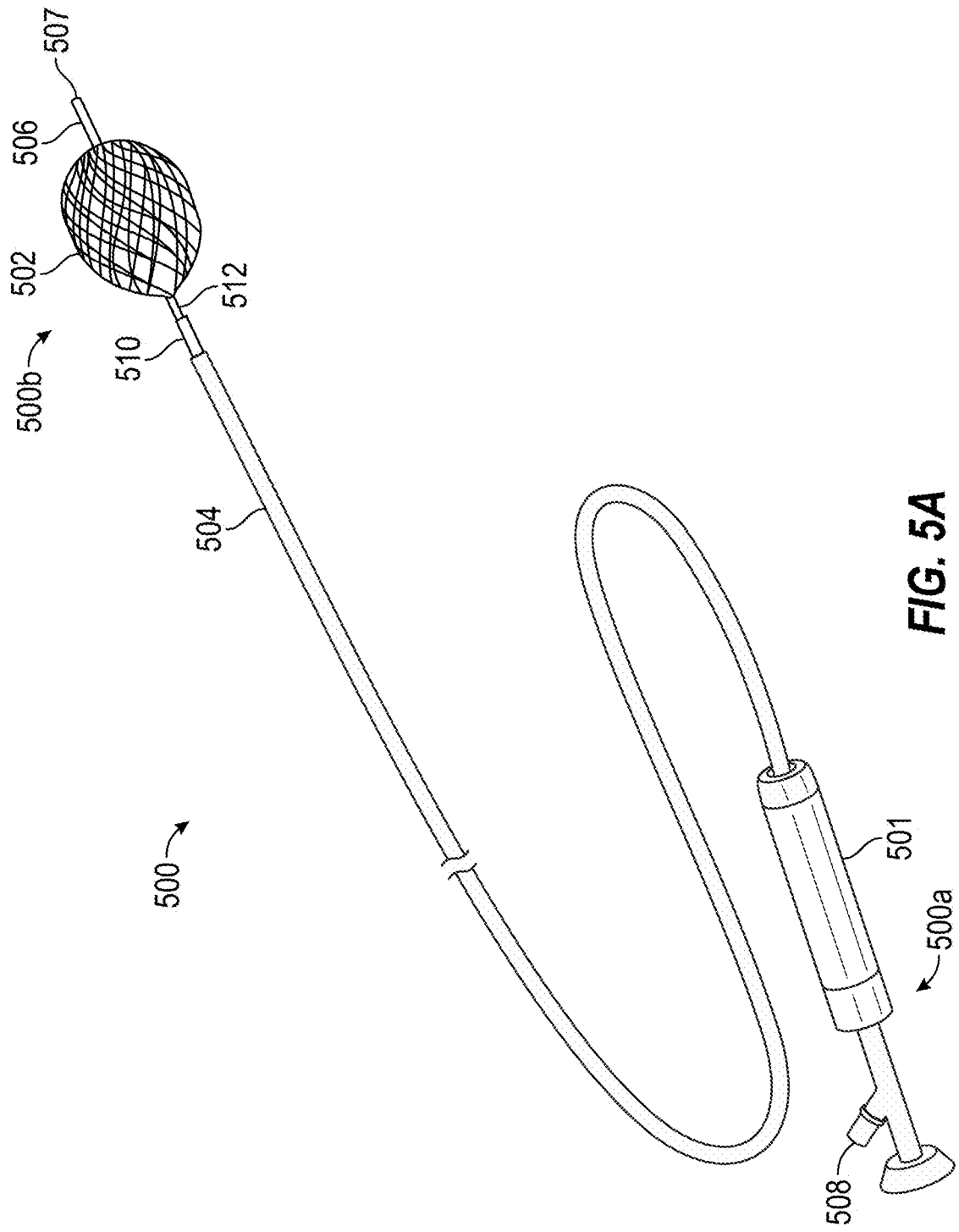
FIG. 5A is a perspective view of another treatment system configured in accordance with embodiments of the present technology.

FIG. 5A is a perspective view of another treatment system 500 ("system 500") configured in accordance with embodiments of the present technology. The system 500 has a proximal portion 500a configured to be extracorporeally positioned during treatment and a distal portion 500b configured to be intravascularly positioned within a blood vessel (such as an intracranial blood vessel) at a treatment site at or proximate an aneurysm. The treatment system 500 can include a handle 501 at the proximal portion 500a, an expandable occlusive member 502 (shown in its expanded state) at the distal portion 500b, and a plurality of elongated shafts or members extending between the proximal and distal portions 500a and 500b. For example, the treatment system 500 can include an elongated outermost member 504 (such as a guide catheter or balloon guide catheter), an elongated innermost member 506 (such as a microcatheter) configured to be slidably disposed within a lumen of the member 504 and having an exit port 507 in fluid communication with injection port 508, an elongated intermediate member 510 (such as a sheath) configured to be slidably disposed within a lumen of the first member 504 and containing an elongated further member 512 (such as an additional sheath) whose distal end is detachably connected to the occlusive member 502. The elongated innermost member 506 can be inserted into the system 500 before the occlusive member 502 is expanded, while the occlusive member 502 is expanded, or after the occlusive member 502 has been expanded and then retracted to a partially inverted state as discussed in more detail below. The elongated innermost member 506 is configured to deliver a biopolymer composition (e.g., received from the embolic kit 200 of FIG. 1A) though exit port 507 to a position beyond the proximal end of the partially inverted occlusive member 502. As such, the biopolymer composition becomes positioned between the occlusive member 502 and an inner wall of the aneurysm cavity, as described in greater detail below.

Figure 5B:
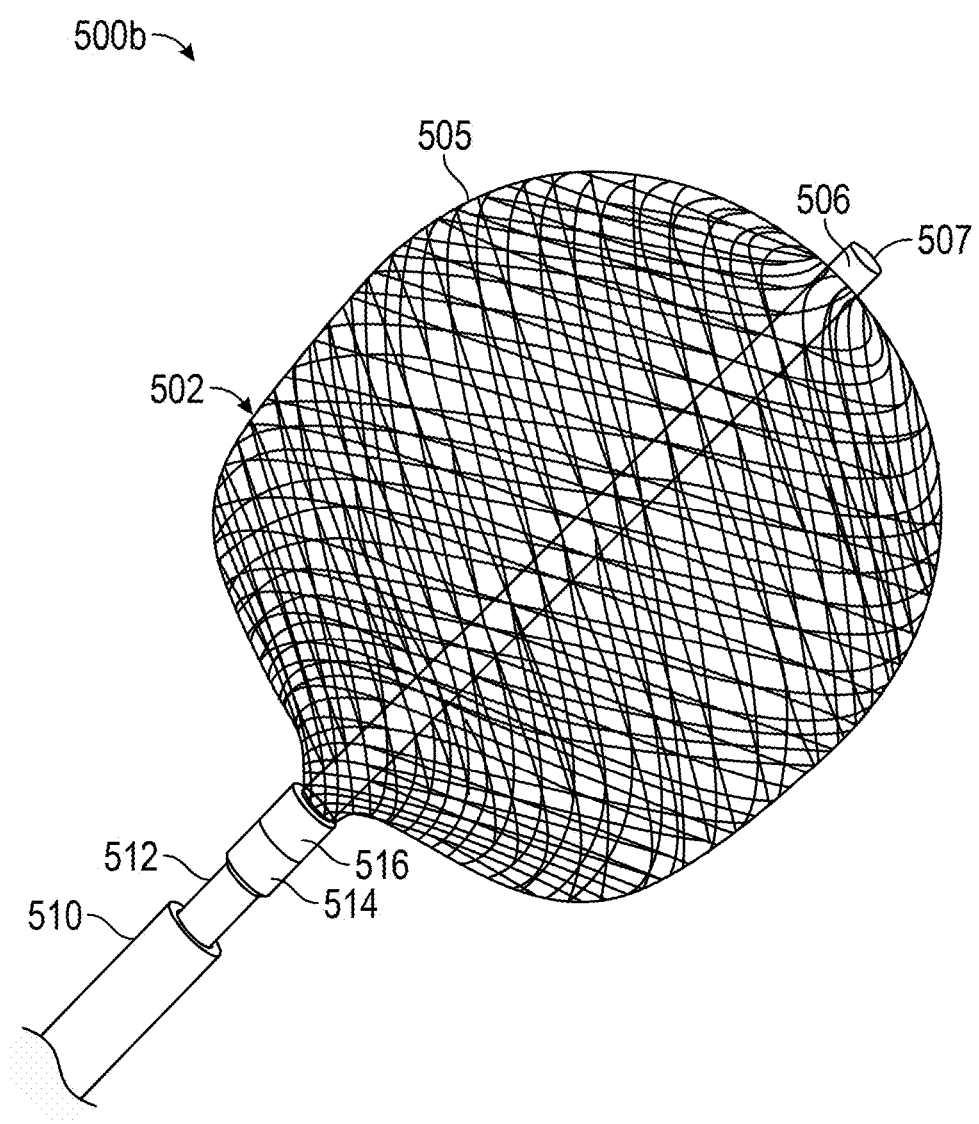
FIG. 5B is an enlarged view of a distal portion and occlusive member of the treatment system of FIG. 5A.

FIG. 5B is an enlarged view of the distal portion 500b of the system 500 and its occlusive member 502. The occlusive member 502 can be a mesh of wires 505. The proximal end of the occlusive member 502 can be detachably coupled to a distal end of the elongated member 512, and the distal end of the occlusive member 502 can be detachably coupled to a distal end of the elongated member 506. For example, the elongated member 506 can include a first coupler 514, and the distal end of the occlusive member 502 can include a second coupler 516 configured to detachably couple with the first coupler 514. Similar but smaller diameter couplers (not shown in FIG. 5B) can be included at the proximal end of the occlusive member 502 and elongated member 506 to permit deformation and inversion of a portion of the occlusive member 502, as discussed in more detail below. The system 500 can be steerable or non-steerable and can be configured for deployment by guide wire, by guide sheath, or in another suitable manner. Furthermore, the member 504 can be of a suitable size to be located within an intracranial blood vessel. In at least some cases, the member 504 is at most 3 French.

Figure 6A:
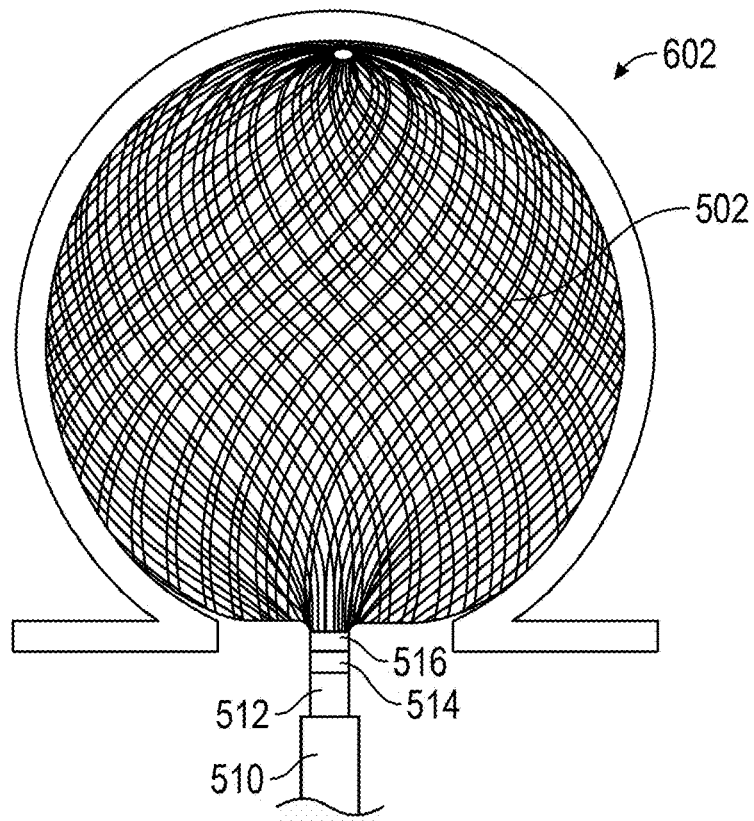
FIGS. 6A-6C show an example method of treating an aneurysm using the treatment system of FIGS. 5A and 5B, in accordance with embodiments of the present technology.
Figure 6B:
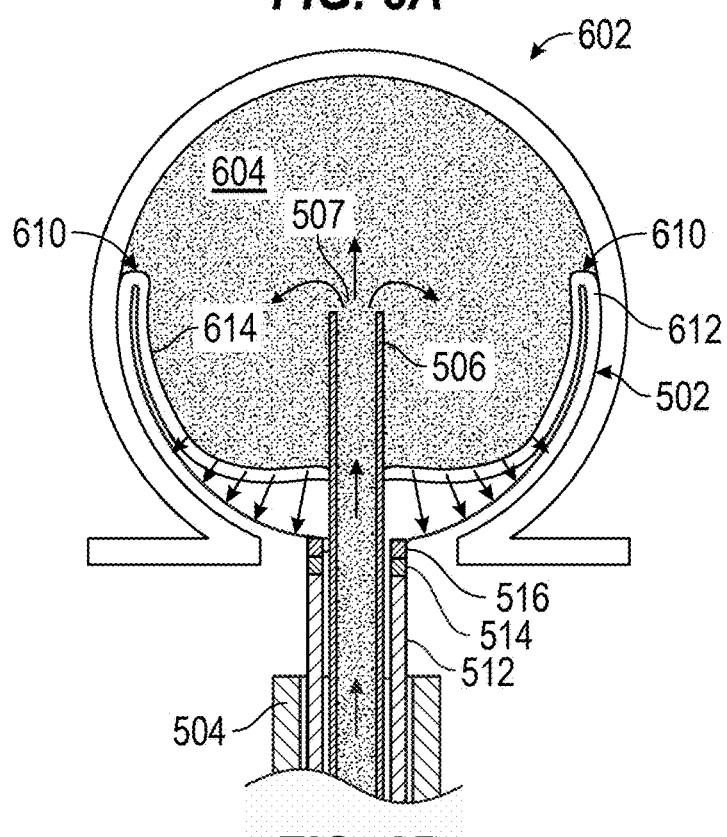
Figure 6C:
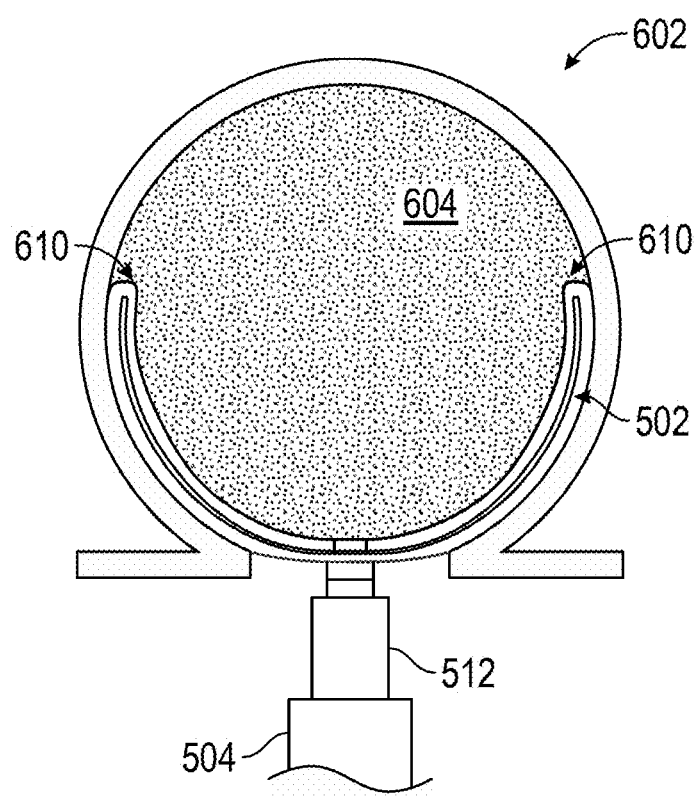

FIGS. 6A-6C show an example method of treating an aneurysm using the system 500 of FIGS. 5A and 5B, in accordance with embodiments of the present technology. In FIG. 6A, the occlusive member 502 has expanded to substantially fill the interior volume of aneurysm 602. In FIG. 6B, the interior volume of aneurysm 602 has been largely filled with a biopolymer composition 604 injected through the exit port 507 at the end of the elongated member 506. The biopolymer composition 604 occupies the interior volume left by the retraction and partial inversion of the occlusive member 502. An annular ridge 610 separates an outer first portion 612 of the occlusive member 502 from an inner second portion 614. In the embodiment shown in FIG. 6B, pressure exerted by the biopolymer composition 604 helps invert the proximal end of the occlusive member 502. However, the occlusive member 502 can also be manually retracted using a suitable wire or other member (not shown in FIG. 6B) prior to injection of the biopolymer composition 604. FIG. 6C shows aneurysm 602 after it has been completely filled with the biopolymer composition 604. The biopolymer composition 604 can form a bioresorbable, cohesive, viscoelastic solid hydrogel mass that seals the aneurysm 602 and facilitates healing thereof.

Figure 7A:
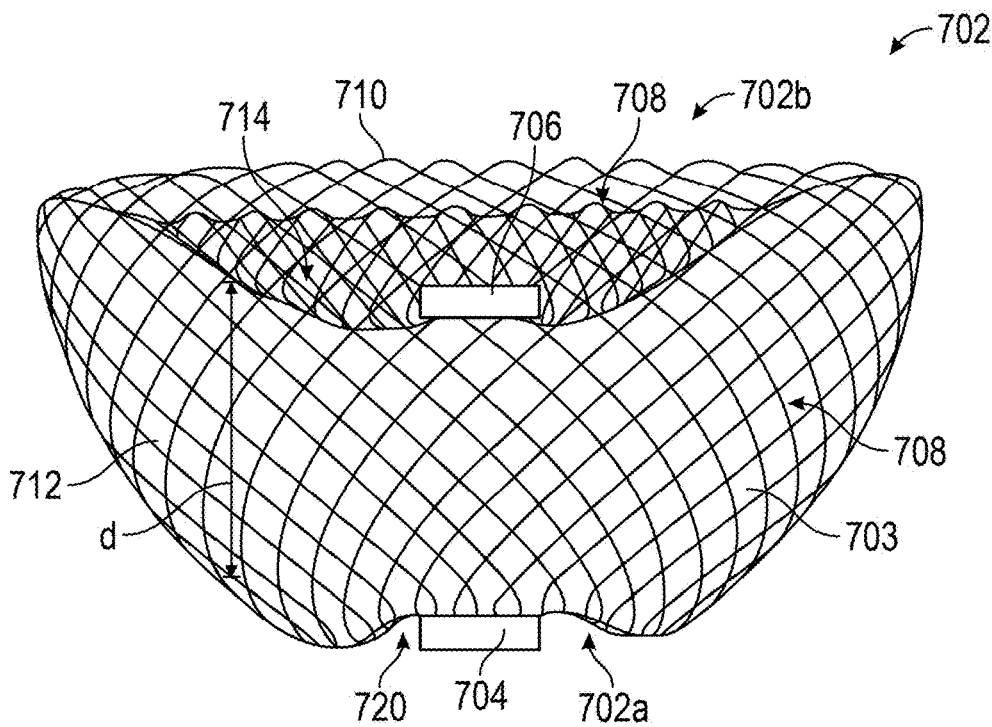
FIG. 7A is a side view of an occlusive member configured in accordance with embodiments of the present technology.
Figure 7B:
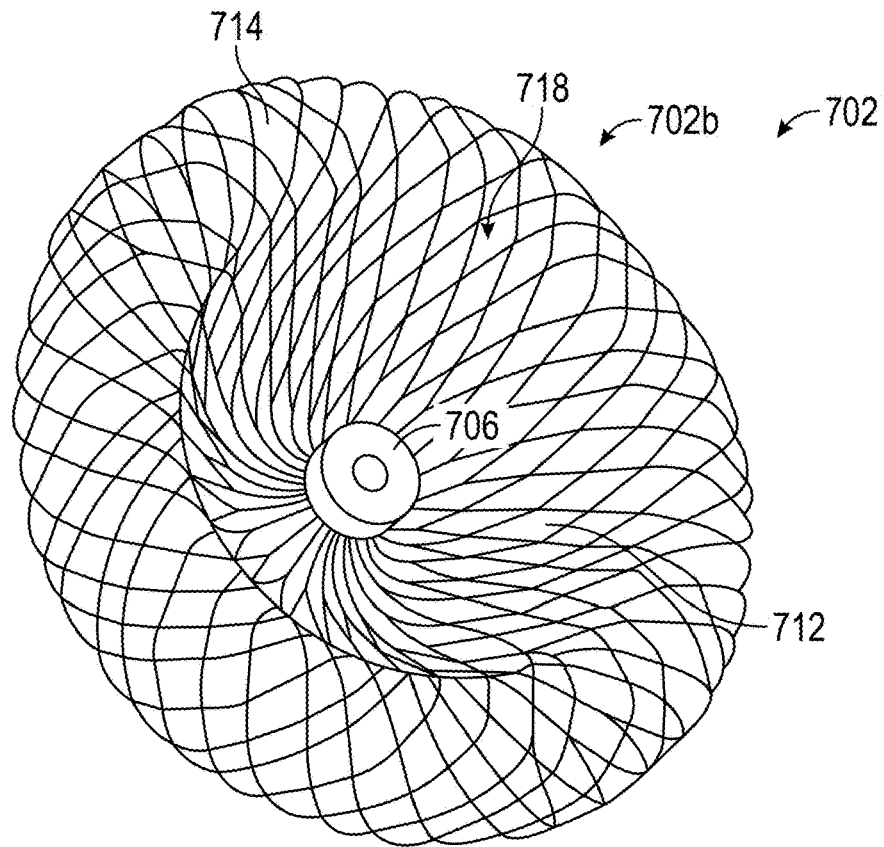
FIG. 7B is a perspective view of the occlusive member of FIG. 7A.
Figure 7C:
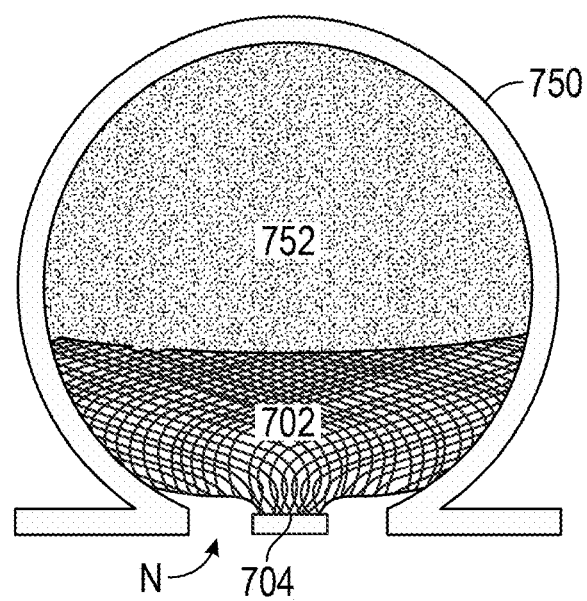
FIG. 7C is a partially schematic side view of the occlusive member of FIGS. 7A and 7B in an aneurysm.

FIGS. 7A-7C illustrate an occlusive member 702 configured in accordance with embodiments of the present technology. The occlusive member 702 can be used in place of the occlusive member 502 of the system 500 of FIGS. 5A and 5B, and for which the principles of operation will be similar to those of the occlusive member 502. Accordingly unless otherwise indicated, the discussion that follows will generally apply to both the occlusive member 502 and the occlusive member 702.

FIG. 7A is a slightly-angled side view of the occlusive member 702 in a retracted, partially inverted position; FIG. 7B is a perspective view of the occlusive member 702; and FIG. 7C is a partially schematic side view of the occlusive member 702 and a biopolymer composition in an aneurysm. The occlusive member 702 can include a mesh of filaments 703 (e.g., wires), with the occlusive member 702 having a proximal portion 702a configured to be positioned over a neck of an aneurysm, a distal portion 702b configured to face the interior of the aneurysm, a proximal coupler 704, and a distal coupler 706. In some embodiments, the mesh is biased towards a predetermined shape when the mesh is in an expanded, unconstrained state. The mesh can be formed of a wall surrounding an interior region 708 and comprising an annular ridge 710 separating a first portion 712 from a second portion 714. The first portion 712 and the second portion 714 can be separated by a distance d that increases towards the central longitudinal axis of the occlusive member 702. In some embodiments, the distance d is generally constant or decreases towards the central longitudinal axis of the occlusive member 702. The first portion 712 of the wall can extend between the proximal coupler 704 and the ridge 710, and the second portion 714 of the wall can extend between the ridge 710 and the distal coupler 706.

In some embodiments, the occlusive member 702 has a distal wall that bows outwardly away from the interior region in a first expanded state (similar, for example, to the occlusive member 502 in FIG. 5A), or a distal wall that may be substantially flat in the first expanded state. However, unlike the occlusive member 502, the distal wall of the occlusive member 702 bows inwardly towards the interior portion 708 in the first expanded state, thereby forming a cavity 718 at the distal portion 702b of the occlusive member 702. The cavity 718 can, for example, be bound by the second portion 714 of the wall and a plane lying on ridge 710. All or a portion of the distal coupler 706 can thus be positioned within the cavity 718, below the plane defined by the ridge 710. In some embodiments, the occlusive member 702 or its mesh includes a recessed portion 720 at the proximal portion 702a that surrounds all or a portion of the proximal coupler 704. In other embodiments, the occlusive member 702 or its mesh does not include a recessed portion 720 at the proximal portion 702a.

Because the second portion 714 bows inwardly, and as may be better understood by referring to FIG. 7B, the occlusive member 702 is less likely to elongate when deployed in the aneurysm and may elongate less than occlusive members with an outward bow or a substantially flat distal wall. In addition, because the bowed second portion 714 is already in a semi-collapsed state, the occlusive member 702 does not have to rely on proximally-directed forces (applied for example by retraction of a wire or by pressures from a biopolymer composition) to further invert the occlusive member 702. The biopolymer composition can fill instead the space between the second portion 714 and an aneurysm wall with or without causing the second portion 714 to move towards the first portion 712, and with less likelihood that excess pressure may be applied to the aneurysm wall.

As shown in FIG. 7C, and following further retraction and detachment as may be needed of the temporary couplers proximate occlusive member 702, the remaining volume of aneurysm 750 may be filled with a biopolymer composition 752 which forms the disclosed viscoelastic solid hydrogel and aneurysm seal.

In some embodiments, the disclosed occlusive members or their mesh may be formed of a plurality of braided filaments, each having first and second ends and a length measured therebetween. The first and second ends of such filaments may be secured relative to one another at the same location (e.g., a proximal coupler), or the first and second ends may be secured relative to one another at separate locations (e.g., at separate couplers). For example, the first ends of the filaments 703 can be secured relative to one another at the proximal coupler 704, and the second ends of the filaments 703 can be secured relative to one another at the distal coupler 706. As such, the second ends of the filaments 703 terminate within the cavity 718, below the plane defined by the ridge 710. The resulting mesh structure thus has a "single layer" delivery configuration in which the distal coupler 706 is longitudinally spaced apart from the proximal coupler 704 by a distance greater than the longitudinal distance between the distal and proximal couplers 706, 704 when the occlusive member 702 is in an expanded state. As such, when the occlusive member 702 is in a delivery configuration, the occlusive member 702 is elongated such that no portion or substantially no portion of any filament 703 radially overlaps another portion of the same filament 703. When the occlusive member 702 is released from the delivery sheath, the proximal and distal couplers 704, 706 move longitudinally closer together, thus creating the bowed second portion 714 and cavity 718. The disclosed single layer delivery configuration advantageously allows for a mesh having a lower delivery profile, and thus enables delivery of the occlusive member through smaller diameter delivery catheters as compared to occlusive members having a double layer or quadruple layer delivery configuration.

In some embodiments, the second portion 714 of the wall has a contour or shape that substantially follows the contour or shape of the first portion 712 of the wall, or the first and second portions 714, 712 can have different contours or shapes. In these and other embodiments, a radius of curvature of all or a portion of the second portion 714 of the wall can be different than the radius of curvature of all or a portion of the first portion 712 of the wall. In these and other embodiments, the second portion 714 of the wall can have a radius of curvature that is greater than, less than, or substantially equal to the radius of curvature of the first portion 712 of the wall. The second portion 714 of the occlusive member 702 can have a substantially constant slope along its length (e.g., between the ridge 710 and the distal coupler 706), or all or a portion of the length may be convex towards the aneurysm wall (while still maintaining cavity 718), or all or a portion of the length may be concave towards the aneurysm wall.

The mesh of the disclosed occlusive members can be formed of metal wires, polymer wires, or both, and the wires can include a resilient material, a material having shape memory, a material having superelastic properties, or combinations thereof. The mesh can, for example, be formed of 24, 32, 36, 48, 64, 72, 96, 128, or 144 filaments. The mesh can be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of a braided mesh have the same diameter. For example, in some embodiments, all of the filaments have a diameter of about 0.001 inches. In some embodiments, some of the filaments have different cross-sectional diameters. For example, some of the filaments can have a slightly thicker diameter to impart additional strength to the braided layers. In some embodiments, some of the filaments have a diameter of about 0.001 inches, and some of the filaments can a diameter of greater than 0.001 inches. The thicker filaments may impart greater strength to the braid without significantly increasing the device delivery profile, with the thinner wires offering some strength while filling-out the braid matrix density.

In some embodiments, the disclosed devices are generally constructed to track over a conventional guidewire in the cervical anatomy and into the cerebral vessels associated with the brain, and may be configured based on other designs that are already commercially available. For example, the disclosed elongated members can have lengths at least 125 cm long, for example, between about 125 cm and about 175 cm long. In some embodiments, these elongated members may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

In some embodiments, the elongated members are formed from stainless steel, nitinol, or other metal or alloy. In some embodiments, the elongated members are hollow, and in some embodiments, the elongated member are surrounded over some or all of their length by a coating, such as, for example, polytetrafluoroethylene. The elongated members can have a diameter that is generally constant along their length, or can have a diameter that tapers radially inwardly, along at least a portion of their length, as it extends in a distal direction.

The disclosed occlusive members can have a variety of different shapes and sizes in their expanded, unconstrained state. For example, the occlusive member can have a bullet shape, a barrel-shape, an egg shape, a dreidel shape, a bowl shape, a disc shape, a cylindrical or substantially cylindrical shape, a barrel shape or a chalice shape.

The elongated members can be movable within, over, or alongside other elongated members to position the disclosed flow restrictors or occlusive members at a desired location. The elongated members can be sufficiently flexible to allow manipulation, e.g., advancement or retraction, through tortuous passages. Tortuous passages may include, for example, catheter lumens, microcatheter lumens, blood vessels, urinary tracts, biliary tracts, and airways.

IV. EXAMPLES

The following examples are included to further describe some aspects of the present technology, and should not be used to limit the scope of the technology.

Example 1

Figure 8A:
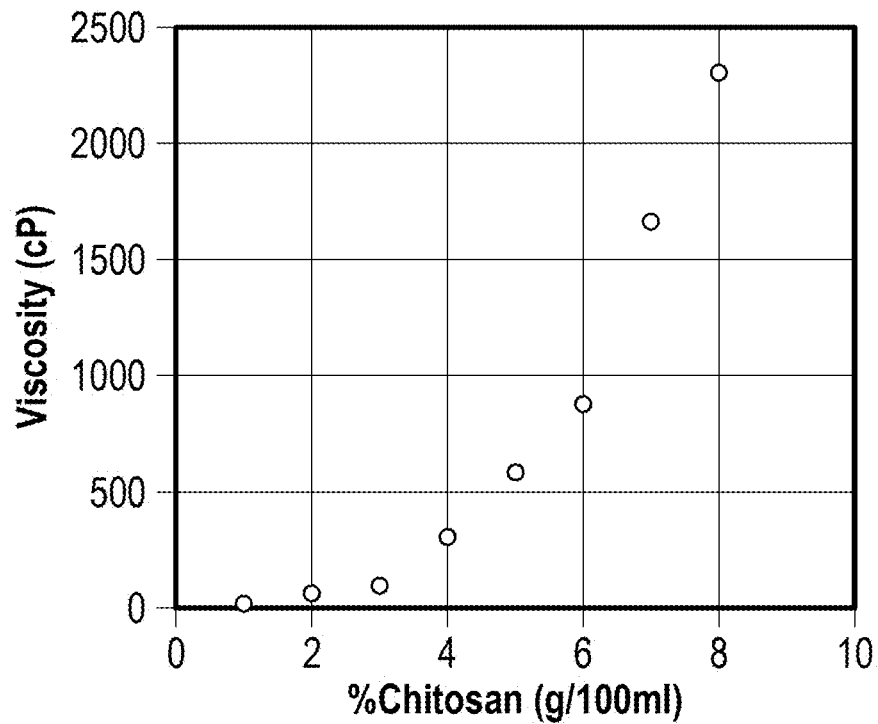
FIGS. 8A-8C are viscosity plots for chitosan solutions at several concentration levels, measured at room temperature and a shear rate of 1/s.
Figure 8B:
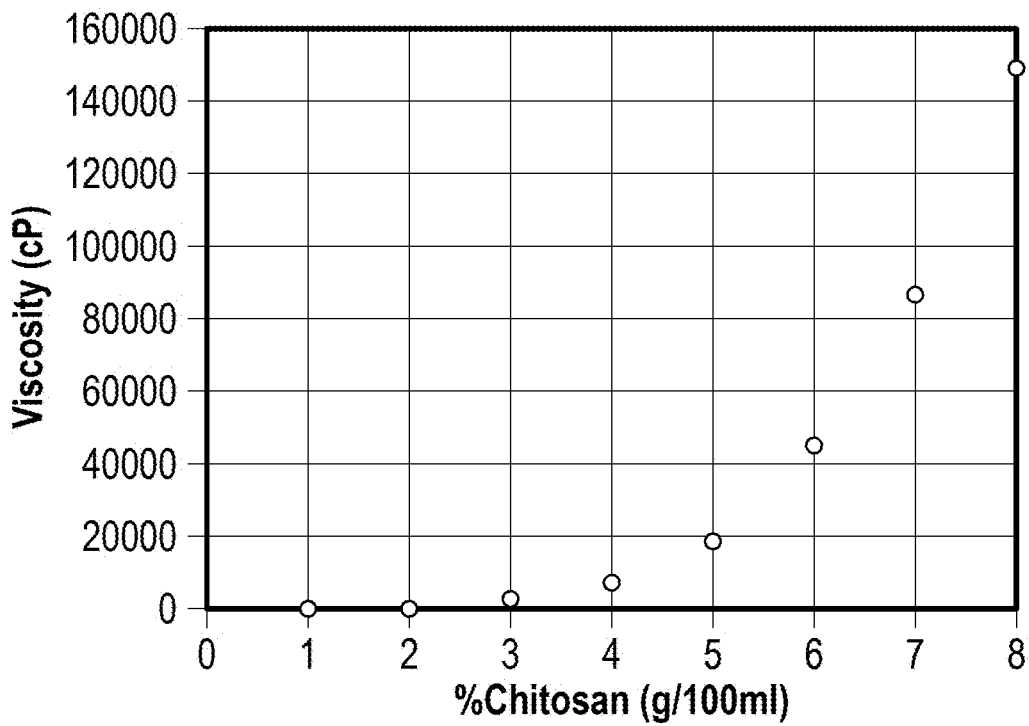

Entanglement concentrations for two different chitosans were determined by dissolving 115 kDa and 240 kDa weight average molecular weight chitosans in water at concentrations from 1% (w/v) to 8% (w/v), allowing the composition to age at room temperature and pressure for 1 day, and measuring viscosity using a TA Instruments DHR-20 2° cone and plate viscometer operated at 20° C. and a 1/s shear rate. Thirty measurements were taken for each concentration and averaged together. The results are plotted in FIG. 8A (115 kDa chitosan) and FIG. 8B (240 kDa chitosan). The inflection points for each curve show that the entanglement concentration was about 6% (w/v) for the 115 kDa sample and about 5% (w/v) for the 240 kDa sample.

The measured viscosities also changed over time at room temperature, and decreased at concentrations below, at and somewhat above the entanglement concentration. This can be seen from the data for the 240 kDa solutions shown below in Table 1. The entanglement concentration remained at about 5% (w/v) for measurements made at 7 and 14 days, but the measured viscosities decreased over time for concentrations below about 7% (w/v). At and above about 7% (w/v), the measured viscosities increased over time, likely due to hydrogen bonding and the promotion of growing dense hydrogen bonded domains.

TABLE 1

| % (w/v) Chitosan | Viscosity (cP) Day 0 | Viscosity (cP) Day 7 | Viscosity (cP) Day 14 | Δ Viscosity (%) Day 0 to Day 14 |
| --- | --- | --- | --- | --- |
| 1 | 67.3 | 57.6 | 49.1 | −27.0 |
| 2 | 368.8 | 260.8 | 245.8 | −33.4 |
| 3 | 2261.3 | 1586.4 | 1532.8 | −32.2 |
| 4 | 6565.0 | 4930.7 | 4562.3 | −30.5 |
| 5 | 17682.6 | 14794.6 | 12509.6 | −29.3 |
| 6 | 44620.8 | 41044.6 | 40643.1 | −8.9 |
| 7 | 86203.7 | 84683.6 | 85441.9 | −0.9 |
| 8 | 149299.0 | 148461.0 | 155498.0 | 4.2 |

Figure 8C:
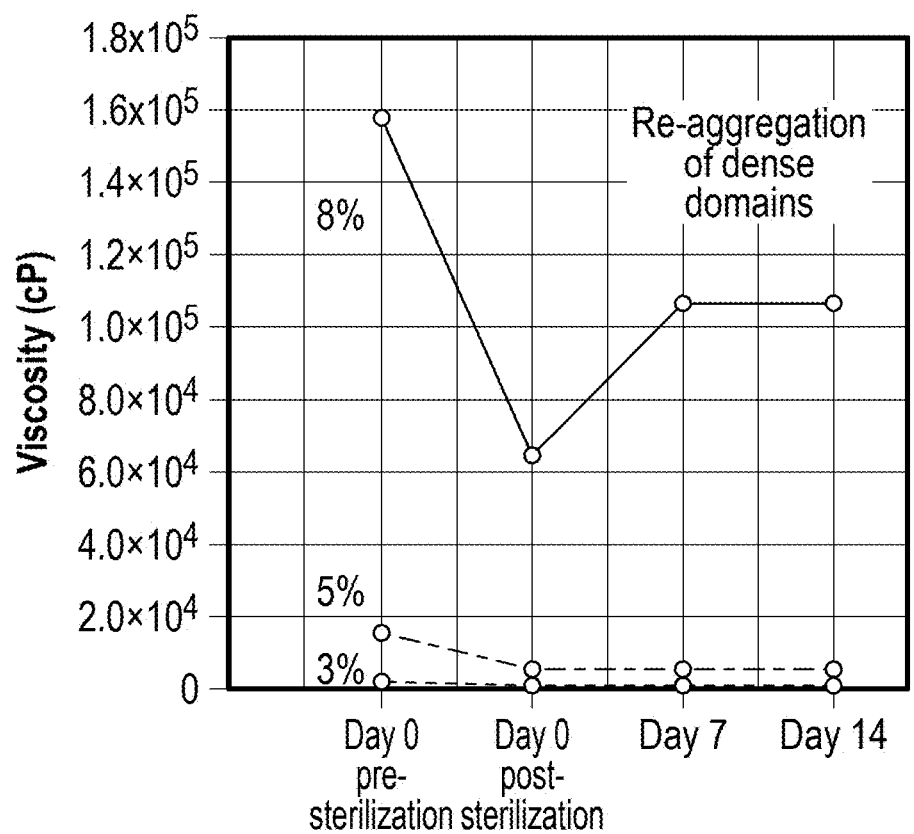

Steam sterilization also affected viscosity, causing an initial drop on Day 0 followed by an increase by Day 7. This may be seen from the data in Table 2 below and the graph in FIG. 8C. Sterilization at was performed for 20 minutes at 121° C. and 0.082 bar (1.2 psi), using a tape indicator to verify the sterilization temperature.

TABLE 2

| % (w/v) Chitosan | Viscosity (cP) Pre-Sterilization Day 0 | Viscosity (cP) Post-Sterilization Day 0 | Viscosity (cP) Post-Sterilization Day 7 | Viscosity (cP) Post-Sterilization Day 14 |
| --- | --- | --- | --- | --- |
| 3 | 1801.0 | 510.4 | 537.7 | 515.9 |
| 5 | 15531.2 | 5312.5 | 5863.0 | 6207.2 |
| 8 | 158417.0 | 64650.8 | 106870.0 | 106968.0 |

Example 2

Biopolymer compositions were prepared using 6% (w/v) 240 kDa chitosan with an 85% degree of deacetylation, 45% (w/v) iohexol contrast agent, and varying amounts of BGP disodium salt physical crosslinking agent. The compositions were steam sterilized at 121° C. for 20 minutes and evaluated to determine their pH, viscosity at 1/s and 20° C. before sterilization, and appearance. The results are set out below in Table 3.

TABLE 3

| % (w/v) Chitosan | % (w/v) Iohexol | % (w/v) BGP | pH | Viscosity (cP) | Appearance After Sterilization |
| --- | --- | --- | --- | --- | --- |
| 6 | 45 | 0 | 5.6-6.0 | 34,888 | Clear Fluid |
| 6 | 45 | 0.25 | 5.6-6.0 | 21,601 | Clear Fluid |
| 6 | 45 | 0.50 | 6.0-7.0 | 25,772 | Clear Fluid |
| 6 | 45 | 2 | 6.0-7.0 | 27,610 | Weak Gel |
| 6 | 45 | 4 | — | — | Gel |
| 6 | 45 | 6 | — | — | Gel |
| 6 | 45 | 10 | — | — | Gel |

After heat sterilization and annealing, the compositions containing 2% or less of BGP were microcatheter-injectable, but the compositions containing more than 2% BGP formed gels that were not microcatheter-injectable.

Example 3

Using the method of Example 2, biopolymer compositions were prepared using 6% (w/v) 240 kDa chitosan with an 85% degree of deacetylation, 2% (w/v) BGP disodium salt physical crosslinking agent, and varying amounts of iohexol contrast agent. The compositions were steam sterilized at 121° C. for 20 minutes and evaluated to determine their appearance. Compositions containing 0%, 4%, 10%, and 20% iohexol turned cloudy after sterilization, indicating that the chitosan had precipitated from solution. Compositions containing 30% (w/v), 45% (w/v), and 80% (w/v) iohexol remained clear after sterilization, indicating that the chitosan remained solubilized.

Example 4

Using the method of Example 2, biopolymer compositions were prepared using 6% (w/v) 240 kDa chitosan with an 85% degree of deacetylation, 1.5% (w/v) BGP disodium salt physical crosslinking agent, 45% (w/v) iohexol, and varying amounts of genipin chemical crosslinking agent. Compositions containing 0.001% (w/v) genipin formed a liquid with low cohesiveness. Compositions containing 0.01% (w/v) genipin formed a cohesive, deformable, viscoelastic hydrogel. Compositions containing 0.1% (w/v) genipin formed a brittle solid.

The compositions containing 0.01% (w/v) genipin were injected through a microcatheter having an inside diameter of 3.3 mm (0.13 inches) into a beaker containing 37° C. water. Within 2 to 3 minutes, while the iohexol diffused into the surrounding water, the transparent hydrogel stream transformed itself into an opaque white viscoelastic solid strand. Strand formation occurred when the composition was injected directly into the water as well as when the composition was injected into air above the beaker and allowed to fall into the water.

Example 5

Two biopolymer compositions (Formulation 1 and Formulation 2) were prepared using 5% (w/v) chitosan with at least 90% degree of deacetylation, 1% (w/v) BGP disodium salt, 60% (w/v) iohexol, and 0.007% (w/v) genipin. Formulation 1 included a high molecular weight chitosan, which exhibited a viscosity of 100 mPa-s when measured as a 1% (w/v) solution in water at 20° C. and 1/s. Formulation 2 included a low molecular weight chitosan, which exhibited a viscosity of 67 mPa-s when measured as a 1% (w/v) solution in water at 20° C. and 1/s. The compositions were steam sterilized before testing was performed.

Mechanical testing was performed using a TA Instruments DHR-20 with a 40 mm diameter 2° cone and plate geometry with a 56 μm gap. Testing was performed at 37° C. and using a solvent trap with water. Oscillation frequency measurements were obtained at 10% strain and an angular frequency from 400 rad/s to 0.1 rad/s, and the crossover point was recorded. Oscillation amplitude measurements were obtained at an angular frequency of 10 rad/s and a strain from 1% to 100%. The analysis was performed at 10% strain, and the linear viscoelastic region parameters were recorded and used to determine the storage and loss moduli. pH testing was performed at room temperature (approximately 20° C.) using a digital pH meter. Solubility testing was performed by placing 0.5 mL of the composition in 10 mL of 1X phosphate-buffered saline for 30 minutes at room temperature with shaking. The absorbance of the composition was measured at room temperature using a PerkinElmer Lambda 25 UV/Vis Spectrophotometer.

The properties of Formulation 1 and Formulation 2 are listed in Table 4 below.

TABLE 4

| Formulation | pH | Peak Absorbance Wavelength (Absorbance Value) | Solubility |
| --- | --- | --- | --- |
| 1 | 5.3-5.6 | 612.59 nm (2.51 A) | Not dissolved |
| 2 | 5.3-5.6 | 612.27 nm (2.72 A) | Not dissolved |

Figure 9A:
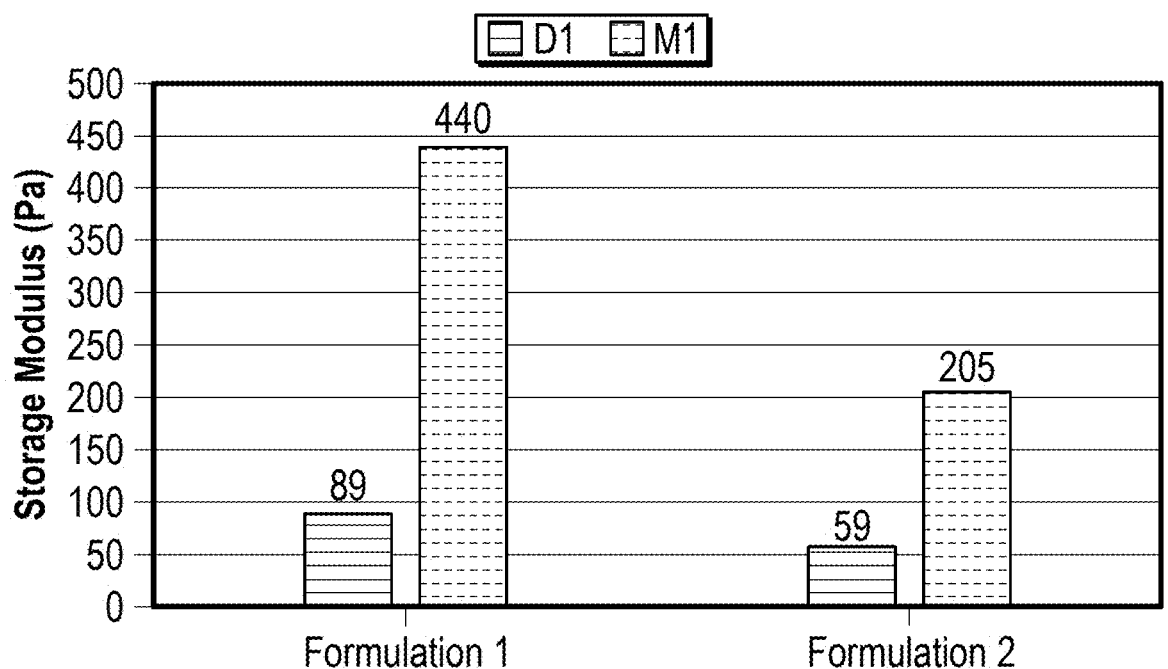
FIG. 9A is a graph illustrating the storage moduli of biopolymer compositions after sterilization and aging at room temperature for up to one month.
Figure 9B:
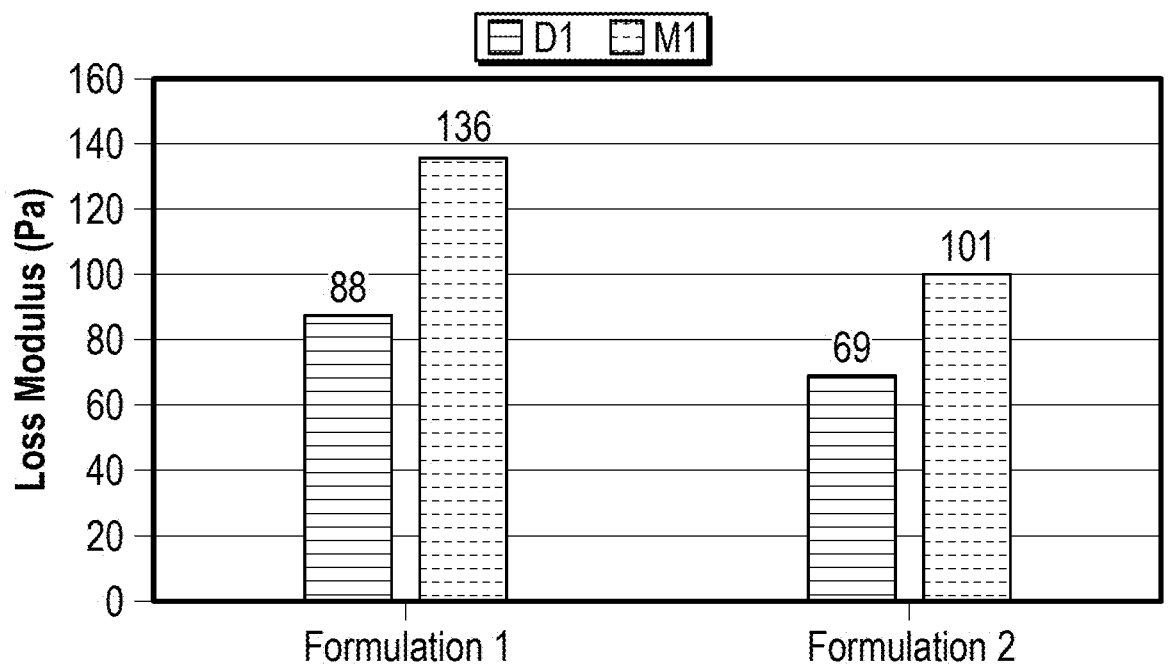
FIG. 9B is a graph illustrating the loss moduli of biopolymer compositions after sterilization and aging at room temperature for up to one month.

FIGS. 9A and 9B are graphs illustrating the storage moduli and loss moduli of Formulations 1 and 2 after aging at room temperature for 1 day (D1) and 1 month (M1) at room temperature. Formulation 1 exhibited higher storage modulus values than Formulation 2. Both formulations were unstable over the aging time period, as indicated by significant increases in the storage modulus and loss modulus from D1 to M1. It is hypothesized that the instability is caused by mobility of the BGP disodium salt over time, causing the hydrophobic domains within the chitosan to aggregate and form a stiffer but more brittle structure.

Example 6

Five biopolymer compositions (Formulations 3-7) were prepared using varying amounts of chitosan (at least 85% deacetylation, exhibiting a viscosity of at least 100 mPa-s when measured as a 1% solution in water at 20° C. and 1/s), BGP disodium salt, iohexol, and genipin, as listed in Table 5 below. The compositions were steam sterilized before testing. Mechanical testing was performed according to the methods described in Example 5.

TABLE 5

| Formulation | % (w/v) Chitosan | % (w/v) BGP | % (w/v) Iohexol | % (w/v) Genipin |
|---|---|---|---|---|
| 3 | 4 | 0.5 | 60 | 0.007 |
| 4 | 4 | 1.5 | 60 | 0.007 |
| 5 | 5 | 1 | 60 | 0.007 |
| 6 | 6 | 0.5 | 60 | 0.007 |
| 7 | 5 | 1.5 | 60 | 0.007 |

Figure 10A:
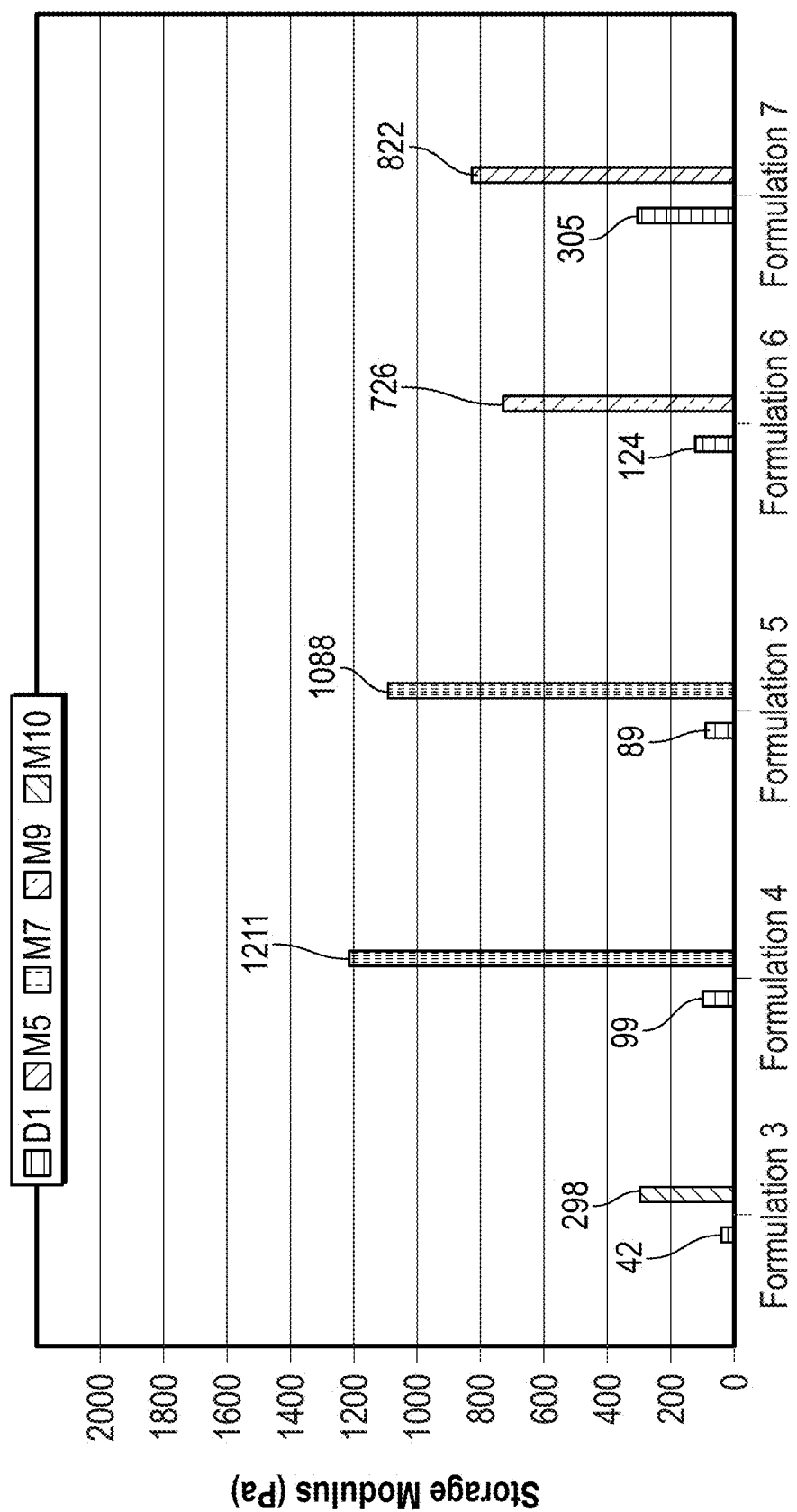
FIG. 10A is a graph illustrating the storage moduli of biopolymer compositions after sterilization and aging at room temperature for up to 10 months.
Figure 10B:
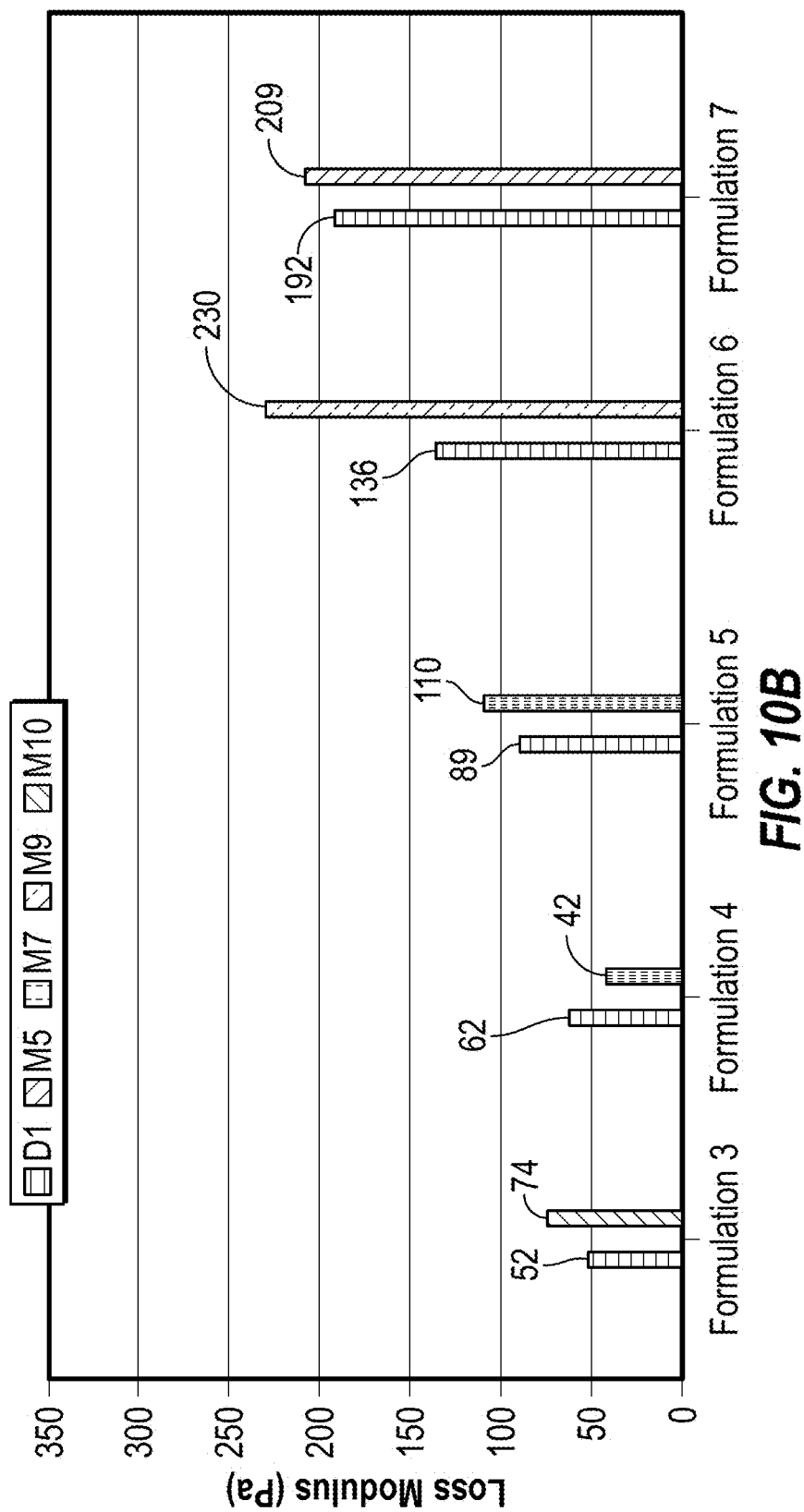
FIG. 10B is a graph illustrating the loss moduli of biopolymer compositions after sterilization and aging at room temperature for up to 10 months.

FIGS. 10A and 10B are graphs illustrating the storage moduli and loss moduli of Formulations 3-7, respectively, after aging at room temperature from 1 day (D1) up to 5 months (M5) (Formulation 7), 7 months (M7) (Formulations 4 and 5), 9 months (M9) (Formulation 6), or 10 months (M10) (Formulation 3). Formulation 3, which had the lowest concentration of chitosan and BGP, exhibited better stability over the aging time period, as evidenced by the relatively small increase in storage modulus (42 Pa at D1 versus 298 Pa at M10). The storage moduli of the other formulations increased more significantly over the same time period, in some cases, by several orders of magnitude (Formulation 4: 99 Pa at D1 versus 1211 Pa at M7; Formulation 5: 89 Pa at D1 versus 1088 Pa at M7; Formulation 6: 124 Pa at D1 versus 726 Pa at M9; Formulation 7: 305 Pa at D1 versus 822 Pa at M5). As described above, this increase may be attributed to mobility of the BGP and aggregation of chitosan hydrophobic domains over time, leading to increased stiffness and/or brittleness of the formulations over time. The loss moduli of the formulations exhibited much smaller variations over the aging period, thus indicating that the formulations were not becoming more liquid-like over time.

Example 7

Five biopolymer compositions (Formulations 8-12) were prepared using varying amounts of chitosan (at least 85% deacetylation, exhibiting a viscosity of at least 100 mPa-s when measured as a 1% solution in water at 20° C. and 1/s), hydroxyethylcellulose (HEC) (Natrosol™ 250 M pharm from Ashland, 720 kDa weight average), iohexol, and genipin, as listed in Table 6 below. The compositions were steam sterilized before testing.

TABLE 6

| Formulation | % (w/v) Chitosan | % (w/v) HEC | % (w/v) Iohexol | % (w/v) Genipin |
|---|---|---|---|---|
| 8 | 2 | 1 | 60 | 0.01 |
| 9 | 2 | 2 | 60 | 0.01 |
| 10 | 2.5 | 1.5 | 60 | 0.01 |
| 11 | 3 | 1 | 60 | 0.01 |
| 12 | 3 | 2 | 60 | 0.01 |

Testing was performed according to the methods described in Example 5. The properties of Formulations 8-12 are listed in Table 7 below.

TABLE 7

| Formulation | Peak Absorbance Wavelength (Absorbance Value) | pH | Solubility | Visual Appearance |
|---|---|---|---|---|
| 8 | 611.00 nm (2.34 A) | 5.56 | Not dissolved | Blue, clear, cohesive |
| 9 | 611.74 nm (2.19 A) | 5.34 | Not dissolved | Blue, clear, cohesive |
| 10 | 611.90 nm (3.68 A) | 5.32 | Not dissolved | Blue, clear, cohesive |
| 11 | 611.52 nm (2.99 A) | 5.52 | Not dissolved | Blue, clear, cohesive |
| 12 | 611.70 nm (2.52 A) | 5.42 | Not dissolved | Blue, clear, cohesive |

Figure 11A:
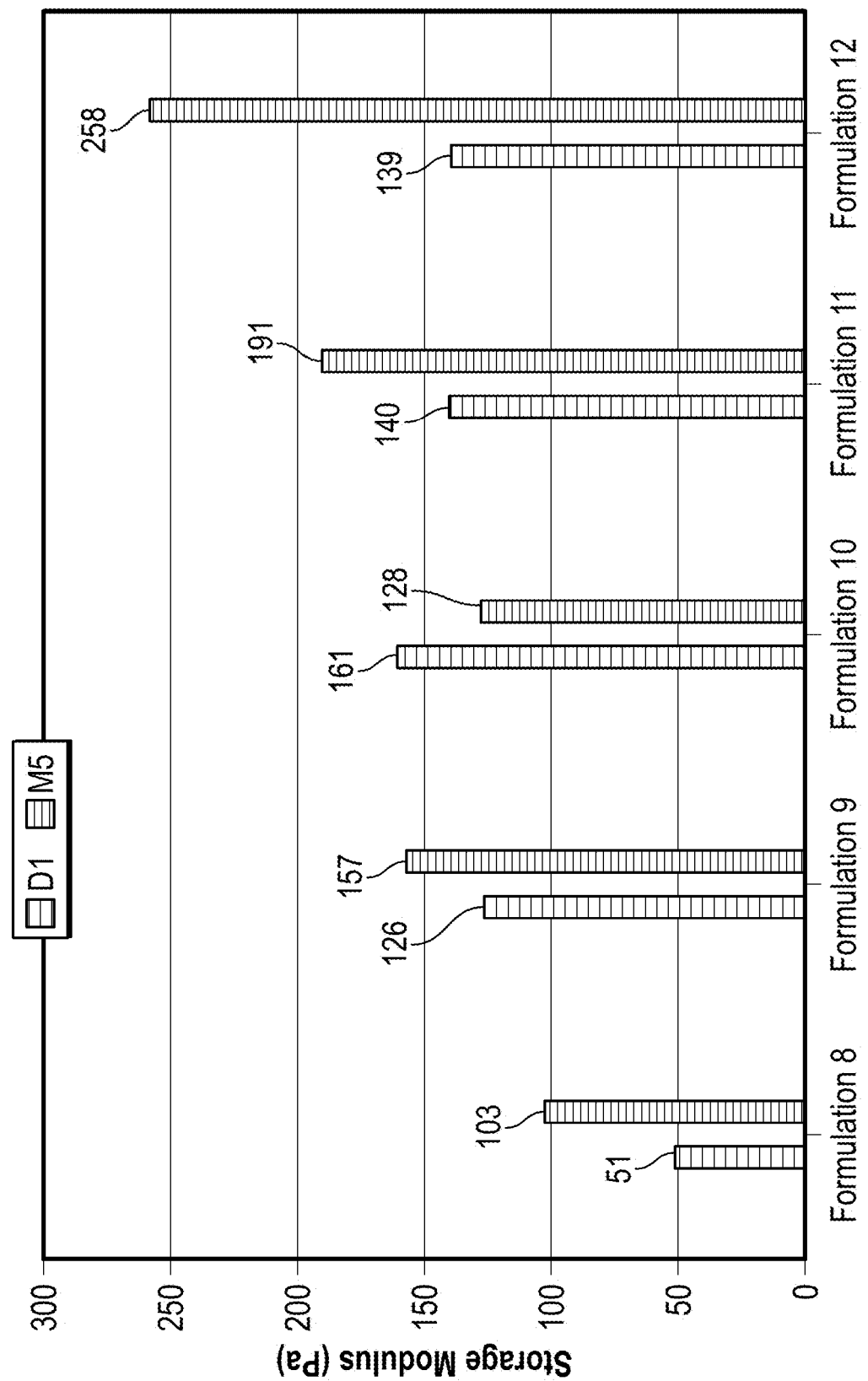
FIG. 11A is a graph illustrating the storage moduli of biopolymer compositions after sterilization and aging at room temperature for up to 5 months.
Figure 11B:
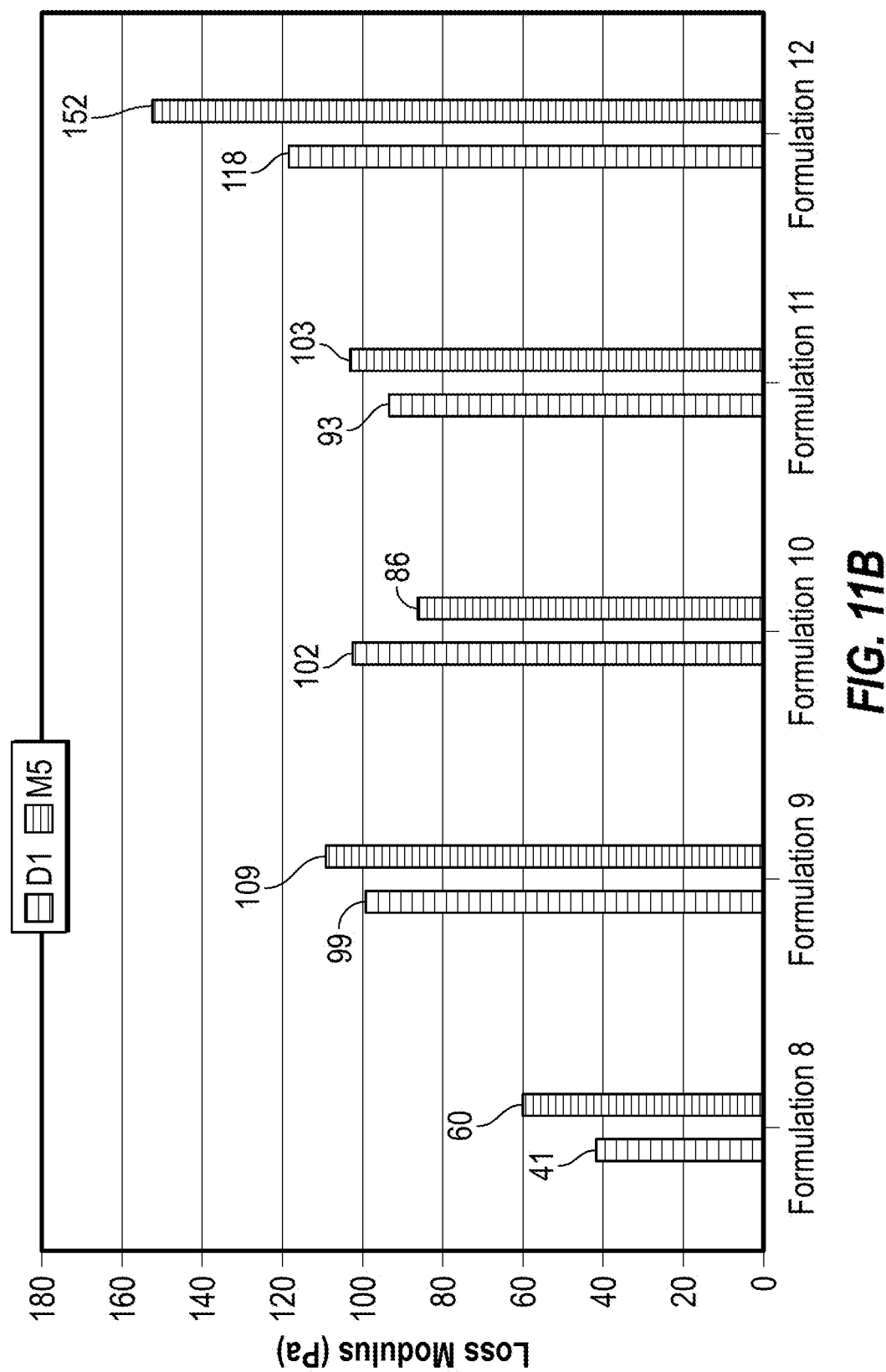
FIG. 11B is a graph illustrating the loss moduli of biopolymer compositions after sterilization and aging at room temperature for up to 5 months.

FIGS. 11A and 11B are graphs illustrating the storage moduli and loss moduli of Formulations 8-12, respectively, after aging at room temperature from 1 day (D1) to 5 months (M5). Formulations 9-11, which had intermediate amounts of chitosan and HEC, exhibited improved stability over the aging time period, as indicated by modest or no increases in their storage moduli (Formulation 9: 126 Pa at D1 versus 157 Pa at M5; Formulation 10: 161 Pa at D1 versus 128 Pa at M5; Formulation 11: 140 Pa at D1 versus 191 Pa at M5). The other two formulations exhibited more significant increases in storage moduli over time (Formulation 8: 51 Pa at D1 versus 103 Pa at M5; Formulation 12: 139 Pa at D1 versus 258 Pa at M5). The loss moduli of the formulations exhibited much smaller variations over the aging period, thus indicating that the formulations were not becoming more liquid-like over time.

Example 8

Three biopolymer compositions (Formulations 13-15) were prepared using varying amounts of chitosan (at least 85% deacetylation, exhibiting a viscosity of at least 100 mPa-s when measured as a 1% solution in water at 20° C. and 1/s), HEC (Natrosol™ 250 M pharm from Ashland, 720 kDa weight average), BGP disodium salt, iohexol, and genipin, as listed in Table 8 below. The compositions were steam sterilized before testing was performed.

TABLE 8

| Formulation | % (w/v) Chitosan | % (w/v) HEC | % (w/v) BGP | % (w/v) Iohexol | % (w/v) Genipin |
|---|---|---|---|---|---|
| 13 | 4 | 0 | 0.5 | 60 | 0.007 |
| 14 | 5 | 0 | 0 | 60 | 0.01 |
| 15 | 3 | 1 | 0 | 60 | 0.01 |

Formulations 13-15 were subjected to aging at 55° C. for 1 day (D1) and 50 days (D50, equivalent to 1 year aging at room temperature). Mechanical, pH, UV/Vis, and solubility testing was performed according to the methods described in Example 5. Biplane fluoroscopy imaging was performed to confirm radiopacity at D50, compared to a control sample (OMNIPAQUE™ from GE Healthcare). In vitro simulated use testing was performed using a silicone model of a cerebral aneurysm. The composition was injected into the aneurysm sac after a neck cover was positioned over the neck of the aneurysm. Biplane fluoroscopy was performed to confirm filling of the aneurysm and to visualize simulated blood flow (phosphate-buffered saline with contrast agent at 37° C.) through the parent vessel adjacent to the aneurysm. The properties of Formulations 13-15 at D1 and D50 (n=10) are listed in Tables 9-1 and 9-2 below.

TABLE 9-1

| Formulation | Time | Visual Appearance | pH | Peak Absorbance Wavelength (nm) | Absorbance Value (A) |
|---|---|---|---|---|---|
| 13 | D1 | Blue, clear, cohesive | 5.85 ± 0.03 | 607.0 ± 0.6 | 1.7 ± 0.1 |
| 13 | D50 | Blue, clear, cohesive, color separation | 5.80 ± 0.04 | 604.6 ± 4.4 | 1.7 ± 0.3 |
| 14 | D1 | Blue, clear, cohesive | 5.2 ± 0.05 | 612.7 ± 0.4 | 1.6 ± 0.2 |
| 14 | D50 | Blue, clear, cohesive | 5.7 ± 0.03 | 600.7 ± 2.9 | 2.4 ± 0.4 |
| 15 | D1 | Blue, clear, cohesive | 5.0 ± 0.06 | 613 ± 0.6 | 3 ± 0.6 |
| 15 | D50 | Blue, clear, cohesive | 5.5 ± 0.04 | 598 ± 2.2 | 2 ± 0.1 |

TABLE 9-2

| Formulation | Time | Radiopacity | Solubility | Simulated Use Testing |
|---|---|---|---|---|
| 13 | D1 | Pass | Not dissolved | Pass |
| 13 | D50 | Pass | Not dissolved | Pass |
| 14 | D1 | Pass | Not dissolved | Pass |
| 14 | D50 | Pass | Not dissolved | Pass |
| 15 | D1 | Pass | Not dissolved | Pass |
| 15 | D50 | Pass | Not dissolved | Pass |

Figure 12A:
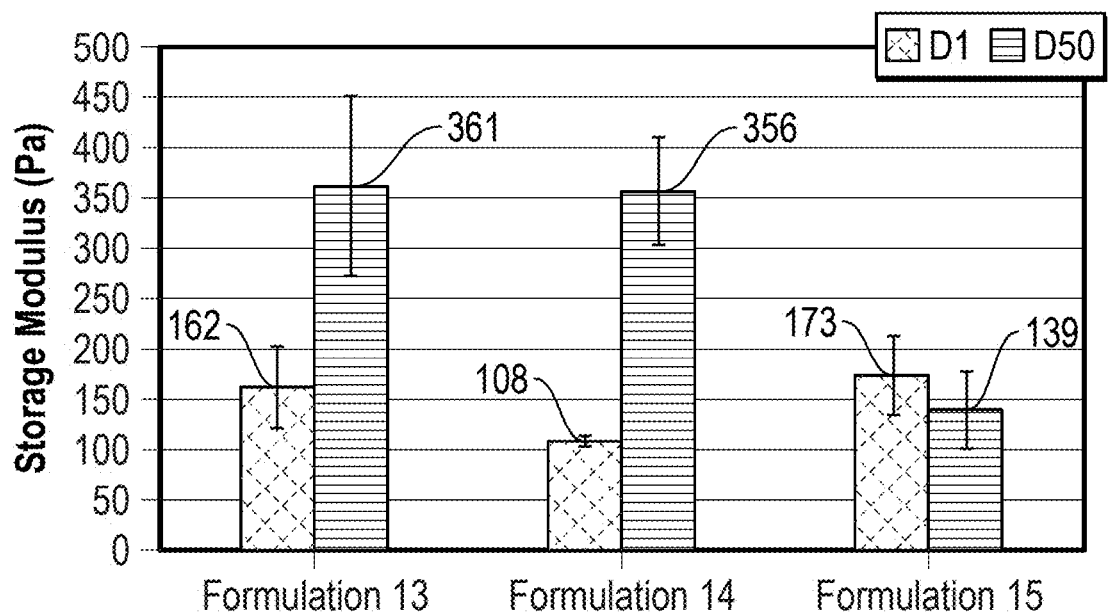
FIG. 12A is a graph illustrating the storage moduli of biopolymer compositions after sterilization and aging at elevated temperatures.
Figure 12B:
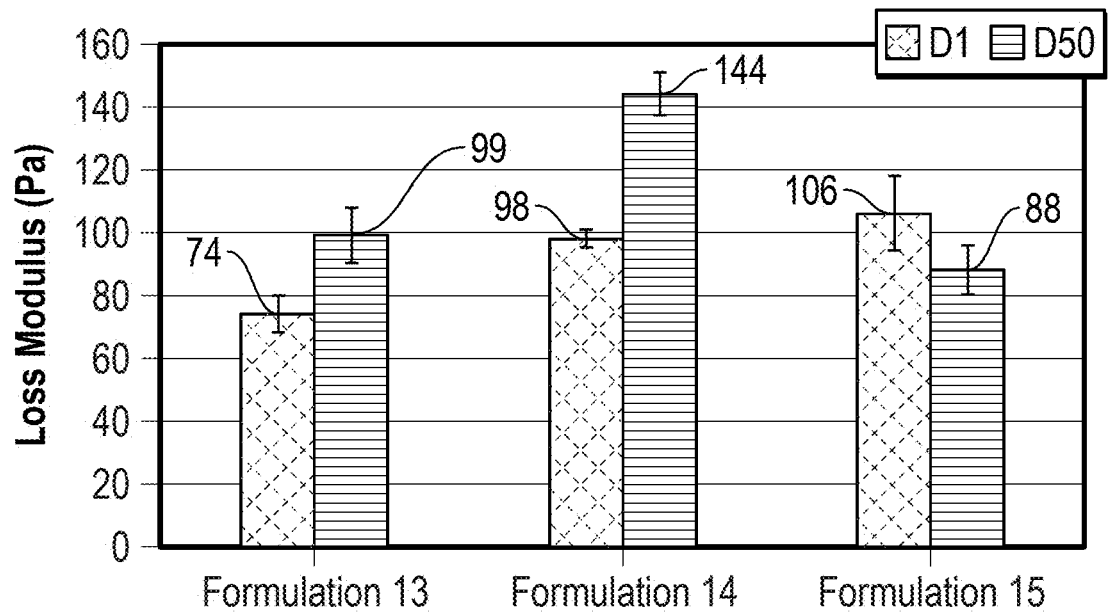
FIG. 12B is a graph illustrating the loss moduli of biopolymer compositions after sterilization and aging at elevated temperatures.

FIGS. 12A and 12B are graphs illustrating the storage moduli and loss moduli of Formulations 13-15, respectively, illustrating the storage and loss moduli of Formulations 13-15 at D1 and D50. The storage and loss moduli of Formulation 15 at D50 (simulating 1 year aging at room temperature) did not differ significantly from the initial moduli at D1, thus indicating that Formulation 15 is stable over extended time periods. Formulations 13 and 14 exhibited approximately 2- to 3-fold increases in storage moduli, and smaller increases in loss moduli, at D50.

Figure 12C:
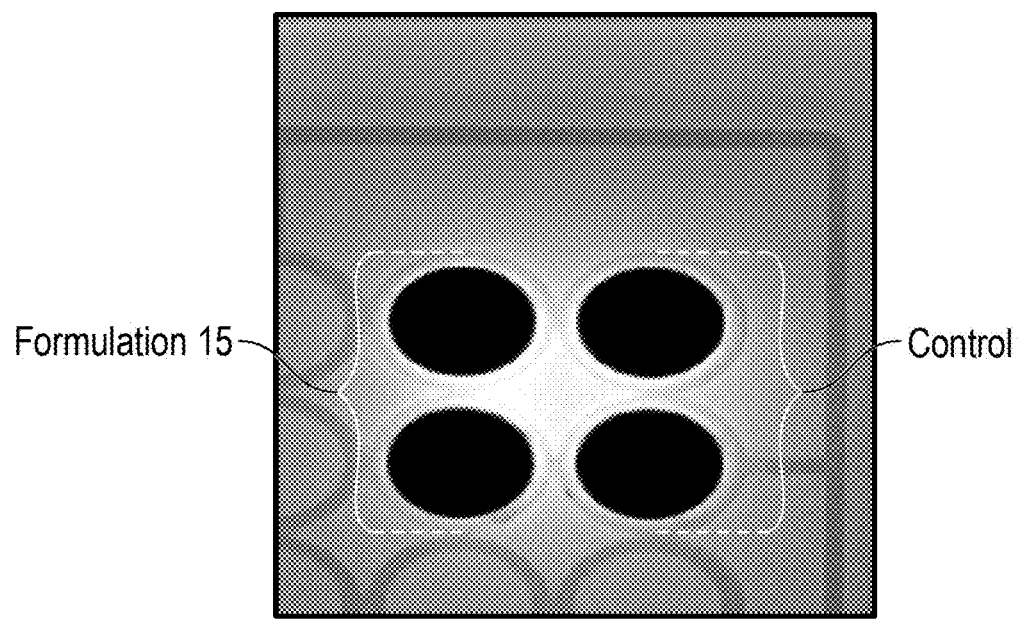
FIG. 12C is a radiographic image showing the radiopacity of a biopolymer composition after sterilization and aging at elevated temperatures.

FIG. 12C is a radiographic image showing the radiopacity of Formulation 15 (left two wells) versus a control formulation (right two wells). The radiopacity of Formulation 15 was comparable to the control formulation over aging period, with no degradation, fading, or settling observed. Similar results were obtained with Formulations 13 and 14 (not shown).

Figure 12E:
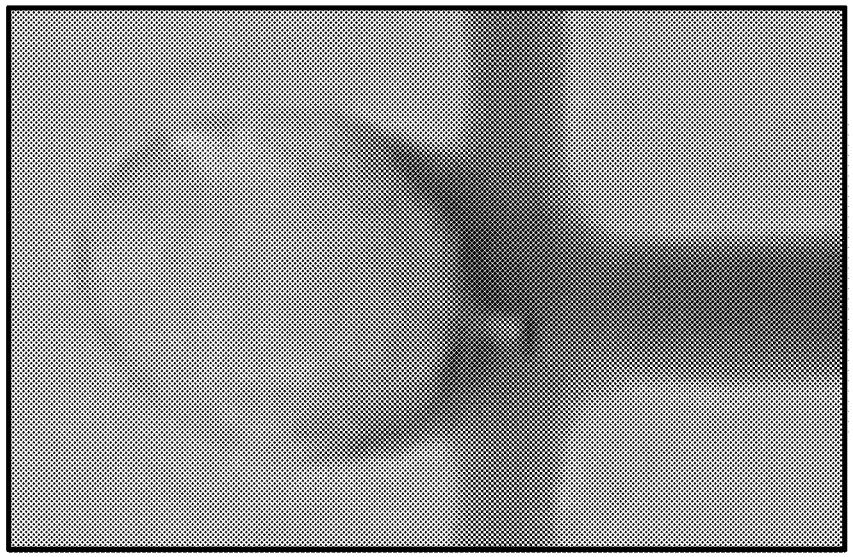
FIGS. 12D and 12E are radiographic images showing the results of in vitro simulated use testing of a biopolymer composition after sterilization and aging at elevated temperatures.
Figure 12D:
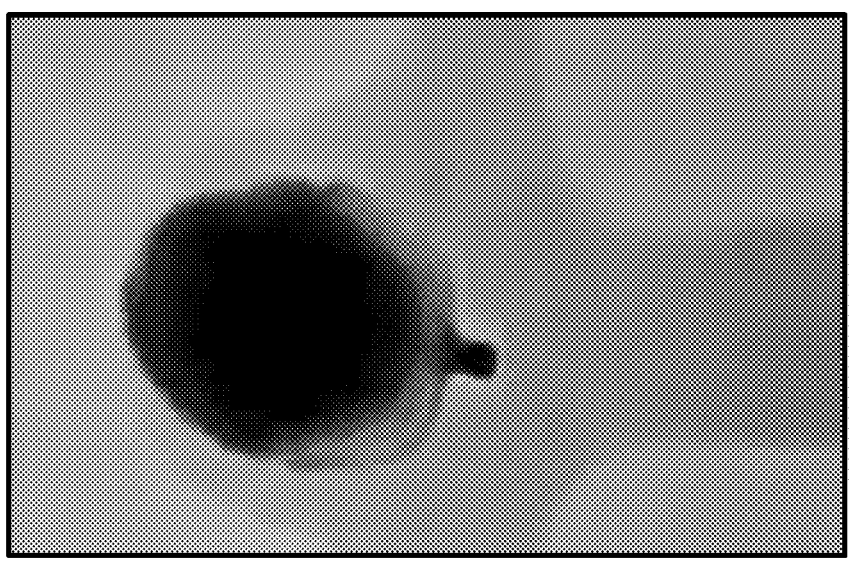

FIGS. 12D and 12E are radiographic images showing the results of in vitro simulated use testing for Formulation 15. As shown in FIG. 12D, Formulation 15 uniformly filled the entire aneurysm cavity with no leakage into the parent vessel. As shown in FIG. 12E, after filling of the aneurysm, simulated blood flow through the parent blood vessel was blocked from entering the aneurysm cavity (the radiopacity from Formulation 15 was subtracted from FIG. 12E). Similar results were obtained with Formulations 13 and 14 (not shown).

Example 9

FIGS. 13A-13D are photographic images (FIGS. 13A and 13C) and radiographic images (FIGS. 13B and 13D) of in vitro simulated use testing of a biopolymer composition (Formulation 13) prepared using 4% (w/v) chitosan (at least 85% deacetylation, exhibiting a viscosity of at least 100 mPa-s when measured as a 1% solution in water at 20° C. and 1/s), 0.5% (w/v) BGP disodium salt, 60% (w/v) iohexol, and 0.007% (w/v) genipin. The compositions were steam sterilized before testing. Testing was performed according to the methods described in Example 8. The model aneurysm had a width of 5 mm and a height of 7.7 mm.

Figure 13B:
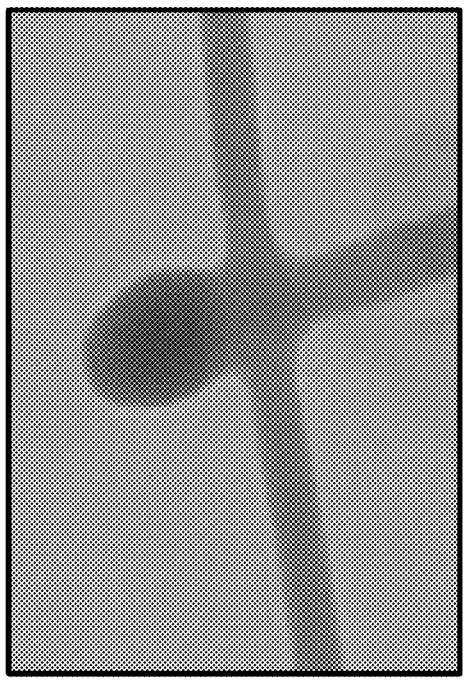
FIGS. 13A-13D are images showing the results of in vitro simulated use testing of a biopolymer composition after sterilization and aging at elevated temperatures.
Figure 13D:
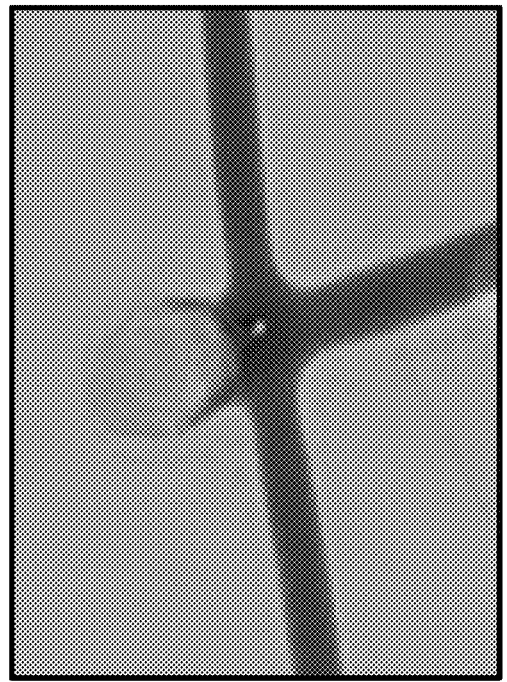
Figure 13A:
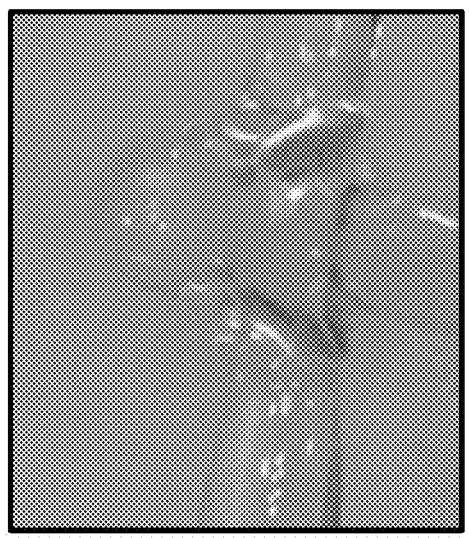

FIGS. 13A and 13B illustrate the model aneurysm before introduction of the composition. As shown in FIG. 13B, simulated blood flow through the parent vessel filled the entire aneurysm cavity.

Figure 13C:
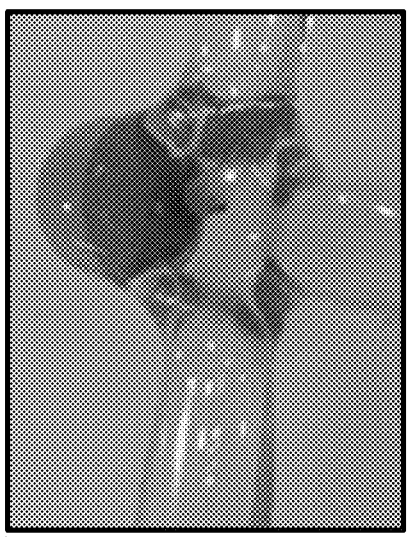

FIGS. 13C and 13D illustrate the model aneurysm after deployment of a neck cover (3.8 mm diameter) and introduction of Formulation 13 into the aneurysm cavity. As shown in FIG. 13C, Formulation 13 uniformly filled the entire aneurysm cavity with no leakage into the parent vessel. As shown in FIG. 13D, simulated blood flow through the parent vessel was blocked from entering the aneurysm cavity (the radiopacity from Formulation 13 was subtracted from FIG. 13D).

Example 10

Figure 14C:
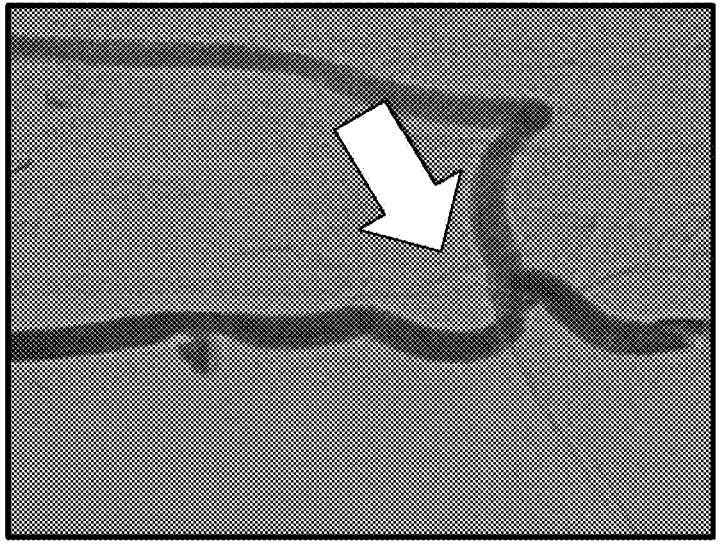
FIGS. 14A-14C are radiographic images showing the results of in vivo testing of a biopolymer composition in a canine model.
Figure 14B:
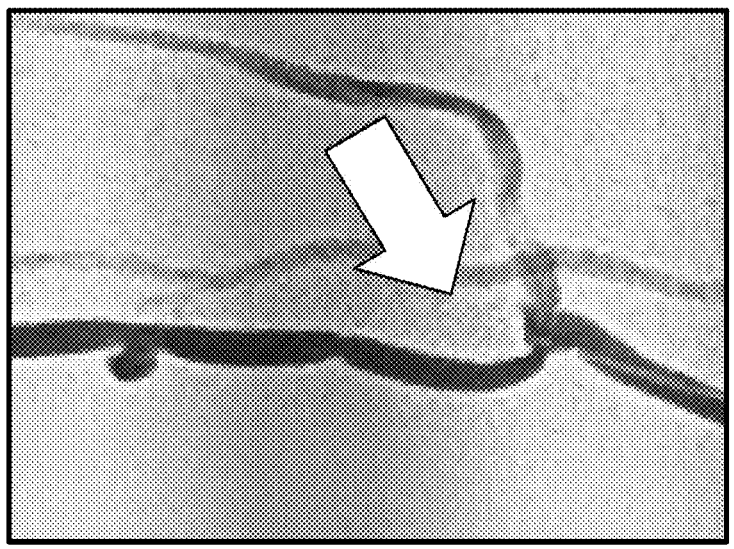
Figure 14A:
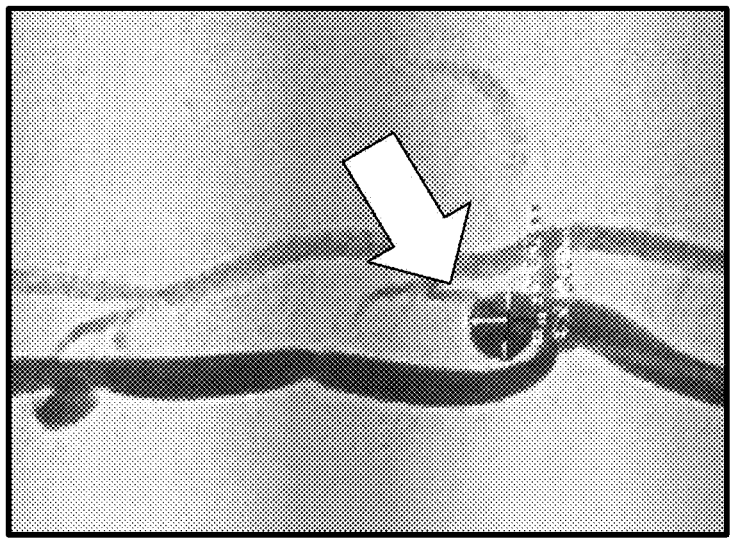

FIGS. 14A-14C are radiographic images showing in vivo testing of Formulation 13 in a canine model. Three canines, each with four created sidewall aneurysms, were used in the study. The target aneurysm size was 6 mm to 9 mm, although aneurysms outside that range were permitted in the study. After obtaining femoral access, the target aneurysm was imaged via fluoroscopy, and aneurysm height, width, depth, and neck measurements were collected. A microcatheter was delivered to the target aneurysm via a guide catheter and guidewire. A neck cover was then introduced into the aneurysm, followed by filling with Formulation 13. Treatment was performed with the objective of complete obliteration of the aneurysm without risking herniation of the neck cover or formulation into the parent artery. Angiographic data was recorded following each treatment and immediately prior to termination (Day 30) to assess occlusion and performance.

Prior to treatment (FIG. 14A), contrast agent introduced into the vasculature filled the target aneurysm (indicated by arrow). After treatment with a 9.75 mm neck cover and Formulation 13 (FIG. 14B), the contrast agent was obstructed from entering the aneurysm cavity, indicating successful occlusion of the cavity. The aneurysm remained occluded after 30 days (FIG. 14C), thus demonstrating successful long-term treatment.

Figure 15C:
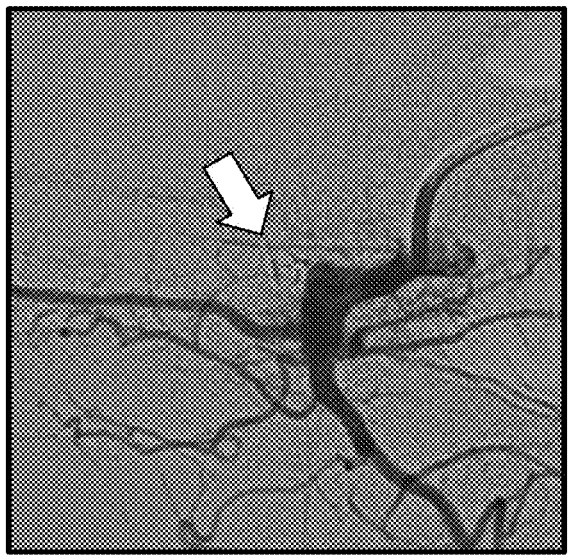
FIGS. 15A-15C are radiographic images showing the results of in vivo testing of a biopolymer composition in a lapine model.
Figure 15B:
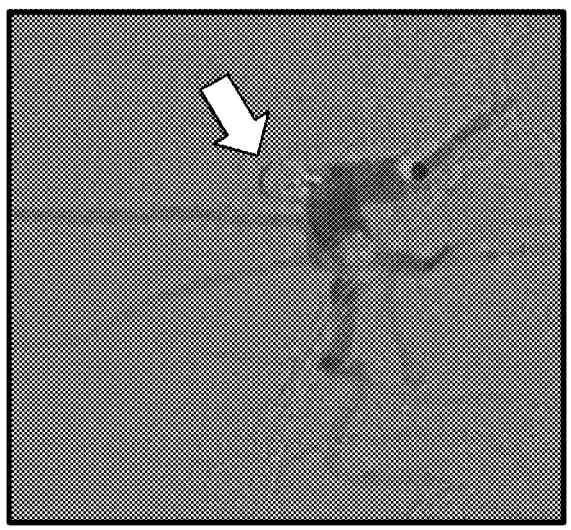
Figure 15A:
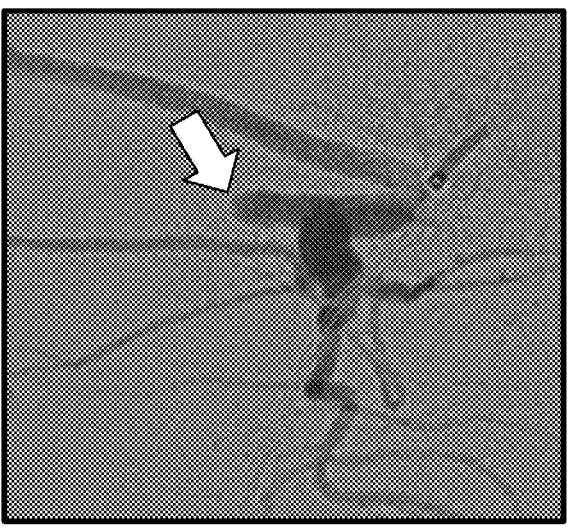

FIGS. 15A-15C are radiographic images showing in vivo testing of Formulation 13 in a lapine model. A different animal model was used in this study for the purposes of evaluating performance in different aneurysm sizes. Nine rabbits, each with one created side wall aneurysm, were used in the study. The target aneurysm size was 2.5 mm to 4.6 mm, although aneurysms outside that range were permitted in the study. The study procedure was the same as the procedure for the canine models above.

Prior to treatment (FIG. 15A), contrast agent introduced into the vasculature filled the target aneurysm (indicated by arrow). After treatment with a 3.3 mm neck cover and Formulation 13 (FIG. 15B), the contrast agent was obstructed from entering the aneurysm cavity, indicating successful occlusion of the cavity. The aneurysm remained occluded after 30 days (FIG. 15C), thus demonstrating successful long-term treatment.

CONCLUSION

Although many of the embodiments are described above with respect to systems, devices, and methods for treating saccular intracranial aneurysms, the technology is applicable to other applications and/or other approaches. For example, suitable features of described systems, devices, compositions, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g., via occlusion of vessel(s) feeding a tumor), perivascular leaks, varicose veins (e.g., via occlusion of one or more truncal veins such as the great saphenous vein), hemorrhoids, and sealing endoleaks adjacent to artificial heart valves, covered stents, and abdominal aortic aneurysm devices, among other examples.

Moreover, other embodiments in addition to those described herein are within the scope of the technology. For example, embodiments of the disclosed systems, devices, compositions, and methods can be applied to surface modification of medical devices, such as by grafting a biopolymer under the surface of a device to modulate foreign body responses and induce a regenerative healing response that may mitigate scar formation and encapsulation cascades. Embodiments of the disclosed systems, devices, compositions, and methods can also be applied to generate nano-architecture scaffolds for wound healing, burn treatment or tissue reconstruction. Because relatively high biopolymer concentrations may be employed, embodiments of the disclosed systems, devices, compositions, and methods may employ electrospinning, wet-spinning, film casting and other techniques to generate architectures including nanofibers, porous sponges and the like. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-15C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A biopolymer composition for treating an aneurysm, the biopolymer composition comprising:
an injectable hydrogel comprising:
at least 2% w/v chitosan, wherein the chitosan has a weight average molecular weight of at least 100 kDa;
a chemical crosslinker comprising genipin, wherein the genipin forms covalent bonds between different chains of the chitosan; and
at least 1% w/v hydroxyethyl cellulose, wherein the hydroxyethyl cellulose interacts noncovalently with the chitosan to inhibit ex vivo precipitation of the chitosan, wherein the hydroxyethyl cellulose has a weight average molecular weight of at least 500 kDa, wherein the hydroxyethyl cellulose comprises a viscosity of at least 2000 Pa-s when measured as a 1% w/v solution at 20° C. and a shear rate of 1/s, and wherein the hydroxyethyl cellulose does not form covalent bonds with the genipin,
wherein the injectable hydrogel comprises an ex vivo storage modulus of at least 100 Pa at 37° C. over a linear viscoelastic region of the injectable hydrogel, and
wherein the injectable hydrogel is configured to occlude the aneurysm without undergoing a phase transition.

2. The biopolymer composition of claim 1, wherein the injectable hydrogel does not undergo a phase transition upon exposure to in vivo conditions.

3. The biopolymer composition of claim 1, wherein the chitosan comprises a viscosity of at least 50 Pa-s when measured as a 1% w/v solution at 20° C. and a shear rate of 1/s.

4. The biopolymer composition of claim 1, wherein the injectable hydrogel comprises at least 2% w/v and no more than 9% w/v of the chitosan.

5. The biopolymer composition of claim 1, wherein the hydroxyethyl cellulose is configured to inhibit ex vivo precipitation of the chitosan over a period of at least 1 month.

6. The biopolymer composition of claim 1, wherein the injectable hydrogel comprises at least 1% w/v and no more than 5% w/v of the hydroxyethyl cellulose.

7. The biopolymer composition of claim 1, wherein the injectable hydrogel comprises a contrast agent.

8. The biopolymer composition of claim 1, wherein the injectable hydrogel comprises a physical crosslinker forming noncovalent interactions with the chitosan.

9. A biopolymer composition for treating an aneurysm, the biopolymer composition comprising:
an injectable hydrogel comprising:
at least 2% w/v chitosan, wherein the chitosan has a weight average molecular weight of at least 100 kDa;
a chemical crosslinker comprising genipin, wherein the genipin forms covalent bonds with the chitosan; and
at least 1% w/v hydroxyethyl cellulose, wherein the hydroxyethyl cellulose interacts noncovalently with the chitosan to inhibit ex vivo phase separation of the chitosan, wherein the hydroxyethyl cellulose has a weight average molecular weight of at least 500 kDa, wherein the hydroxyethyl cellulose comprises a viscosity of at least 2000 Pa-s when measured as a 1% w/v solution at 20° C. and a shear rate of 1/s, and wherein the hydroxyethyl cellulose does not form covalent bonds with the genipin,
wherein the injectable hydrogel comprises an ex vivo storage modulus that is greater than an ex vivo loss modulus of the injectable hydrogel over a linear viscoelastic region of the injectable hydrogel, and
wherein the injectable hydrogel is configured to be delivered into the aneurysm without undergoing a phase transition.

10. The biopolymer composition of claim 9, wherein the injectable hydrogel comprises a preformed, ex vivo state that is configured to be stable at room temperature over a storage period of at least 1 month.

11. The biopolymer composition of claim 10, wherein the ex vivo storage modulus of the injectable hydrogel varies by no more than 25% over the storage period.

12. The biopolymer composition of claim 9, wherein the hydroxyethyl cellulose is configured to form an interpenetrating network with the chitosan.

13. The biopolymer composition of claim 9, wherein the hydroxyethyl cellulose is configured to space apart hydrophobic groups on the chitosan.

14. The biopolymer composition of claim 9, wherein the hydroxyethyl cellulose is configured to inhibit ex vivo phase separation of the chitosan after the injectable hydrogel has undergone heat sterilization.

15. The biopolymer composition of claim 1, wherein the injectable hydrogel comprises from 0.005% w/v to 0.01% w/v of the genipin.

16. The biopolymer composition of claim 7, wherein the contrast agent comprises one or more of the following: iohexol, iodixanol, iopamidol, diatrizoate, iothalamate, iopromide, ioversol, ioxilan, iothalamate/meglumine, ioxaglate/meglumine, diatrizoate/meglumine, iodomide sodium, or metrizamide.

* * * * *